US012727775B2

(12) United States Patent
Akbari et al.

(10) Patent No.: US 12,727,775 B2
(45) Date of Patent: Sep. 8, 2026

(54) PORTABLE DEVICE FOR QUANTITATIVE MEASUREMENT OF TISSUE AUTOREGULATION AND NEUROVASCULAR COUPLING USING EEG, METABOLISM, AND BLOOD FLOW DIAGNOSTICS

(71) Applicant: THE REGENTS OF THE UNIVERSITY OF CALIFORNIA, Oakland, CA (US)

(72) Inventors: Yama Akbari, Irvine, CA (US); Robert H. Wilson, Irvine, CA (US); Christian Crouzet, Irvine, CA (US); Thomas Milner, Irvine, CA (US); Bernard Choi, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 53 days.

(21) Appl. No.: 19/011,057

(22) Filed: Jan. 6, 2025

(65) Prior Publication Data

US 2025/0134405 A1 May 1, 2025

Related U.S. Application Data

(60) Division of application No. 17/377,123, filed on Jul. 15, 2021, now Pat. No. 12,213,770, which is a (Continued)

(51) Int. Cl.
*A61B 5/026* (2006.01)
*A61B 5/00* (2006.01)
(Continued)

(52) U.S. Cl.
CPC .......... *A61B 5/0261* (2013.01); *A61B 5/0075* (2013.01); *A61B 5/14553* (2013.01); *A61B 5/6801* (2013.01)

(58) Field of Classification Search
CPC . A61B 5/0075; A61B 5/02028; A61B 5/0205; A61B 5/0261; A61B 5/14546;
(Continued)

(56) References Cited

U.S. PATENT DOCUMENTS

| | | |
|---|---|---|
| 4,709,702 A | 12/1987 | Sherwin |
| 6,251,587 B1 | 6/2001 | Sevigny et al. |

(Continued)

FOREIGN PATENT DOCUMENTS

| | | | | |
|---|---|---|---|---|
| CN | 113268142 A * | 8/2021 | ......... | A61B 5/14553 |
| DE | 101 53 360 A1 | 5/2003 | | |

(Continued)

OTHER PUBLICATIONS

Cuccia et al., "Quantitation and Mapping of Tissue Optical Properties Using Modulated Imaging", Journal of Biomedical Optics, vol. 14, No. 2, Mar./Apr. 2009, 13 pages.

(Continued)

*Primary Examiner* — Benjamin J Klein
*Assistant Examiner* — Vynn V Huh
(74) *Attorney, Agent, or Firm* — NGUYEN TARBET IP LAW

(57) ABSTRACT

A portable device for quantitative measurement of tissue autoregulation and neurovascular coupling via portable measurement of blood flow, oxygenation, metabolism, and/or EEG signals and methods for using said device. The device may comprise a body and a plurality of legs pivotably attached to the body. The plurality of legs may comprise at least one reference electrode leg and at least one measurement electrode leg for electrical measurement, and an optical
(Continued)

detection fiber leg and at least one optical source fiber leg for optical blood flow, oxygenation, and metabolism measurement. The present invention is additionally directed to a portable device for blood flow measurement and therapeutic photobiomodulation. The device may comprise a body and a plurality of legs. The plurality of legs may comprise at least one optical detection fiber leg and at least one optical source fiber leg, and at least one leg for therapeutic photobiomodulation.

5 Claims, 22 Drawing Sheets
(22 of 22 Drawing Sheet(s) Filed in Color)

Related U.S. Application Data continuation-in-part of application No. 16/985,113, filed on Aug. 4, 2020, now abandoned, which is a continuation-in-part of application No. PCT/US2020/035440, filed on May 29, 2020, and a continuation-in-part of application No. 16/837,478, filed on Apr. 1, 2020, now abandoned.

(60) Provisional application No. 63/032,491, filed on May 29, 2020, provisional application No. 62/854,215, filed on May 29, 2019, provisional application No. 62/827,668, filed on Apr. 1, 2019.

(51) Int. Cl.

| | |
|---|---|
| ***A61B 5/02*** | (2006.01) |
| ***A61B 5/0205*** | (2006.01) |
| ***A61B 5/145*** | (2006.01) |
| ***A61B 5/1455*** | (2006.01) |
| ***A61B 5/369*** | (2021.01) |
| ***A61N 1/04*** | (2006.01) |
| ***A61N 1/36*** | (2006.01) |
| ***A61N 2/00*** | (2006.01) |
| ***A61N 5/06*** | (2006.01) |

(58) Field of Classification Search
CPC ... A61B 5/14553; A61B 5/369; A61B 5/4836; A61B 5/4866; A61B 5/4875; A61B 5/6801; A61B 5/6814; A61B 5/6841; A61N 1/0456; A61N 1/0472; A61N 1/36025; A61N 2/006; A61N 2005/0626; A61N 2005/0644; A61N 5/0622
See application file for complete search history.

(56) References Cited

U.S. PATENT DOCUMENTS

| | | | |
|---|---|---|---|
| 6,280,393 | B1 | 8/2001 | Granger et al. |
| 6,466,816 | B2 | 10/2002 | Granger et al. |
| D739,122 | S | 9/2015 | Aimone et al. |
| 9,730,649 | B1 | 8/2017 | Jepsen |
| 10,009,644 | B2 | 6/2018 | Aimone et al. |
| 10,321,842 | B2 | 6/2019 | Garten et al. |
| 2002/0133087 | A1 | 9/2002 | Bayer et al. |
| 2003/0004557 | A1 | 1/2003 | Neuberger et al. |
| 2003/0050537 | A1 | 3/2003 | Wessel |
| 2004/0068199 | A1 | 4/2004 | Echauz et al. |
| 2005/0143589 | A1 | 6/2005 | Donoghue et al. |
| 2005/0228692 | A1 | 10/2005 | Hodgdon |
| 2006/0281983 | A1 | 12/2006 | Al-ali et al. |
| 2007/0191689 | A1 | 8/2007 | Elitok |
| 2008/0177572 | A1 | 7/2008 | Fuhrman et al. |
| 2008/0243022 | A1 | 10/2008 | Donnett et al. |
| 2008/0249430 | A1 | 10/2008 | Hiesiger et al. |
| 2009/0062685 | A1 | 3/2009 | Bergethon et al. |
| 2009/0118622 | A1 | 5/2009 | Durkin et al. |
| 2009/0181006 | A1 | 7/2009 | Dambinova |
| 2010/0241100 | A1 | 9/2010 | Blumenfeld et al. |
| 2011/0105912 | A1 | 5/2011 | Widman et al. |
| 2012/0143020 | A1 | 6/2012 | Bordoley et al. |
| 2013/0261183 | A1 | 10/2013 | Bhagat |
| 2014/0018649 | A1 | 1/2014 | Jespersen et al. |
| 2014/0088996 | A1 | 3/2014 | Damani |
| 2014/0316218 | A1 | 10/2014 | Purdon et al. |
| 2015/0051521 | A1 | 2/2015 | Woerlee et al. |
| 2015/0257674 | A1 | 9/2015 | Jordan et al. |
| 2016/0310049 | A1 | 10/2016 | Rowe et al. |
| 2016/0317385 | A1 | 11/2016 | Salcido et al. |
| 2016/0345880 | A1 | 12/2016 | Nakaji et al. |
| 2017/0135594 | A1 | 5/2017 | Hartings et al. |
| 2017/0224246 | A1 | 8/2017 | Jiang et al. |
| 2018/0044278 | A1 | 2/2018 | Bazan et al. |
| 2018/0085047 | A1 | 3/2018 | Hartings et al. |
| 2018/0103861 | A1 | 4/2018 | Sutin et al. |
| 2018/0246570 | A1 | 8/2018 | Coleman et al. |
| 2018/0308390 | A1 | 10/2018 | Moser et al. |
| 2019/0053721 | A1 | 2/2019 | Boas et al. |
| 2019/0113973 | A1 | 4/2019 | Coleman et al. |
| 2019/0117500 | A1 | 4/2019 | Shaw et al. |
| 2019/0159675 | A1 | 5/2019 | Sengupta et al. |
| 2019/0306438 | A1 | 10/2019 | Regan et al. |
| 2019/0306439 | A1 | 10/2019 | Morales Delgado et al. |
| 2019/0384392 | A1 | 12/2019 | Aimone et al. |
| 2020/0019243 | A1 | 1/2020 | Aimone et al. |
| 2020/0057075 | A1 | 2/2020 | Hinman et al. |
| 2020/0367761 | A1 | 11/2020 | Akbari et al. |

FOREIGN PATENT DOCUMENTS

| | | | | |
|---|---|---|---|---|
| EP | 3 020 333 A1 | 5/2016 | | |
| EP | 3857509 B1 * | 11/2023 | | ............ A61B 5/055 |
| WO | 2008/109699 A2 | 9/2008 | | |
| WO | 2016/164891 A1 | 10/2016 | | |
| WO | 2020/243658 A1 | 12/2020 | | |

OTHER PUBLICATIONS

Dreier et al., "Spreading Depolarization Is Not an Epiphenomenon But The Principal Mechanism of The Cytotoxic Edema In Various Gray Matter Structures of The Brain During Stroke", vol. 134, May 15, 2018, pp. 189-207.

EPO, "Extended European Search Report", issued in connection with European Patent Application No. 20813099.7 dated Sep. 27, 2023, 10 pages.

Kofman et al. "Dual-Wavelength Laser Speckle Imaging for Monitoring Brain Metabolic and Hemodynamic Response to Closed Head Traumatic Brain Injury in Mice", Journal of Biomedical Optics, vol. 20, No. 10, Oct. 2015, pp. 1-12.

Krachunov et al., "3D Printed Dry EEG Electrodes", Sensors, Journal, 1635, vol. 16, doi:10.3390/s16101635, Oct. 2016, pp. 1-18.

Lellouche et al., "Sudden Cardiac Arrest: ECG Repolarization After Resuscitation" Journal of Cardiovascular Electrophysiology, vol. 22, No. 2, 2011, pp. 131-136.

Mortberg et al., "Cerebral Metabolic Rate Of Oxygen (CMRO2) In Pig Brain Determined By PET After Resuscitation From Cardiac Arrest", vol. 80, No. 6, Jun. 1, 2009, pp. 701-706.

Puttgen et al., "Predicting Neurological Outcome Following Cardiac Arrest", Journal Of The Neurological Sciences, vol. 261, 2007, pp. 108-117.

Salvo et al. "A 3D Printed Dry Electrode For ECG/EEG Recording", Sensors and Actuators A: Physical, vol. 174, Dec. 8, 2011, pp. 96-102.

Sinha et al., "Monitoring the Brain After Cardiac Arrest: A New Era", Current Neurology and Neuroscience Reports, DOI 10.1007/s11910-017-0770-x, vol. 17, Article 62, Jul. 1, 2017, 11 pages.

Temple et al., "Predicting Neurological Outcome and Survival After Cardiac Arrest." Continuing Education in Anaesthesia Critical Care & Pain, vol. 12, Issue 6, Dec. 2012, pp. 283-287.

USPTO, "Advisory Action", issued in connection with U.S. Appl. No. 17/277,616 dated Oct. 10, 2024, 5 pages.

(56) References Cited

OTHER PUBLICATIONS

USPTO, "Final Office Action", issued in connection with U.S. Appl. No. 16/985,113 dated Mar. 15, 2021, 30 pages.
USPTO, "Final Office Action", issued in connection with U.S. Appl. No. 17/277,616 dated Aug. 14, 2024, 18 pages.
USPTO, "Non-Final Office Action", issued in connection with U.S. Appl. No. 16/985,113 dated Oct. 30, 2020, 22 pages.
USPTO, "Non-Final Office Action", issued in connection with U.S. Appl. No. 17/277,616 dated Dec. 11, 2024, 19 pages.
USPTO, "Non-Final Office Action", issued in connection with U.S. Appl. No. 17/277,616 dated Jan. 18, 2024, 19 pages.
USPTO, "Non-Final Office Action", issued in connection with U.S. Appl. No. 17/735,903 dated Feb. 27, 2025, 25 pages.
USPTO, "Notice of Allowance", issued in connection with U.S. Appl. No. 17/377,123 dated Sep. 29, 2024, 13 pages.
USPTO, "Notice of Allowance", issued in connection with U.S. Appl. No. 17/690,866 dated Jan. 24, 2025, 17 pages.
Wiebe et al., "Eeg-Pen for Medical Emergencies", Biomedical Engineering / Biomedizinische Technik, https://doi.org/10.1515/bmte.2002.47.s1a.308, Oct. 23, 2009, vol. 47, Issue s1a, 2 pages.
WIPO, "International Preliminary Report on Patentability" issued in connection with PCT Patent Application PCT/US2019/052486, dated Apr. 1, 2021, 6 pages.
WIPO, "International Preliminary Report on Patentability" issued in connection with PCT Patent Application PCT/US2020/053144, dated Apr. 7, 2022, 9 pages.
WIPO, "International Preliminary Report on Patentability" issued in connection with PCT Patent Application PCT/US2020/35440, dated Dec. 9, 2021, 8 pages.
WIPO, "International Preliminary Report on Patentability" issued in connection with PCT Patent Application PCT/US2022/37361, dated Jan. 25, 2024, 10 pages.
WIPO, "International Search Report and Written Opinion" issued in connection with PCT Patent Application PCT/US2019/052486, dated Nov. 19, 2019, 7 pages.
WIPO, "International Search Report and Written Opinion" issued in connection with PCT Patent Application PCT/US2020/053144, dated Mar. 9, 2021, 12 pages.
WIPO, "International Search Report and Written Opinion" issued in connection with PCT Patent Application PCT/US2020/35440, dated Oct. 15, 2020, 11 pages.
WIPO, "International Search Report and Written Opinion" issued in connection with PCT Patent Application PCT/US2022/37361, dated Oct. 13, 2022, 11 pages.
WIPO, "Invitation to Pay Additional Fees" issued in connection with PCT Patent Application PCT/US2020/053144, dated Nov. 16, 2020, 2 pages.
USPTO, "Final Office Action", issued in connection with U.S. Appl. No. 17/735,903 dated Jan. 26, 2026, 28 pages.

* cited by examiner

Data from measurement (1) is used to correct measurement (2) for the effect of the skull to yield quantitative brain properties from (2)

$CMRO_2$ = moles of oxygen consumed by the tissue per unit time ctHb = moles of hemoglobin that had its oxygen consumed by the tissue per unit volume → $CMRO_2$ = ctHb * (volume of tissue being oxygenated per unit time)

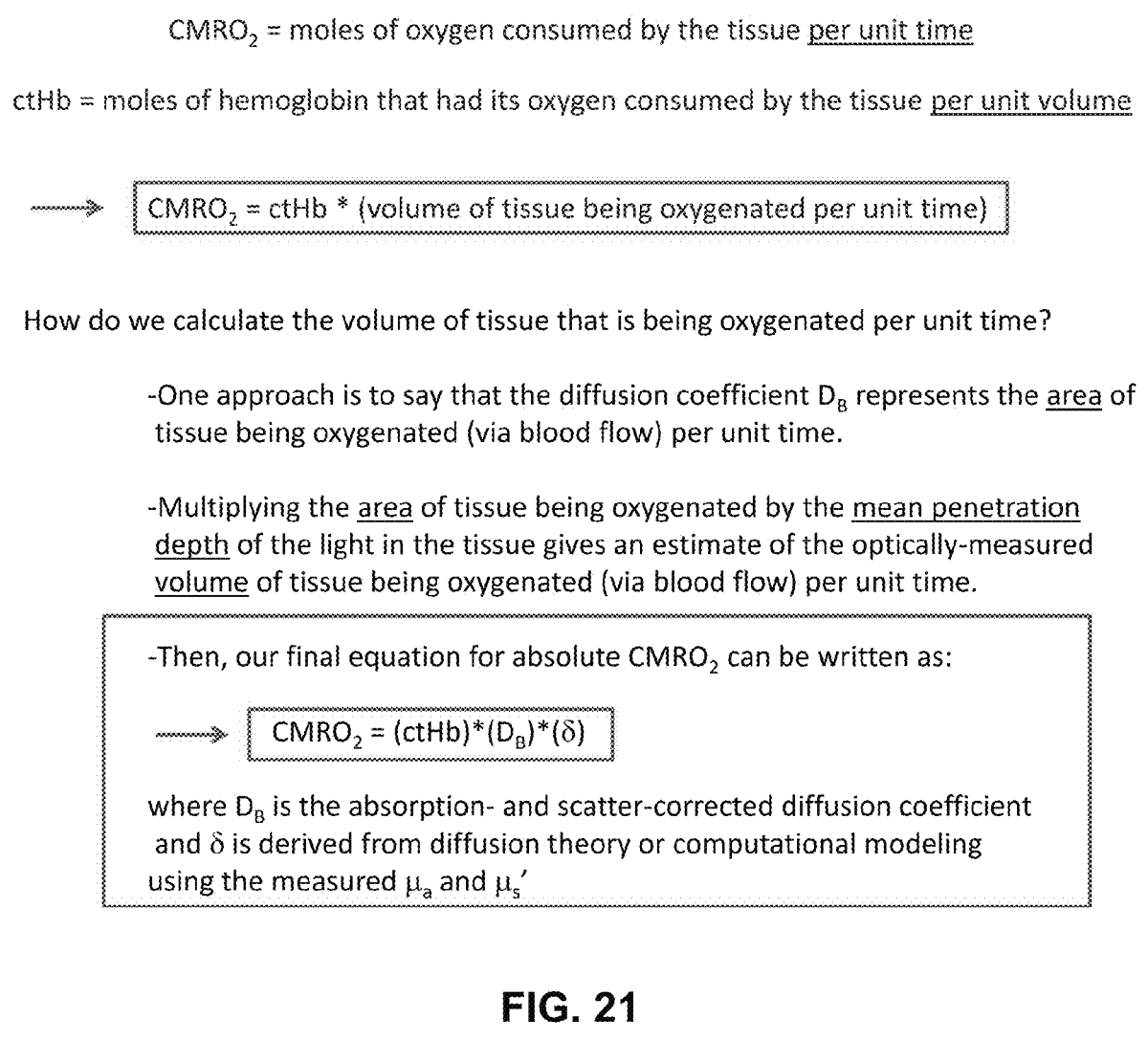

How do we calculate the volume of tissue that is being oxygenated per unit time?

-One approach is to say that the diffusion coefficient $D_B$ represents the area of tissue being oxygenated (via blood flow) per unit time.

-Multiplying the area of tissue being oxygenated by the mean penetration depth of the light in the tissue gives an estimate of the optically-measured volume of tissue being oxygenated (via blood flow) per unit time.

-Then, our final equation for absolute $CMRO_2$ can be written as:

→ $CMRO_2 = (ctHb)*(D_B)*(\delta)$ where $D_B$ is the absorption- and scatter-corrected diffusion coefficient and $\delta$ is derived from diffusion theory or computational modeling using the measured $\mu_a$ and $\mu_s'$

FIG. 21

Can fit for diffuse flow (Diffusion Coefficient) or directed flow speed

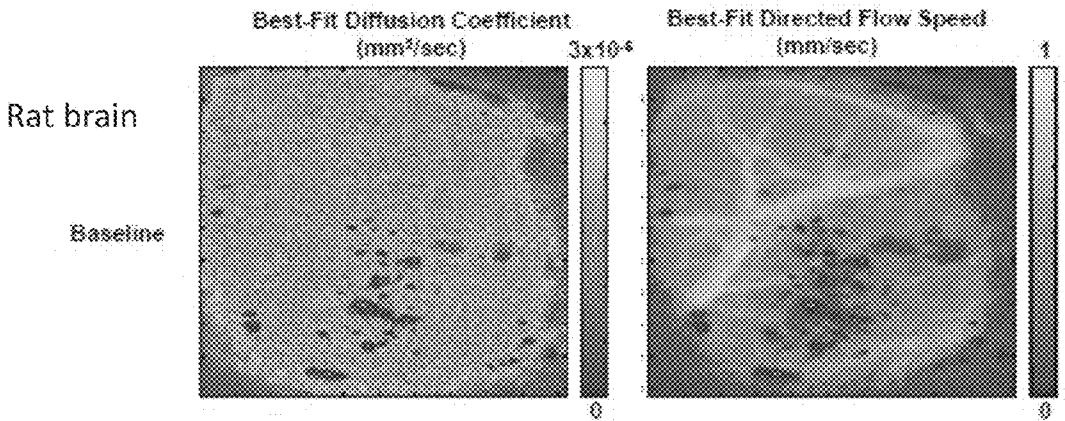

-If we use the directed flow speed instead of the diffusion coefficient, our final equation for absolute $CMRO_2$ can be written as:

$$CMRO_2 = (ctHb)*(v_c)*(\delta)^2$$

where $v_c$ is the absorption- and scatter-corrected directed flow speed and $\delta$ is derived from diffusion theory or computational modeling using the measured $\mu_a$ and $\mu_s'$ Note: you can also use a combination of the diffuse and directed flow terms to quantify flow and CMRO2 in absolute units

FIG. 27

Diffusion Regime:

where $\mu'_{eff} = (\mu_{eff}^2 + \mathbf{k}^2)^{1/2}$ $\mathbf{k = 2\pi f_x}$

The penetration depth of the light into the medium is given by $\delta'_{eff} = 1/\mu'_{eff}$ Therefore,
*the depth sensitivity of the measurement is a function of the spatial frequency used*

PORTABLE DEVICE FOR QUANTITATIVE MEASUREMENT OF TISSUE AUTOREGULATION AND NEUROVASCULAR COUPLING USING EEG, METABOLISM, AND BLOOD FLOW DIAGNOSTICS

CROSS-REFERENCES TO RELATED APPLICATIONS

This application is a divisional and claims benefit of U.S. application Ser. No. 17/377,123 filed Jul. 15, 2021, which is a continuation-in-part and claims benefit of U.S. application Ser. No. 16/985,113 filed Aug. 4, 2020, which is a continuation-in-part and claims benefit of U.S. application Ser. No. 16/837,478 filed Apr. 1, 2020, which is a non-provisional and claims benefit of U.S. Provisional Application No. 62/827,668 filed Apr. 1, 2019, the specifications of which are incorporated herein in their entirety by reference.

Also, U.S. application Ser. No. 16/985,113 is a non-provisional and claims benefit of U.S. Provisional Application No. 63/032,491 filed May 29, 2020, the specifications of which are incorporated herein in their entirety by reference.

Further, U.S. application Ser. No. 16/985,113 is a continuation-in-part and claims benefit of PCT Application No. PCT/US2020/035440 filed May 29, 2020, which claims benefit of U.S. Provisional Application No. 62/854,215 filed May 29, 2019, the specifications of which are incorporated herein in their entirety by reference.

STATEMENT REGARDING FEDERALLY SPONSORED RESEARCH OR DEVELOPMENT

This invention was made with government support under Grant No. DGE-1321846 awarded by the National Science Foundation and Grants No. P41EB015890, R21EB024793, TL1TR001415-01, KL2 TR001416, and UL1 TR001414 awarded by the National Institutes of Health. The government has certain rights in the invention.

FIELD OF THE INVENTION

The present invention is directed to the measurement of electrical (e.g., electroencephalography; EEG) signals, blood flow, and metabolism through the use of a portable device so as to quantitatively assess tissue autoregulation and neurovascular coupling. The present invention is additionally directed to photobiomodulation and electromagnetic modulation applied to cells and distributed by a portable device.

BACKGROUND OF THE INVENTION

The relative demand, supply, and consumption of oxygen in the various tissues of the body is an important component of tissue health. The flow of oxygenated blood to the tissue determines the supply of oxygen and the metabolic rate of the tissue determines the consumption of oxygen and drives the demand for oxygen. Autoregulation refers to the ability of the body to direct the appropriate amount of oxygenated blood to the different tissues to properly match each tissue's metabolic demand.

Characterizing autoregulation is crucial for understanding disorders such as focal and global ischemia (e.g., stroke, ischemic end-organs or limbs, cardiac arrest), all of which can feature mismatches between tissue oxygen demand and blood flow or tissue oxygen delivery and oxygen consumption. This also includes changes in autoregulation that can be induced by systemic inflammatory conditions, such as COVID-19, which can lead severe harm to end-organs due to inflammation, thrombosis, ischemia, and other emerging mechanisms that can lead to organ failure and possible death. Each organ has specific autoregulation means. For example, in the lung, hypoxia can lead to vasoconstriction to divert blood flow to more functional regions that can carry newly inhaled oxygen. On the other hand, in the brain, hypoxia can lead to vasodilation to improve blood flow in important brain cells that are highly sensitive to hypoxia, which can rapidly lead to neuronal cell death that can have catastrophic consequences.

Neurovascular coupling refers to the relationship between hemodynamic changes (e.g., changes in blood flow, oxygenation, and metabolism) and changes in cerebral electrical activity (e.g., EEG "bursts" and increases in EEG amplitude or entropy). Mismatches or prolonged delays between hemodynamic and cerebral electrical changes may be a sign of impaired autoregulation. Impaired autoregulation in any organ can lead to either ischemic damage resulting in cell death, inflammation, and organ failure or hyperperfusion damage, which can also result in inflammation and severe cellular and tissue injury. Typically, a body can autoregulate itself. However, during pathological conditions such as trauma, stroke, cardiac arrest, autonomic dysregulation can occur, leading to end-organ damage, morbidity, and possible mortality.

Clinically, it is advantageous to have a simultaneous read out for EEG, blood flow, tissue oxygenation, and tissue metabolism, because such a combination enables more accurate diagnosis of a neurological change or pathological condition and, in turn, rapid treatment. EEG allows for analysis of the brain electrical activity, which can identify seizures but also possibly raise concern for or highlight a multitude of other conditions, including a severely underperfused brain (e.g. stroke or cardiac arrest), post-ischemic injury, a drug overdose, neurodegenerative conditions, or other pathological or normal states of the brain, such as depth of medically-induced coma, stage of sleep or drowsiness, as well as cognitive performance measurements. While some aspects of EEG can be used to calculate a surrogate measure of blood flow, these are not standard of care and can often be inaccurate. Measurement of cerebral blood flow (CBF) is important to diagnose conditions such as a focal ischemic stroke, global ischemia, vasospasm, or other acute neurological conditions.

Currently, the more common techniques, especially in urgent situations, for measuring features of blood flow to the brain involve either angiography or ultrasonography. Angiography can be done by CT scan (i.e. CT Angiography), MRI (i.e. MR Angiography), or conventional (catheter-based) angiography. One of the benefits of obtaining both an EEG and a measure of CBF is to be able to more accurately distinguish between common neurological conditions such as a seizure or a post-ictal state (i.e. post-seizure condition) versus a stroke. To better illustrate this, one of the most common needs for a neurology consultation is for "altered mental status (AMS)", for which the cause may be a wide range of etiologies, including but not limited to a seizure, focal or global ischemia or stroke, traumatic brain injury, or toxic-metabolic derangements (e.g. drug overdose, liver or renal dysfunction, acid-base derangements, hypoxia, etc). The best way to distinguish between these is to obtain both an EEG and a blood flow test. During urgent consultations, there are several limitations to rapidly or instantaneously obtaining both an EEG and a blood flow test. An EEG typically requires a trained technician to conduct the test on a patient, which typically can take 20-45 minutes after the technician arrives at the patient's location. CT and MRI blood flow tests require transporting a patient to specific locations, which may be challenging if a patient is in a critically ill state (e.g. patients on a ventilator or with multisystem organ failure, including Covid-19 patients), while also having limited temporal resolution. Thus, typically, a diagnostic workup for AMS involves a detailed history, physical exam, neurological exam, serum or cerebrospinal fluid testing in a lab, and additional tests such as an EEG, CT scan of the head, MRI of the brain, transcranial Doppler ultrasound, and/or additional neurological tests.

BRIEF SUMMARY OF THE INVENTION

It is an objective of the present invention to provide devices and methods that allow for quantitative measurement of tissue autoregulation and neurovascular coupling via portable measurement of blood flow, oximetry, metabolism, and/or EEG signals, and for therapeutic photobiomodulation, and/or electromagnetic modulation as specified in the independent claims. Embodiments of the invention are given in the dependent claims. Embodiments of the present invention can be freely combined with each other if they are not mutually exclusive.

The benefits of having a simultaneous, rapid, and bedside read out for EEG and hemodynamics are innumerous and overcome several of the limitations listed above. Namely, such simultaneous read out provides a quick assessment enabling diagnosis of either abnormal brain electrical activity (e.g. seizures) vs hypoperfusion (e.g. focal or global stroke) vs hyperperfusion (e.g. malignant hypertension or brain hemorrhage), which in turn can allow for rapid treatments for the different conditions. Ultimately, this can lead to improved outcome for patients by preserving vital brain functions because every second and minute is critical to salvaging brain cells in a pathological state. In addition to EEG and blood flow, the present invention enables measurement of brain metabolism (via oximetry and cerebral metabolic rate of oxygen) as well as cerebral edema, changes in brain tissue morphology (via measurement of tissue scattering). Together, rapid access to this information allows a healthcare provider to rapidly diagnose and properly treat the patient.

An optical EEG pen may be used to treat a variety of conditions that have been shown to be amenable to transcranial light therapy (i.e. photobiomodulation), magnetic stimulation, or electrical stimulation. Each of these techniques may have potential treatment benefits for focal stroke, global ischemia, traumatic brain injury, neurodegenerative disorders, and psychiatric disorders, as well as cognitive performance enhancers. The optical EEG Pen may have embodiments that can include all of these therapeutic tools alongside the diagnostic tools described above. In combination, the diagnostic tools alongside the therapeutic tools can be applied to enable health care providers to make a rapid diagnosis as well as a rapid treatment using light, magnetic, or electrical stimulation with the option of making this automated in a closed-loop algorithm, including but not limited to brain-computer interface (BCI) systems and artificial intelligence approaches. These rapid treatments using the optical EEG Pen can also be combined with pharmacological or behavioral therapy to optimize combinations of multimodal treatment plans while providing precision-guided therapy tailored for each patient's individual needs that can also be rapidly modified in time.

The present invention features a portable device, either wired or wireless, for quantitative measurement of tissue autoregulation and neurovascular coupling via blood flow measurement, oximetry measurement, metabolism measurement, and simultaneous EEG monitoring. The device may comprise a body and a plurality of legs attached to the body by hinges. The plurality of legs may comprise a reference electrode leg and at least one measurement electrode leg for EEG measurement. The reference electrode leg may be used for calibration and the measurement electrode legs may be used to pick up EEG signals. The plurality of legs may further comprise at least one optical detection fiber leg and at least one optical source fiber leg for blood flow, oximetry, and metabolism measurement. The optical source fiber legs may be paired with a LED, laser diode, laser, or other light source to deliver light into tissue, and the optical detection fiber legs may be paired with a photodetector and receive backscattered light to produce blood flow, oximetry, and metabolism measurements. The device may additionally comprise legs for oximetry and metabolism measurements. The present invention may provide time-efficient diagnosis of an altered neurological state or pathological condition in a patient.

The present invention additionally features a portable device for blood flow, oximetry, and metabolism measurement, therapeutic photobiomodulation, and electromagnetic modulation. The device may comprise a body and a plurality of legs attached to the body by hinges or other type of component enabling maximal movement and flexibility. The plurality of legs may comprise at least one optical detection fiber leg and at least one optical source fiber leg for blood flow, oximetry, and metabolism measurement. The optical source fiber legs may be paired with a LED, laser diode, laser, or other light source to deliver light into tissue, and the optical detection fiber legs may be paired with a photodetector and receive backscattered light to produce blood flow, oximetry, and metabolism measurements. The plurality of legs may further comprise a leg paired with a photobiomodulation LED or other light source to propagate photobiomodulation light through tissue to promote cell and tissue repair. The present invention may provide time-efficient diagnosis of an altered neurological state or pathological condition in a patient as well as a time-efficient remedy for neurological issues or non-neurological issues through photobiomodulation.

One or more of the optical and/or electrical components of the system may be fabricated using MEMS, micro-opto-electromechanical systems (MOEMS), microphotonics, nanophotonics, and/or nanoelectronics.

The present invention may be applicable to the diagnosis and treatment of diseases such as COVID-19. Characterizing autoregulation is crucial for understanding disorders such as COVID-19 that include mismatches between tissue oxygen delivery, oxygen uptake, and oxygen consumption. For example, COVID-19 patients with severe respiratory complications may have sufficient oxygen delivered to the lung (e.g., via a ventilator), but the lung tissue is impaired in such a way that this oxygen cannot be efficiently taken up by the tissue (causing low tissue oxygen saturation) and the oxygen cannot be efficiently consumed by the tissue (causing low tissue metabolic rate of oxygen). Since the oxygen in these regions of the lung is not being efficiently utilized, the tissue may then undergo vasoconstriction to attempt to divert oxygenated blood from these locations to other parts of the body where oxygen may be consumed more efficiently. As a result, COVID-19 patients may exhibit significant mismatches between inspired oxygen, tissue oxygenation, tissue perfusion, and tissue oxygen metabolism. Disentangling these effects to inform the proper course of treatment for a given patient requires separation of perfusion, oxygenation, and metabolism into separate quantitative parameters in physiological units. Existing technologies typically measure one of these variables at a time (e.g., a blood flow monitor or an oximeter) and do not provide a combination of them in quantitative units to characterize autoregulation and pinpoint the source of the dysregulation so that it can be appropriately treated.

One of the unique and inventive technical features of the present invention is the non-invasive determination of absolute values of brain perfusion and metabolism. Without wishing to limit the invention to any theory or mechanism, it is believed that the technical feature of the present invention advantageously provides for quantification of cerebral autoregulation. None of the presently known prior references or work has the unique inventive technical feature of the present invention. Many previous devices have not been able to measure absolute values of brain perfusion and metabolism because they do not measure the combination of optical parameters that this proposed invention measures. In contrast, the present invention is able to measure absolute values of brain perfusion and metabolism by simultaneously obtaining blood flow data, oxygenated and deoxygenated hemoglobin data, and tissue scattering data at multiple wavelengths, modulation frequencies, source-detector separations, and/or photon propagation times. The invention then uses light transport models of this multivariate data to correct blood flow for tissue absorption and scattering, combine this blood flow data with oxygenation data to quantify the tissue metabolic rate of oxygen. Finally, the invention then uses ratios or other combinations of these hemodynamic and metabolic parameters to quantify tissue autoregulation. In addition, existing devices for quantifying perfusion and metabolism are often bulky and non-portable, have low temporal resolution, and/or use exogenous agents to enhance contrast, while our proposed invention is compact and portable, can monitor a patient with high temporal resolution, and relies only on endogenous contrast from components native to the tissue.

Another of the unique and inventive technical features of the present invention is the simultaneous measurement of EEG signals and blood flow, oxygenation, and metabolism employed in a portable device. Without wishing to limit the invention to any theory or mechanism, it is believed that the technical feature of the present invention advantageously provides for time-efficient diagnosis of an altered neurological state or pathological condition in a patient. None of the presently known prior references or work has the unique inventive technical feature of the present invention. Furthermore, the feature of the present invention is counterintuitive. The reason that it is counterintuitive is because the prior references teach away from the present invention. For example, when EEG, blood flow, and oximetry are currently used in clinical practice, their use often assumes that one measurement modality on its own will be able to help guide diagnosis, prognosis, and treatment. However, the current invention demonstrates that in many clinical cases, it is crucial to quantify the relationship between blood flow (cerebral and/or peripheral), tissue oxygenation (cerebral and/or peripheral), and electrical activity (in the brain and/or other organs such as the heart) to properly inform diagnosis, prognosis, and treatment. Such clinical cases include conditions where autoregulation is impaired, including, but not limited to, cardiac arrest, focal stroke, and COVID-19. In these and other cases, using only one of these measurement modalities by itself can often provide incomplete or even misleading information about the patient's physiological status. For example, if a patient has an acute focal motor weakness (e.g. hemiparesis) wherein a neurologist needs to "localize the lesion", the differential diagnosis may be stroke, seizure, post-ictal weakness, a spinal cord pathology, or a peripheral nerve abnormality. In this situation, if a simultaneous monitoring of EEG, blood flow, and oximetry is obtained, one can use the information obtained to more effectively make a diagnosis. For example, if the EEG signal, blood flow, and metabolism/oxygenation is decreased in the contralateral part of the brain (i.e. contralateral to the plegic arm/leg), it may signal an ischemic process such as an acute hemispheric stroke. However, if the EEG signal is diminished or shows some epileptiform discharges while the blood flow and oxygenation is normal, it may suggest a seizure or a post-ictal episode. If all the EEG, blood flow, and oxygenation in the brain is completely normal, it may suggest that lesion is below the brain and may include the spinal cord or peripheral nerve. Therefore, the current invention also suggests that using the combination of EEG, blood flow, and oximetry parameters (as well as other parameters described in this application) has the potential to provide surprisingly better diagnostic and prognostic power than any one of these parameters individually.

Additionally, prior systems require the use of large and non-portable equipment that may take 20-60 minutes to apply to a patient and receive a diagnosis, reducing the amount of time to act on a diagnosis. Furthermore, prior systems require a gel to be applied to a patient's head for electrodes or probes to work efficiently, further reducing the amount of time to act on a diagnosis while requiring additional materials that make the system even less portable. In contrast, the present invention is able to measure a patient's neurological condition in 2 minutes or less through the use of a small and portable device wherein the electrodes may be wet or dry.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWINGS

The patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 21 shows an embodiment where blood flow and oxygenation data are combined into a derivation of a different equation for absolute tissue metabolic rate of oxygen without the need to induce a "zero-flow" ischemic perturbation in the subject. By removing the need for the "zero-flow" condition, this embodiment shows significant additional clinical translational potential by enabling non-invasive measurement of tissue metabolism in physiological units without perturbing the subject. This embodiment involves multiplying the tissue deoxy-hemoglobin concentration (ctHb) by the volume of tissue being oxygenated per unit time to calculate tissue metabolic rate of oxygen. The volume of tissue oxygenated per unit time is determined by multiplying the Brownian diffusion coefficient Db (the area of tissue perfused per unit time) by the mean penetration depth of light in the tissue (determined from the measured absorption and scattering coefficients using a light transport model). The light transport model used in the penetration depth calculation was a diffusion model in this embodiment, but it could also be a Monte Carlo model, finite element model, or other type of analytical, semi-empirical, numerical, computational, or other type of model.

FIG. 27 shows an embodiment where the measured blood flow index can be corrected for tissue absorption and scattering (using a method similar to that in FIG. 13) to obtain a spatially-resolved map of either the Brownian diffusion coefficient Db or the directed-flow speed $v_c$. It is important to note that this method can also be used to map either or both of these coefficients as a function of time, and that these coefficients can be extracted simultaneously, along with weighting coefficients characterizing the relative contributions of each type of flow to the measured blood flow index. Types of flow in this model could include other flow equations besides those described here for diffuse and directed flow. FIG. 27 also shows an embodiment where the directed flow speed $v_c$ is used in a modified version of the absolute $CMRO_2$ equation described in FIG. 21. In this modified equation, Db is replaced with $v_c$ and the mean penetration depth of the light in tissue is squared to maintain units of micro-moles of oxygen per unit time for the calculated $CMRO_2$. As in FIG. 21, this $CMRO_2$ equation does not require a "zero-flow" ischemic perturbation to the tissue. This equation can also be modified further to include a combination of diffuse flow, directed flow, and other types of flow within the same model.

DETAILED DESCRIPTION OF THE INVENTION

Figure 1A:
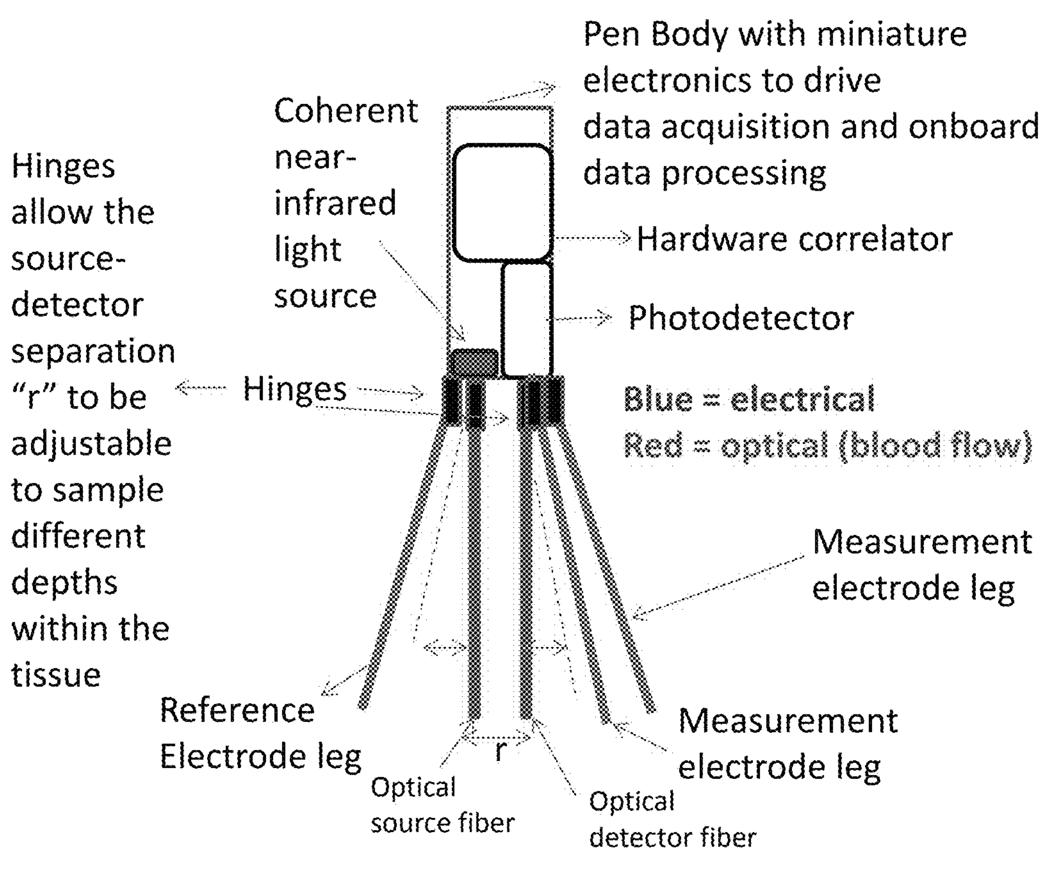
FIG. 1A shows a diagram of an embodiment of a portable EEG and blood flow measurement device.

As used herein, the term "intracranial measurement" refers to the measurement of tissue (such as brain tissue) inside the skull, by a probe which may be positioned outside the skull (i.e. the measurement is taken through the skull in a non-invasive manner).

In one embodiment, the present invention features a system for quantitative intracranial measurement of cerebral blood flow, oxygenation, metabolism, autoregulation, or a combination thereof. As a non-limiting example, the system may comprise: a device body; one or more light sources; one or more detectors, a microprocessor, and a memory component. The light sources and the detectors may extend from the device body and be configured to be positioned in proximity to a head of a subject. As a non-limiting example, the light sources and the detectors may extend from the device body so as to pass through the hair of the subject and contact the skin surface at a plurality of points in a measurement area. In another embodiment, the light sources and detectors may not extend from the device body, but instead be integrated within an end of the device body. In some embodiments, the microprocessor may be operatively connected to the one or more light sources, the one or more detectors, or a combination thereof. In further embodiments, the memory component may be operatively connected to the microprocessor, and the microprocessor may be capable of executing instructions held or stored in the memory component. According to preferred embodiments, one or more of the light sources may be configured to emit a coherent light signal. In selected embodiments, the system may be configured to detect and decouple one or more backscattered signals via the detectors. In one embodiment, the memory component may comprise instructions for decoupling components of the one or more backscattered signals. As a non-limiting example, the system may be configured to: differentiate between components of the one or more backscattered signals which are due to different layers of the head; measure or determine a dynamic perfusion metric; measure or determine a tissue absorption coefficient; measure or determine a tissue reduced scattering coefficient; calculate a value of an absolute perfusion metric, using the dynamic perfusion metric, the tissue absorption coefficient, and the tissue reduced scattering coefficient; calculate a value of an absolute metabolic metric, using the absolute perfusion metric, the tissue absorption coefficient, and the tissue reduced scattering coefficient; and calculate a quantitative value of cerebral autoregulation, using the absolute values of the perfusion metric and the metabolic metric. As another non-limiting example, the instructions for decoupling components of the one or more backscattered signals may comprise differentiating between components of the one or more backscattered signals that are due to different layers of the head; determining a dynamic perfusion metric using the one or more backscattered signals; determining a tissue absorption coefficient using the one or more backscattered signals; determining a tissue reduced scattering coefficient using the one or more backscattered signals; calculating a value of an absolute (or calibrated) perfusion metric, using the dynamic perfusion metric, the tissue absorption coefficient, and the tissue reduced scattering coefficient; calculating a value of an absolute metabolic metric, using the absolute perfusion metric, the tissue absorption coefficient, and the tissue reduced scattering coefficient; calculating a quantitative value of cerebral autoregulation, using the absolute values of the perfusion metric and the metabolic metric; or a combination thereof, thereby providing for quantitative intracranial measurement of cerebral blood flow, oxygenation, metabolism, and autoregulation As used herein, the terms "tissue absorption coefficient" and "tissue reduced scattering coefficient" may have both hemodynamic and non-hemodynamic components, and they may have tissue-based (e.g., brain, skin, muscle, heart, lung, etc.) and non-tissue-based (e.g., implantable or injectable tissue sensors such as implantable probes, nanoparticles, quantum dots, etc.) components.

In some embodiments, the instructions for decoupling the components of the one or more backscattered signals may be executed within the device. In other embodiments, the instructions for decoupling the components of the one or more backscattered signals may be executed external to the device. As a non-limiting example, any of the devices of the present invention may comprise a wired or wireless connection to an external processor, such that the data processing may be accomplished external to the device itself. As one non-limiting example, the system may include wireless transmitters and receivers to enable communication between the device and an external data processor. In some embodiments, processing of the data obtained by the device may be enhanced via a machine learning algorithm.

In one embodiment, the quantitative value of cerebral autoregulation may be calculated by dividing the quantitative value of the absolute perfusion metric (e.g. CBF) by the quantitative value of the absolute metabolic metric (e.g. $CMRO_2$). Alternatively, the quantitative value of cerebral autoregulation may be calculated by dividing the rate of change of an absolute or relative perfusion metric by the rate of change of an absolute or relative metabolic metric. Alternatively, the quantitative value of cerebral autoregulation may be calculated by creating a coordinate in a multidimensional space in which the "x-axis" is the absolute perfusion metric, the "y-axis" is the absolute metabolic metric, and other axes (dimensions) may include the rate of change in perfusion, the rate of change in metabolism, and the absolute values and/or rates of change in oxygenated hemoglobin concentration, deoxygenated hemoglobin concentration, total hemoglobin concentration, tissue oxygenation, tissue scattering coefficient, and tissue water content. Additionally, these autoregulation metrics are not limited to the brain and can be applied to other organs so long as a perfusion metric and metabolic metric is obtainable. Moreover, in all organs, including but not limited to the brain, a perturbation (e.g. pharmacologic intervention or modification of the oxygen or carbon dioxide level) can be introduced to determine the change in autoregulation metrics at baseline and during a perturbation to improve assessment of autoregulation or lack thereof.

In some embodiments, the system may additionally include one or more electroencephalography (EEG) electrodes, which may extend from the device body and may allow for co-localized EEG monitoring. As a non-limiting example, the system may be configured to detect an EEG signal and evaluate neurovascular coupling. Alternatively, detection of the EEG signal may allow for quantification of cerebral electrical activity via parameters including, but not limited to, root-mean-squared (RMS) intensity, information quantity (IQ) and other entropy-based measures, burst frequency, coherence, and phase-amplitude coupling, either in a specific sub-band (or a ratio of two sub-bands) or over a wider range of frequencies, using either values at individual time points or changes in these values over a period of time. A highly robust EEG signal, especially with certain quantification metrics, can signify a highly activate brain, which in turn would be expected to have a high blood flow, suggesting adequate neurovascular coupling. On the other hand, if neural activity and blood flow are not matched accordingly, this may suggest neurovascular decoupling and the possibility of ischemia or overperfusion, both of which can be pathologic.

In one embodiment the system may continuously calculate the quantitative value of the autoregulation metric in real time. As used herein, the term "real time" refers to a very short time delay (e.g., from less than a second to several minutes, depending on the embodiment) between data acquisition and display of measured parameters. This may advantageously allow for rapid monitoring, because measuring these types of parameters in absolute quantitative units enables characterization of the tissue in a very short period of time, without need for a perturbation "challenge" that would require more time to administer and more stress to the patient. Immediate assessment of a patient by a first-responder being called for a medical emergency (e.g. stroke, trauma, hemorrhage, cardiac arrest, etc.) would highly benefit from real-time monitoring to enable health-care providers to make an accurate diagnosis and thereby mobilize an accurate and rapid treatment. This may also advantageously allow for real-time feedback to inform clinical treatment by monitoring the effects of a clinical intervention (e.g., raising or lowering blood pressure, administering oxygen) during and immediately after it is performed. In preferred embodiments, the system is non-invasive, detects an intrinsic optical signal, and does not require any exogenous analyte or contrast agent. Here, an intrinsic signal is defined as a signal that is inherent to the tissue.

According to one embodiment, the present invention features a device for quantitative intracranial measurement of a brain metric. As a non-limiting example, the device may comprise: a device body; one or more light sources; and one or more detectors. The device may additionally comprise an operatively connected microprocessor and an operatively connected memory component capable of executing instructions held or stored in the memory component. In some embodiments the light sources and the detectors may extend from the device body and be positioned in proximity to a head of a subject. In some embodiments, the light sources may be configured to emit a coherent light signal (either spatially or temporally coherent) and a modulated light signal (including, but not limited to, intensity/amplitude modulation, phase modulation, frequency modulation, temporal modulation, and/or spatial modulation). The coherent light signal may allow for measurement of a dynamic perfusion metric and the modulated light signal may allow for measurement of a tissue absorption metric and a tissue scattering metric. The detectors may be configured to detect one or more backscattered light signals. In a preferred embodiment, the backscattered light signals may allow for determination of an absolute value of the brain metric using the dynamic perfusion metric, the tissue absorption metric and the tissue scattering metric. This determination may be accomplished by the execution of decoupling instructions which are held in the memory component. All of these metrics can change over time and these changes can be monitored by this invention.

Non-limiting examples of dynamic perfusion metrics include speckle flow index (SFI), and blood flow index (BFI). Non-limiting examples of calibrated perfusion metrics include Brownian diffusion coefficient (Db), directed flow speed ($v_c$), and cerebral blood flow (CBF). Non-limiting examples of tissue absorption metrics include tissue absorption coefficient at different wavelengths, oxygenated hemoglobin concentration, deoxygenated hemoglobin concentration, and total hemoglobin concentration. Non-limiting examples of tissue scattering metrics include tissue scattering coefficient and reduced scattering coefficient at different wavelengths, scattering amplitude, and scattering slope.

In some embodiments, the device may comprise two or more detectors with different source-detector separations, and the different source-detector separations may allow the device to distinguish between signals from different depths, for example, between signals from the scalp/skull and signals from the brain. Alternatively, the device may distinguish between signals from the skull and signals from the brain by using (either individually or in combination) different wavelengths, different modulation frequencies, different angles of the source and detector fibers, or time-gating approaches. Location of the source and detector on particular areas of the skull may also enable optimization of signal detection. For example, the temporal bone is thinner. Further, the orbital socket, including the eye and, in particular the retina, can also enable better detection of an optical signal that can provide direct or indirect data about the brain.

In one embodiment, the brain metric may be indicative of brain perfusion, oxygenation, metabolism, or cerebral edema. As a non-limiting example, the brain metric may comprise cerebral metabolic rate of oxygen ($CMRO_2$), cerebral blood flow (CBF), tissue concentration of deoxy-hemoglobin (ctHb), tissue concentration of oxygenated hemoglobin ($ctHbO_2$), tissue oxygenation ($StO_2$) or a combination thereof. In further embodiments, the dynamic perfusion metric, a tissue absorption metric, or a tissue scattering metric may provide information on neuronal injury, edema, sickle cell disease, depolarization, seizure activity, pharmacologic changes, ischemia, hypoxia, metabolic injury, impaired autoregulation, or a combination thereof.

The light sources of the present invention may emit one or more light signals. As non-limiting examples, the light signals may include coherent light, modulated light, light at multiple wavelengths, light delivered at different spatial locations, light delivered at different angles relative to the tissue, light delivered to the tissue with different spatial or temporal "gates" relative to its detection, or a combination thereof. The coherent light signal and the modulated light signal may comprise a single coherent modulated light signal or may comprise separate light signals. In one embodiment, the device may additionally comprise an electroencephalography (EEG) electrode for co-localized EEG monitoring. In some embodiments, concurrent EEG monitoring and optical monitoring may allow for measurement of a time offset between corresponding neurologic and hemodynamic activity. This offset may indicate inefficiencies and/or delays in neurovascular coupling and could potentially be used to quantify disruption in cerebral autoregulation. This may also help in determination of cause and effect. For example, a neuronal dysfunction (e.g. stroke or seizure) may lead to subsequent vascular changes (e.g. hyperperfusion), or a vascular change (e.g. thrombosis) can lead to neuronal dysfunction (e.g. stroke). Thus, offset time can be very helpful for a clinician in the process of a diagnostic workup so that the correct treatment can be provided.

The device may additionally comprise a therapeutic probe for to administration of a colocalized therapy. As a non-limiting example, the therapy may comprise colocalized transcranial light therapy, photobiomodulation, magnetic stimulation, electrical stimulation, or another therapy. In some embodiments, determination of the absolute value of the brain metric, or a change in the value of the brain metric, may guide the therapy in real time.

In some embodiments, the device may use diffuse correlation spectroscopy (DCS), frequency-domain diffuse optical spectroscopy (FD-DOS), or a combination thereof, at one or more wavelengths in a range comprising the visible, near-infrared (NIR), and short-wave infrared (SWIR) regimes. DCS may be used to quantify blood flow. FD-DOS may be used to separate tissue absorption and scattering coefficients by using modulated light.

According to one embodiment, the sources and detectors may be attached to the device body via a plurality of legs or extendable support fibers which may be retracted into the device body. Legs may also be more flexible (e.g. made of a pliable material, such as rubber) or contain flexible optical fibers made of a pliable material that can be extended outward to reach multiple different positions on a patient and then retracted back into the body of the device following completion of the measurement. Additionally, the legs may simply be wires that are pulled out (e.g. unrolled from a rotating device) and extended from the hinge region, locked in length to attach to the target tissue site by sticky material to obtain the signal and then retracted back to its original position when data acquisition and analysis is complete. The latter would also preclude having to hold the device by hand to ensure stability of the data acquisition and thereby allowing the possibility that the device can be clipped onto a patient's clothes or rested next to them to allow for more prolonged data acquisition if desired. The extendable support fibers may be flexible or rigid, and may be designed to set a wide range of different spacings (using retractable flexible fibers or flexible legs) between the various sources and detectors and an angle between each source and detector and the surface of the head. In one embodiment, two or more of the detectors may have different source-detector separations. Without wishing to limit the present invention to any particular theory or mechanism, this may allow for differentiation of signals due to different tissues or materials at different depths. In some embodiments, the various source-detector separations may be measured by a distance sensor, a camera, a ruler, or by a patch which guides placement of the sources and detectors.

In an alternative embodiment, the present invention may feature a device for quantitative subdermal measurement of a tissue metric. As a non-limiting example, the device may comprise: a device body; one or more light sources; and one or more detectors. The device may additionally comprise a microprocessor, operatively connected to the light sources and the detectors, and a memory component, operatively connected to the microprocessor such that the microprocessor is capable of executing instructions held in the memory component. The light sources and detectors may extend from the device body so as to be positioned in proximity to a body surface of a subject, for example, on a limb or on a torso, or within an endoscope, over the position of an organ of interest. This may also include assessment of the circulatory system (e.g. arteries or veins) in various regions of the body to assess for blood flow and regional metabolism. In an alternative embodiment, the device may be an endoscopic device which is configured to position the sources and detectors within the body. In one preferred embodiment the light sources may be configured to emit a coherent light signal and a modulated light signal. In another preferred embodiment, the detectors may be configured to detect one or more backscattered light signals.

In some embodiments, the modulated light signal may allow for decoupling of a plurality of components of the backscattered light signals. This decoupling may be accomplished via the microprocessor's execution decoupling instructions which are held in the memory component. As a non-limiting example, the modulated light may enable decoupling of tissue absorption and scattering coefficients. In one embodiment, the components may comprise: a tissue absorption component; a tissue scattering component; and a dynamic scattering flow component. In further embodiments, the decoupled components of the backscattered light signals may allow for determination of an absolute value of the tissue metric. The absolute value of the tissue metric may provide information on the perfusion or metabolism of an organ, or may be indicative of tissue autoregulation. In one embodiment, the device may allow for comparative analysis of the autoregulation of two or more body parts. For example, on COVID-19 patients, the device could measure the autoregulation of the lung versus the brain to quantify the degree to which respiratory impairment is affecting the brain. This is important because in COVID-19, there can be "silent hypoxia", wherein the respiratory impairment may lead to low system oxygen levels while the brain is compensating adequately. This may argue against maximal oxygen therapy in the lung by mechanical ventilation, which can cause ventilator-induced lung injury. Thus, understanding the coupling and decoupling of flow-metabolism dynamics between organs can help a clinician tailor the medical therapy for a particular patient's condition in a more precision guided manner without using a suboptimal "one-size-fits-all" approach.

In another embodiment, the present invention may feature a portable device for measuring EEG and blood flow simultaneously. As a non-limiting example, the device may include: a body; a signal processing component; a plurality of legs comprising: at least one reference electrode leg, at least one measurement electrode leg, at least one leg comprising an optical source fiber, and at least one leg comprising an optical detection fiber, wherein each leg is pivotably attached to the body; a light source disposed within the body attached to each leg comprising an optical source fiber; a photodetector disposed within the body attached to each leg comprising an optical detection fiber; and a hardware or software correlator disposed within the body communicatively coupled to the photodetector.

In some embodiments, the device may include a signal processing component that analyzes a signal received by a measurement electrode. In other embodiments, the device may include a signal processing component that analyzes a signal generated by the light source and received by the photodetector. In still other embodiments, the device may include one or more components are wirelessly, operatively connected to a display, where the display shows the data obtained from the components. In some embodiments, the optical detection fiber may comprise an optical or electronic filter that allows for separating coherent light from incoherent light. In some other embodiments, the device may include an on-board or off-board correlator for signal processing and analysis of pulsatile components in cerebral blood flow or cardiovascular blood flow.

According to one embodiment, the device may additionally comprise: one or more oximetry optical source fibers; one or more oximetry optical detection fibers; one or more light sources connected to the oximetry optical source fibers; and one or more oximetry photodetectors connected to one or more oximetry optical detection fibers. In some embodiments, the first light source may deliver light at a lower-energy range and the other light sources deliver light at higher-energy ranges. In one embodiment, the optical source fibers may be disposed in a single leg. In another embodiment, the optical detection fibers may be capable of collecting electrical signals and converting them to optical signals using an electrical-optical transducer. In still another embodiment, the oximetry optical detection fibers may be connected to one or more optical-electrical transducers. In yet another embodiment, the device may feature an adjustable clamping mechanism for retracting and extracting optical or electronic fibers.

In one embodiment, the present invention may feature a portable device for therapeutic photobiomodulation and blood flow, oximetry, and/or electrical activity (e.g. from brain or other tissue) measurement. As a non-limiting example, the device may comprise: a body; a plurality of legs comprising: one or more legs having one or more optical source fibers, wherein each leg is pivotably connected to the body by a hinge. one or more legs having one or more optical detection fibers, one or more photobiomodulation light sources connected to one or more optical source fibers; one or more non-photobiomodulation light sources connected to one or more optical source fibers; and one or more photodetectors connected to one or more detection fibers. In some embodiments, the photobiomodulation light sources may produce light capable of therapeutic photobiomodulation of biological embodiments, the non-photobiomodulation light sources may produce light for blood flow, oximetry, and/or electrical activity (e.g. of brain or other tissue) measurements. In still other embodiments, the detection fibers may receive backscattered light produced by the optical source fibers.

In one embodiment, the photobiomodulation light sources may produce a wide range or specific range of light including but not limited to visible light, near-infrared light, short-wave infrared light, or infrared light. In another embodiment, the photobiomodulation light sources may promote a variety of perfusion and metabolism changes including but not limited to increased cellular metabolism of oxygen, generation of ATP, vasodilation, and enhanced perfusion of tissue. In still another embodiment, the changes produced by the photobiomodulation light sources may be monitored using methods including but not limited to real time detection or delayed detection by the photodetector.

In some embodiments, the device may have additional legs for delivering an electrical current and/or a magnetic field produced by a plurality of microelectronics, including but not limited to MEMS, disposed within the body for therapeutic electromagnetic cell and tissue modulation. The electrical current and/or magnetic field may promote changes including but not limited to perfusion, metabolism, and electrical activity. In some embodiments, the changes produced by the electrical current and/or magnetic field may be monitored using methods including but not limited to real time analysis by the photodetector and associated electronics.

According to some embodiments, the present invention features a device with capabilities for optical and electrical (i.e. EEG) monitoring. In other embodiments, the present invention features a device with only optical monitoring capabilities. In still other embodiments, the present invention features a device with only electrical monitoring capabilities. While for some situations, it may be desirable to have both optical and electrical data, for many situations, electrical data alone may be sufficient. For example, the electrical monitoring herein is capable of measuring an evoked potential wherein the stimulus used to evoke a potential may also be provided by the said device or another device. Here, an evoked potential may include, but is not limited to, a visual evoked potential, somatosensory evoked potential, auditory evoked potential, steady-state evoked potential, laser evoked potential, motor evoked potential, evoked compound motor action potential or sensory nerve action potential as seen in nerve conduction studies. As such, this optical EEG pen may be used to rapidly conduct an evoked potential without the need for a bulky equipment and significant preparation time. For example, for each type of evoked potential measurement, the optical EEG pen itself may be able to provide the stimulus (e.g. light pattern for a visual evoked potential, specific frequency and type of sound for an auditory evoked potential, an electrical impulse or shock to a peripheral nerve for a somatosensory evoked potential, etc.). These evoked potentials may be induced by an extension (wired or wirelessly) of the optical EEG pen so that the main body of the optical EEG pen itself may still be touching or attached to the head so that the EEG signal and evoked potential change in the brain can be measured. If necessary, the evoked potential can utilize the optical portions of the optical EEG pen also (e.g. light to conduct a visual evoked potential). However, only the electrical components of the optical EEG pen may be utilized to either record the evoked potential induced by a separate device or the optical EEG pen itself (e.g. an electrical impulse). Similarly, either by itself or with additional components, the optical EEG pen may also allow for an event-related potential to be measured. As such, by allowing for evoked potentials or event-related potentials to be tested, the optical EEG pen's electrical data alone may enable significant diagnostic workup and interrogation of the nervous system, including lesions along the sensory or motor pathways, including peripheral nerves, the spinal cord, brainstem, subcortex, or the cortex. Such lesions may be induced through trauma, surgical procedures, drug-induced dysfunction, or insults. This can also be used to assess for neuroplasticity and monitoring of response to treatments geared towards improvement of a pathway. This may also be used for intraoperative monitoring of the neuroaxis. Current systems that may allow for monitoring and testing are bulky and take time whereas the optical EEG pen will enable rapid analysis of the neuroaxis. Moreover, the optical, electromagnetic, and photobiomodulation aspects of the optical EEG pen can enable for far more diagnostic and therapeutic measures to be conducted. For example, if a lesion is localized in the neuroaxis, treatment may be implemented using these other features of the optical EEG pen described elsewhere here.

Referring now to FIG. 1A, the present invention may feature a portable device for measuring EEG and blood flow simultaneously. The device may comprise a body and a signal processing component. The device may further comprise a plurality of legs comprising one or more reference electrode legs, one or more measurement electrode legs, at least one leg comprising an optical source fiber, and at least one leg comprising an optical detection fiber. Each leg may be pivotably attached to the body by a hinge or another type of pivotable attachment. The device may further comprise a light source, which may include but is not limited to visible light (e.g. 400-750 nm), near-infrared light (750-1000 nm), short-wave infrared light (approximately 1000-2000 nm) disposed within the body at the hinge of each optical source fiber leg, a photodetector disposed within the body at the hinge of each optical detection fiber leg, and a hardware or software correlator disposed within the body communicatively coupled to the photodetector. In some embodiments, the near-infrared light source may additionally be a coherent light source. The signal processing component may analyze a signal received by a measurement electrode and may analyze a signal generated by the coherent near-infrared light source and received by the photodetector. FIG. 1A shows an embodiment of the "Optical EEG pen" invention that includes technology for simultaneous measurement of EEG activity and cerebral blood flow. The pen body may contain electronic components for receiving the detected electrical signal from the electrodes. The pen body may also include a coherent light source in the near-infrared range (or visual or short-wave infrared range) that is directed onto the tissue and one or more photodetectors for detecting the optical signal that returns to the surface to measure blood flow. In some embodiments, five or more legs are connected to the pen body via hinges (or another attachment) to allow flexibility in their positioning. Two or more legs may contain measurement (recording) electrodes, one or more legs may contain a reference electrode, one or more legs may contain an optical fiber for delivering coherent light to the tissue, and one or more legs may contain an optical fiber for detecting the light that returned to the surface after delivery of the light by the fiber and propagation of the light through the tissue. In other embodiments, the pen body may be replaced with a clip version with retractable fibers or electrodes that do not need to be held by the hand but rather attached to a surface. In yet other embodiments, the device can be used to obtain measurements from multiple different regions of the brain or bodily tissue to obtain a map of the endpoints measured, including but not limited to a 3-dimensional representation of the brain, heart, lungs, other internal organs, limbs, circulatory system (e.g. arteries or veins), and/or other body parts. As such, this invention need not be limited to a pen body but rather other embodiments of a portable device that are wireless or wired.

Figure 1B:
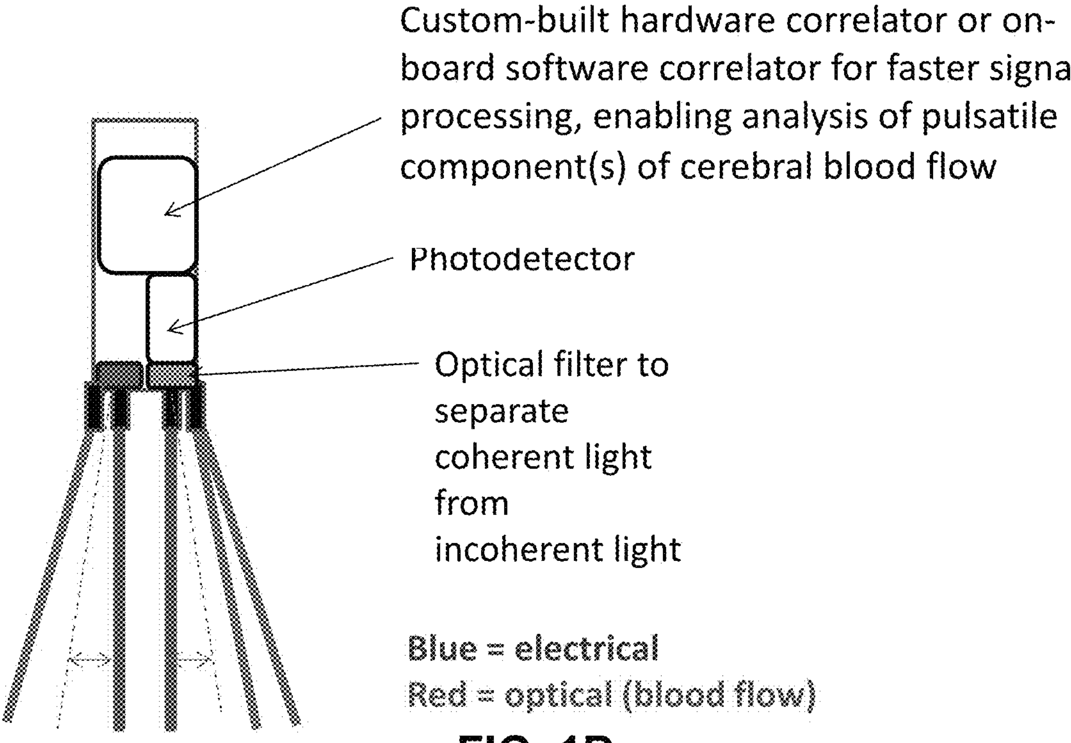
FIG. 1B shows a diagram of an embodiment of a portable EEG and blood flow measurement device comprising an optical filter and custom correlator.

Referring now to FIG. 1B, the optical detection fiber may comprise an optical filter (e.g., a spectral filter) for separating coherent light from incoherent light and an on-board or off-board software correlator for signal processing and analysis of pulsatile components in cerebral blood flow. FIG. 1B shows an embodiment of the invention that enables faster on-board or off-board data processing by using a custom-built hardware correlator or software correlator for faster signal processing, enabling real-time on-board or off-board acquisition and analysis of data related to pulsatile components of cerebral hemodynamics.

Figure 1C:
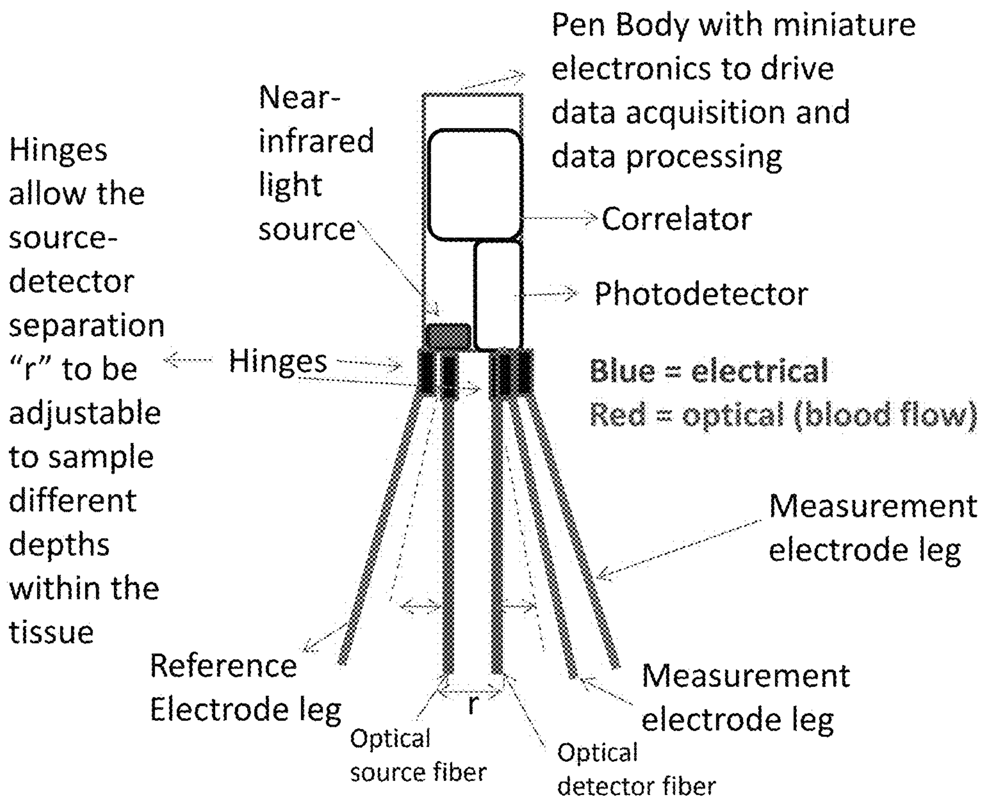
FIG. 1C shows an additional embodiment where the correlator could be either a hardware or a software correlator and the data processing can either be on-board or off-board, and the analysis of the data may be done in real-time.

FIG. 1C shows an additional embodiment where the correlator could be either a hardware or a software correlator and the data processing can either be on-board or off-board.

Figure 1D:
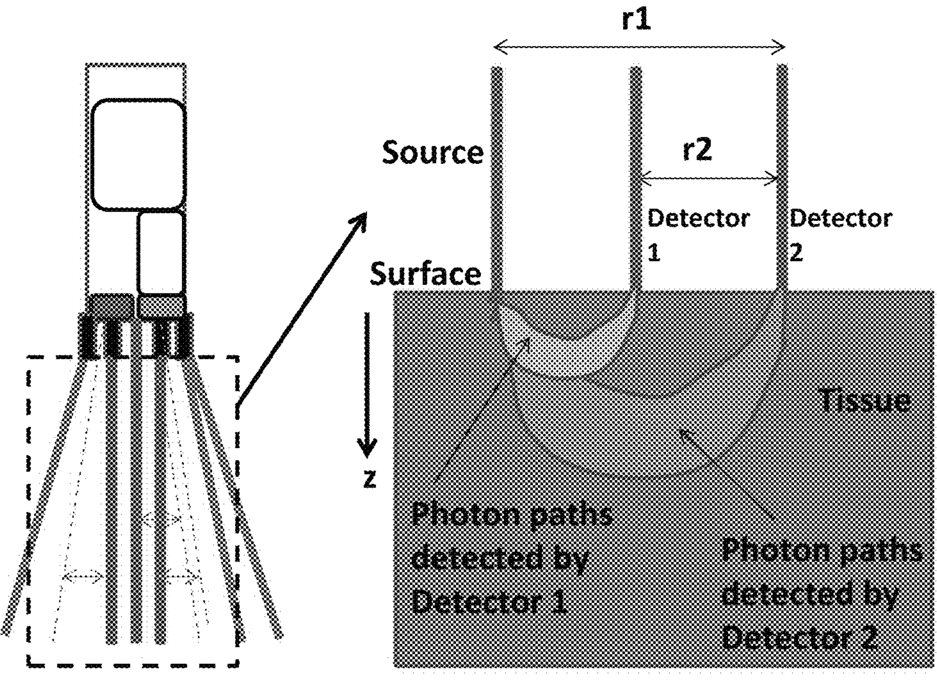
FIG. 1D shows an additional embodiment where multiple detector fibers can be used to detect optical signals from the tissue. The use of multiple detector fibers allows for multiple source-detector separations (e.g., r1 and r2), which allows the device to probe different depths (z) beneath the surface of the tissue to interrogate different regions of the brain or other bodily tissue and/or better separate the signal from the brain or other bodily tissue from that of the skin, subcutaneous tissue, and/or bone. This embodiment can also be applied to all other embodiments described in this invention.

FIG. 1D shows an additional embodiment where multiple detector fibers can be used to detect optical signals from the tissue. The use of multiple detector fibers allows for multiple source-detector separations (e.g., r1 and r2), which allow the device to probe different depths (z) beneath the surface of the tissue to interrogate different regions of the brain or other bodily tissue and/or better separate the signal from the brain or other bodily tissue from that of the skin, subcutaneous tissue, and/or bone. This embodiment can also be applied to all other embodiments described in this invention.

Figure 2:
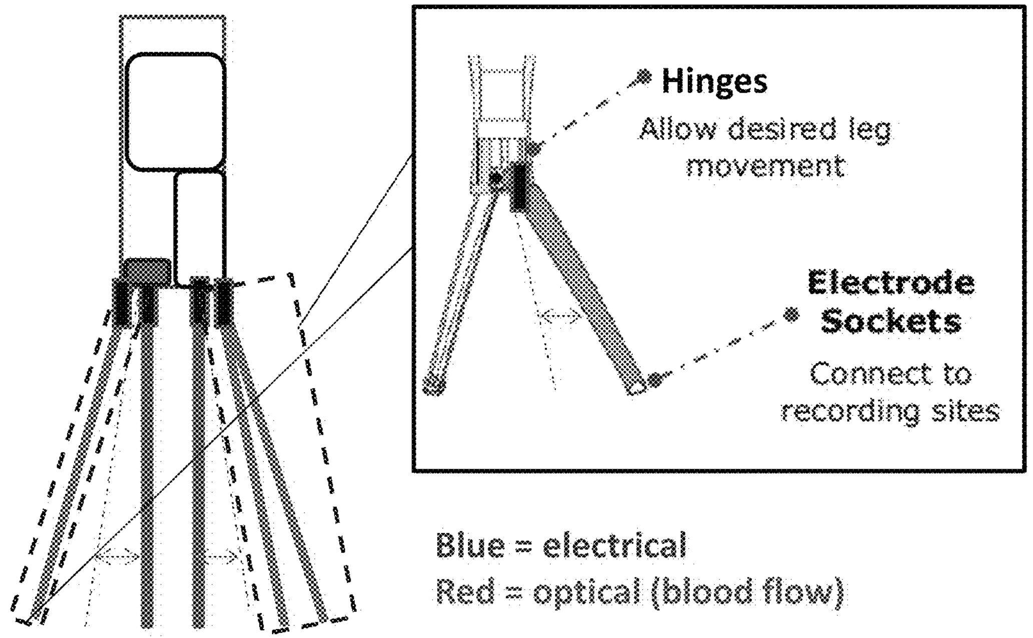
FIG. 2 shows a diagram of a leg of a portable EEG and blood flow measurement device.

Referring now to FIG. 2 the reference electrode leg and each measurement electrode leg may further comprise an electrode socket for connecting to recording sites. FIG. 2 shows an embodiment of the invention that shows how the hinges or a related component connect the legs to the body, as well as showing how the tips of three of the legs contain electrode sockets that contact recording sites on the head to record EEG signals from the brain. Of note, signal detection with this invention need not be limited to detection of brain signals. Rather, they can apply to the detection and analysis of cardiac signals (e.g. electrocardiogram; ECG) or muscle (e.g. electromyogram) also if applied to different regions of the body with appropriate signal filtering, calibration, referencing, and analysis. This can be extremely helpful during a medical emergency such as a cardiac arrest wherein very fast deployment of the optical EEG pen onto the chest or other body part to enable ultra-rapid diagnosis of the cardiac rhythm much faster than conventional methods can be life-saving (i.e. shockable versus non-shockable rhythm).

The electrode socket may comprise a base having a first side and a second side, a joint disposed on the base at the first side and pivotably connected to the leg, a plurality of extrusions disposed on the second side, and a recording site disposed on each extrusion of the plurality of extrusions. The recording site may be coated in Ag or AgCl or another type of material that can maximize detection of electrical signals while minimizing electrical noise. In one embodiment of the invention, the electrode sockets at the tips of the three EEG legs may be composed of small extrusions that serve as recording sites. The recording sites are coated with Ag/AgCl or other type of surface to enhance conductivity of detected electrical signals and allow the possibility of AC and DC signals to be measured. The electrodes can be of the wet or dry type depending on the situation and the target organ (e.g. brain EEG signal or heart ECG signal) being measured that will optimize usage, signal detection, indication of need, and cost based on advantages and disadvantages of different types of electrodes.

Figure 3:
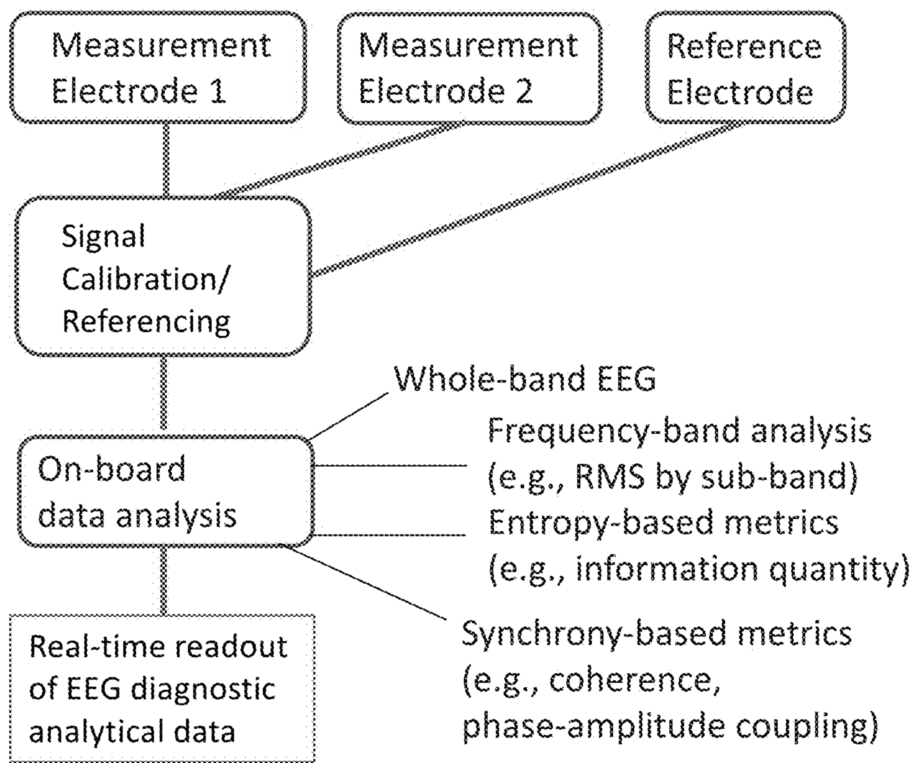
FIG. 3 shows a flow chart of EEG measurement instructions of a signal processing component.

FIG. 3 shows an embodiment of the signal processing component of the EEG portion of the invention. At each time point, the detected signals from the two measurement electrodes and the reference electrode are filtered to remove noise or to narrow the signal down to the desired range (e.g. for the clinical indication), calibrated by using the signal from the reference electrode (via common-average referencing or a similar technique). Next, the processed signals are analyzed on-board or off-board via microelectronics, including but not limited to MEMS or nanoelectronics, via methods including but not limited to whole-band EEG, frequency-based EEG (e.g., frequency sub-band raw signal or RMS and amplitude-based measurements by frequency sub-band), entropy-based metrics (e.g., information quantity), synchrony-based metrics (e.g., coherence, phase-amplitude coupling), and seizure detection algorithms. Then, the EEG signal and parameters from the data analysis are read out in real time. Of note, these electrodes are not limited to detection of EEG signals. Rather, they may also be adopted for other purposes, including but not limited to electrocardiogram (ECG) signals and electromyogram (EMG) signals.

Figure 4:
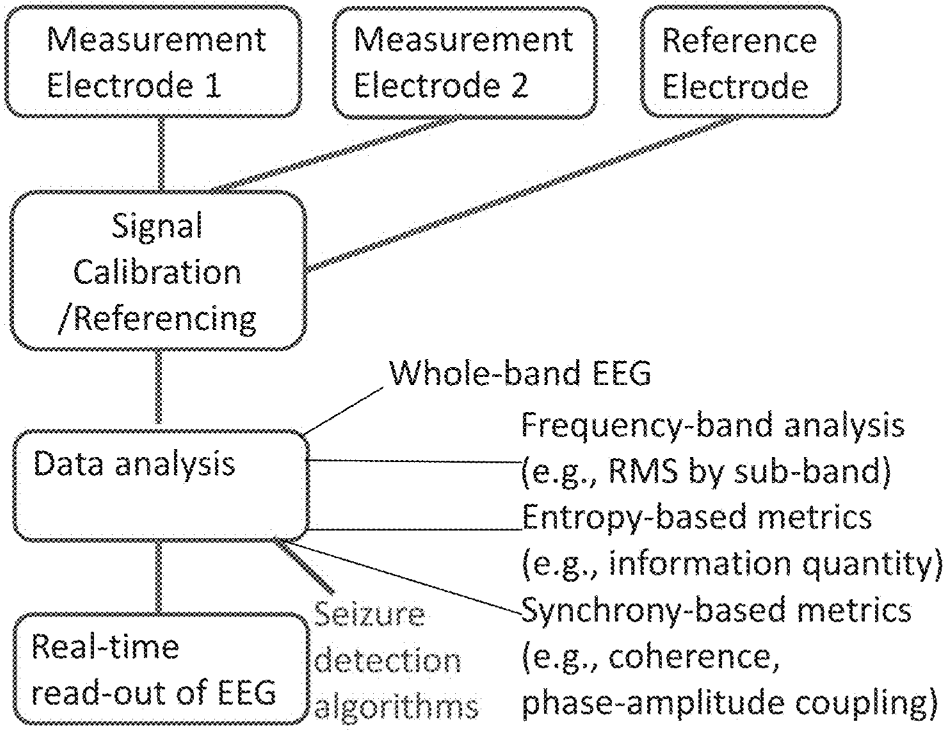
FIG. 4 shows an additional embodiment where the data analysis algorithm can be on-board or off-board and can include a seizure detection algorithm or other algorithm assisting with diagnosis or ongoing treatment (e.g. management of medically-induced coma, ischemia detection, etc.).

FIG. 4 shows an additional embodiment where the data analysis algorithm can be on-board or off-board and can include a seizure detection algorithm.

Figure 5A:
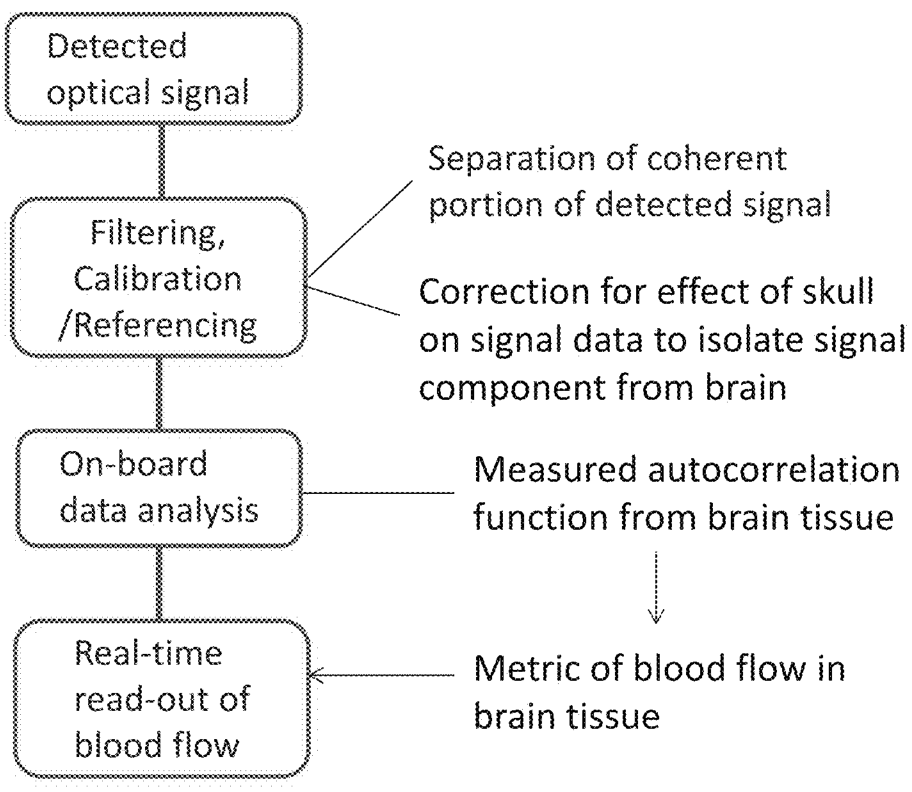
FIG. 5A shows a flow chart of optical blood flow measurement instructions of a signal processing component.

FIG. 5A shows an embodiment of the signal processing component of the optical portion of the invention. At each time point, the detected signal is obtained from light from the coherent source entering the tissue, propagating through the tissue, and eventually returning to the surface and entering the photodetector. The detected signal may be obtained from backscattered light. This signal is then post-processed via filtering and calibration methods to separate the coherent portion of the detected light and correct the signal for the effect of the skull on signal data to separate out the signal component from the brain. Then, data analysis is performed to extract the measured autocorrelation function from brain tissue and fit that function to a mathematical model to extract the measured blood flow in the tissue, which is read out in real time. With frequency modulation of the light amplitude, the detected light can be analyzed to separately determine the absorption and scattering properties of the interrogated tissue. This approach can be used to improve accuracy of optical oximetry. Scattering measurements provide an additional modality to study bulk changes in the interrogated tissue that may occur due to, for example, neuronal changes associated with but not limited to epileptic seizures, spreading depolarization, ischemia, or neurodegenerative changes.

Figure 5B:
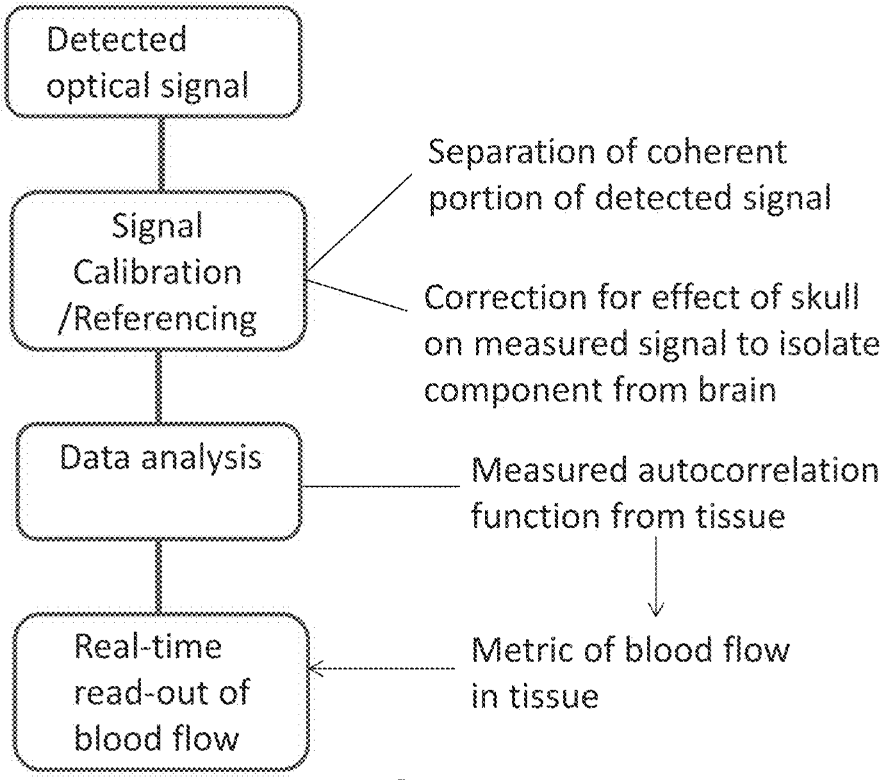
FIG. 5B shows an additional embodiment where the data analysis algorithm can be on-board or off-board.

FIG. 5B shows an additional embodiment where the data analysis algorithm can be on-board or off-board.

Figure 6A:
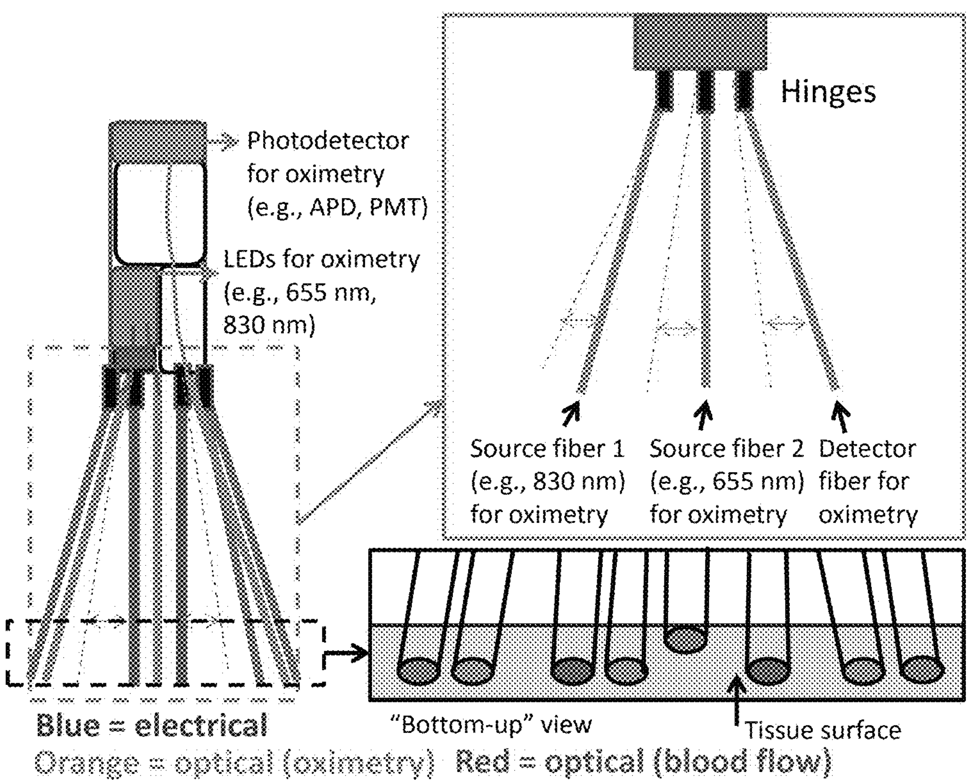
FIG. 6A shows a diagram of a portable EEG, blood flow, and oximetry measurement device comprising additional legs for oximetry measurements.

Referring now to FIG. 6A, the device may further comprise one or more oximetry optical source fibers and one or more oximetry optical detection fibers, including but not limited to a first LED connected to the first oximetry optical source fiber, a second LED connected to the second oximetry optical source fiber, and an oximetry photodetector connected to the oximetry optical detection fiber. The first LED or other type of light source may deliver light at a lower-energy range of a visible spectrum, near-infrared spectrum, or short-wave infrared spectrum, and the second LED or other type of light source may deliver light at a higher-energy range of a visible spectrum, near-infrared spectrum, or short-wave infrared spectrum. FIG. 6A shows an embodiment of the invention where three additional legs have been added to the instrument for optical oximetry measurements. Each leg contains an optical fiber; two of these fibers deliver light (e.g., from LEDs) to the tissue. One fiber delivers light at the higher-energy range of the visible spectrum (e.g., 655 nm) for sensitivity to deoxyhemoglobin, and the other fiber delivers light at the lower-energy range of the near-infrared spectrum (e.g., 850 nm) for sensitivity to oxyhemoglobin. These specific wavelengths serve as examples and can be modified depending on the specific component of interest being measured at a specified target organ, underscoring the versatility and flexibility of this invention to enable customization of the optical EEG pen for different users and purposes. Moreover, light from both sources propagates through the tissue until a portion of this light is detected by the detection fiber. The portion of light may be backscattered. The detected light is sent to a photodetector (e.g., APD, PMT).

Figure 6B:
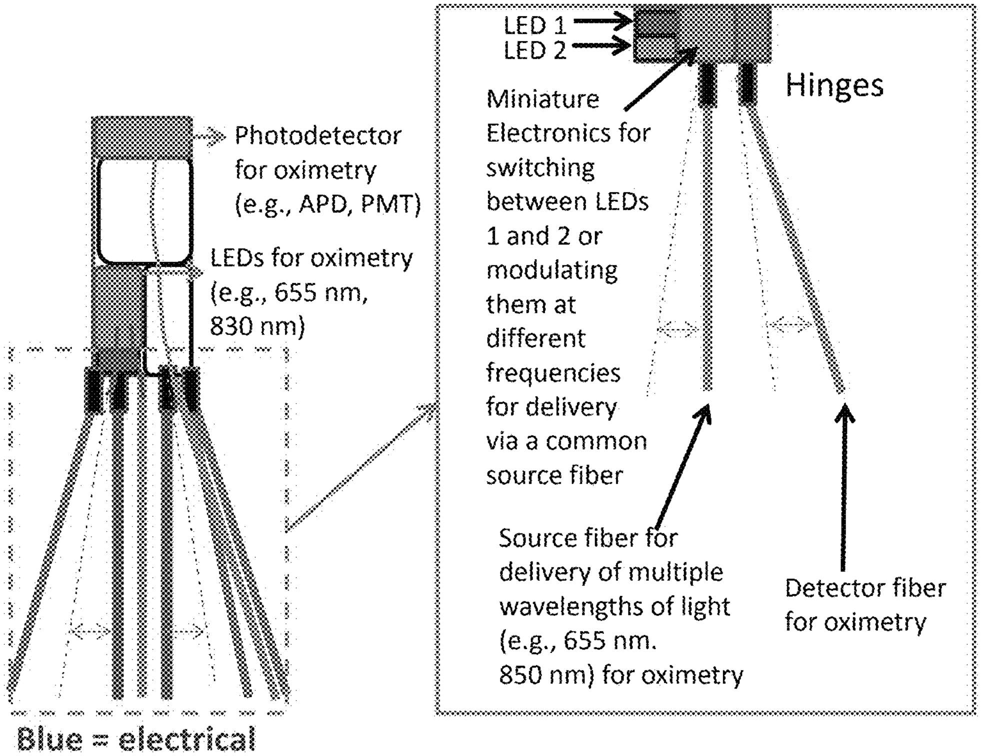
FIG. 6B shows a diagram of a portable EEG, blood flow, and oximetry measurement device comprising a leg capable of serving as the source fiber for measuring both oximetry and blood flow.

Referring now to FIG. 6B, the first and second oximetry optical source fibers may be disposed in a single leg. FIG. 6B shows an embodiment of the invention where the two non-coherent light sources (e.g., 655 nm, 850 nm) are delivered to the tissue via a single leg of the instrument, by using a miniature multiplexer for rapidly switching between the two light sources (e.g., LEDs or laser diodes) or modulating the two light sources at different frequencies to "encode" them separately.

Figure 6C:
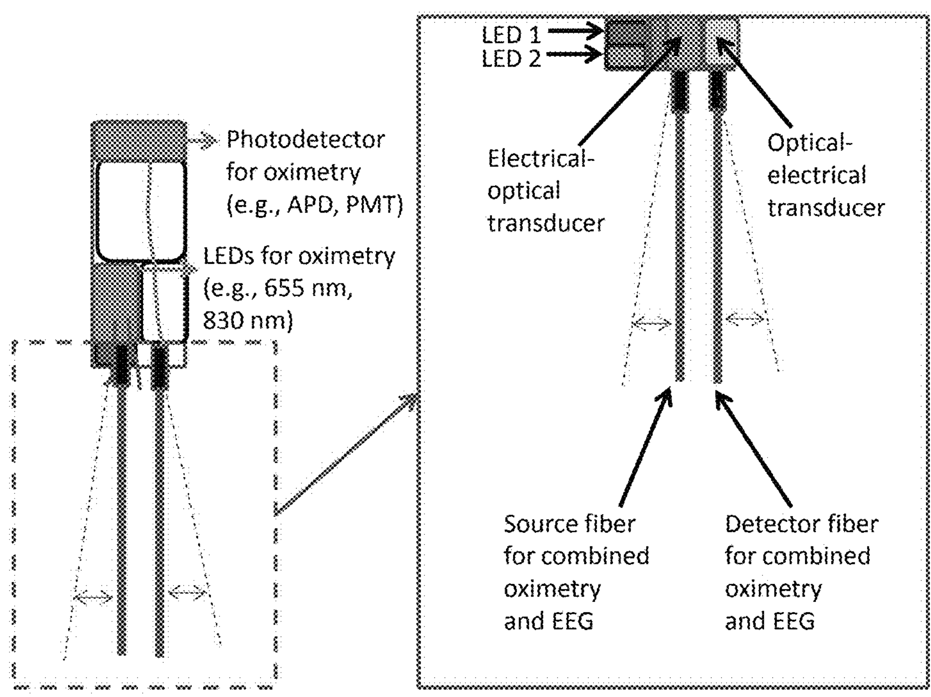
FIG. 6C shows a diagram of a portable EEG, blood flow, and oximetry measurement device comprising an electrical-optical transducer and an optical-electrical transducer.

Referring now to FIG. 6C, an oximetry optical source fiber may be capable of delivering electrical signals and the oximetry optical detection fiber may be capable of collecting electrical signals. The oximetry optical detection fiber may be connected to an electrical-optical transducer and/or an optical-electrical transducer. FIG. 6C shows an embodiment of the invention where the electrical and optical signals are delivered and collected via a pair of common fibers, with the source fiber connected to an electrical-optical transducer for converting electrical inputs into optical inputs, and with the detection fiber connected to an optical-electrical transducer for converting detected optical signals into electrical signals. Note that the number of fibers is not limited to two, as additional fibers can be added to increase the number of measurement/recording EEG electrodes as well as for additional optical signals as needed.

Figure 6D:
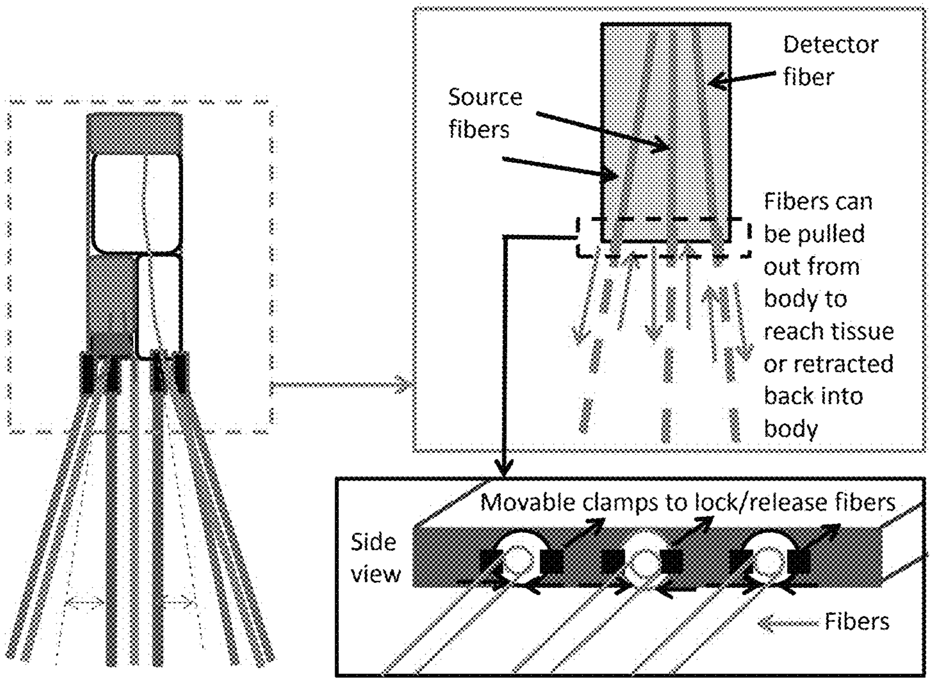
FIG. 6D shows a diagram of a portable EEG, blood flow, and oximetry measurement device comprising a plurality of movable clamps for retracting and extracting fibers.

FIG. 6D shows an embodiment of the invention where the optical fibers can be retracted into the pen body and extracted out of the pen body via an adjustable clamping mechanism.

Figure 7A:
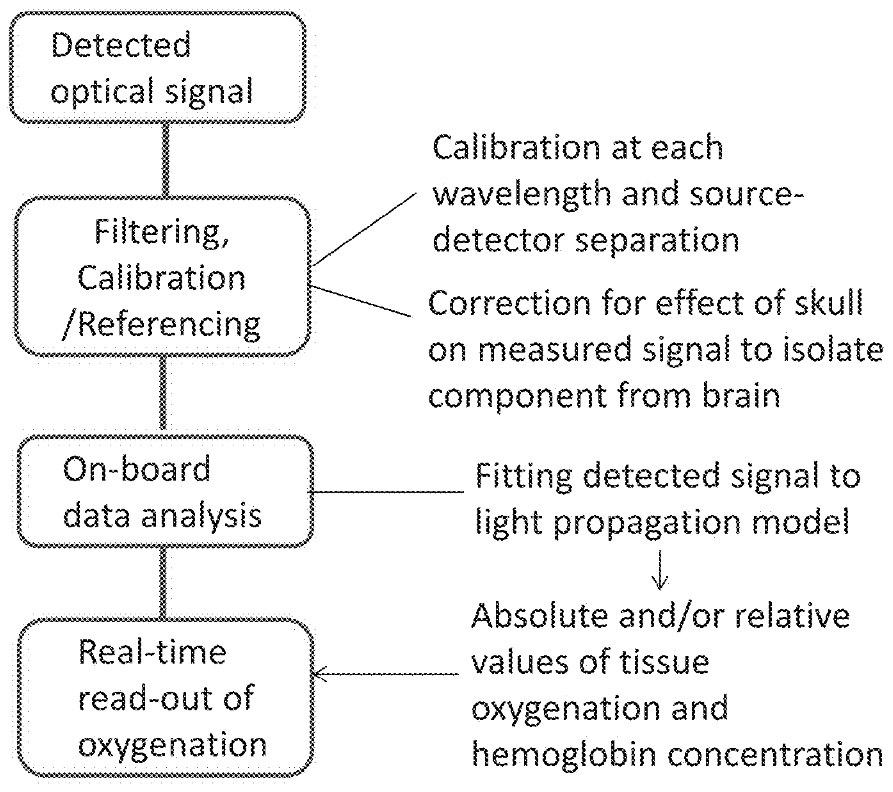
FIG. 7A shows a flow chart of oximetry measurement instructions of a signal processing component.

FIG. 7A shows an embodiment of the signal processing component of the additional optical portion of the embodiment of the invention shown in FIG. 6. At each time point, the detected signal is obtained from light from the two additional sources entering the tissue, propagating through the tissue, and eventually backscattering to the surface and entering the additional photodetector. This signal is then postprocessed via filtering and calibration methods specific to the wavelengths and source-detection separations, and the signal is corrected for the effect of the scalp/skull to separate out the component from the brain. Then, on-board data analysis is performed to fit the calibrated data to a light propagation model to extract the relative values of tissue oxygenation and hemoglobin concentration, which are read out in real time. In some embodiments, the invention may further comprise a frequency domain photon migration (FDPM) component for extracting the tissue absorption and scattering coefficients from the data using a light propagation model. These measured parameters can be combined with the blood flow parameter to measure cerebral oxygen metabolism, concomitant with cerebral blood flow, in real time.

The blood flow and oxygenation parameters can also be combined with the measured EEG parameters to measure neurovascular coupling in real time. In addition to tissue scattering metrics obtained from FDPM, these metrics can also be used to measure cortical spreading depolarization during diagnostic, prognostic, or therapeutic workup of brain injury. Furthermore, these metrics can be used to quantify the metabolic changes and/or neurovascular coupling changes during a variety of metabolic states, including the normal fed state, calorically restricted state, high versus low metabolic state (e.g. during exercise or "stress tests" conducted for assessment of particular organs), or pathological states such as hypoxia, ischemia, post-ischemia, reperfusion, and acute or delayed injury, as well as degenerative states such as neurodegenerative conditions (e.g. dementia). Application of the device during these states can be for the purpose of diagnostic, prognostic, or therapeutic purposes. Additionally, application of the device can include optimization of performance for the brain and heart to improve health and fitness. Interpretation of data can be made based on relative or absolute changes in the aforementioned metrics for a single person or a multitude of people using population databases.

Figure 7B:
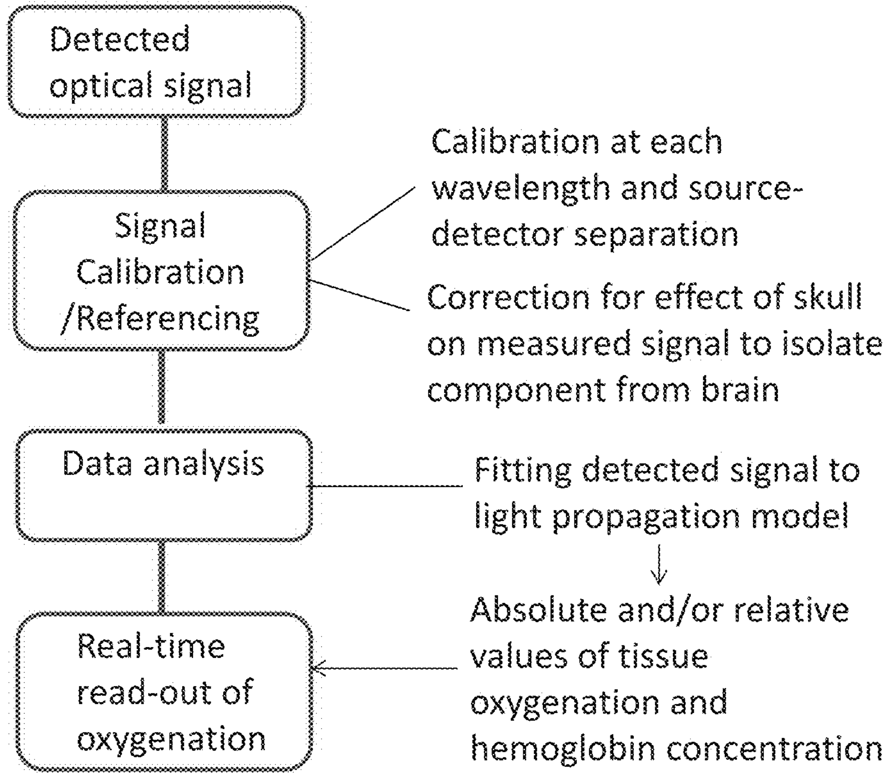
FIG. 7B shows an additional embodiment where the data analysis algorithm can be on-board or off-board.
Figure 8:
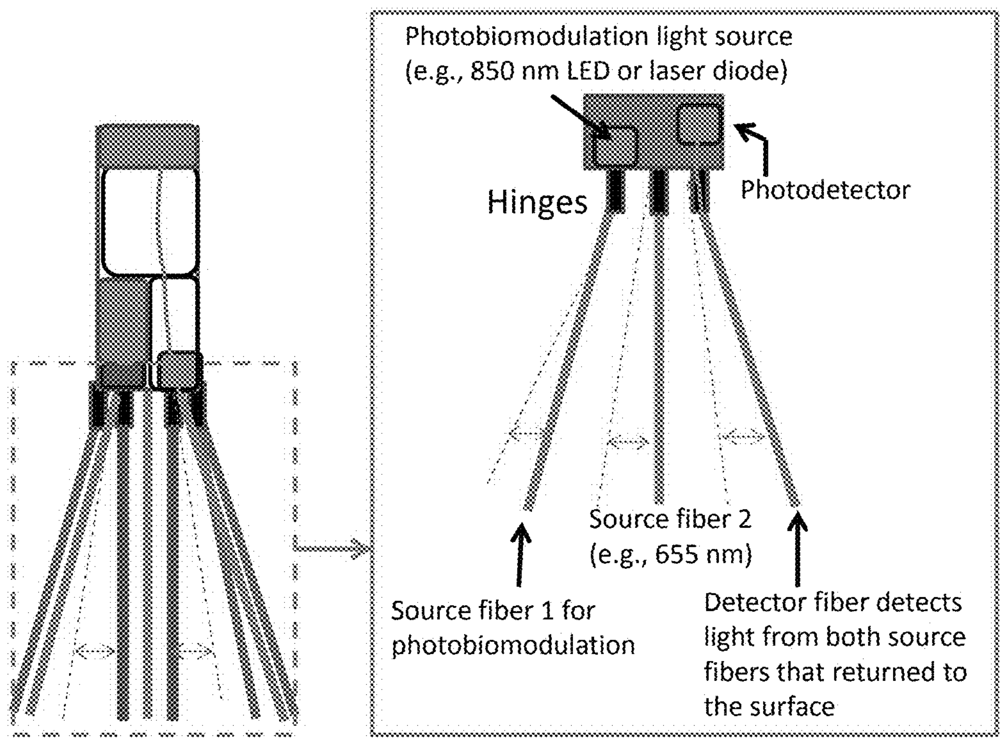
FIG. 8 shows a diagram of a portable blood flow measurement, oximetry measurement, and therapeutic biomodulation device.

FIG. 7B shows an additional embodiment where the data analysis algorithm can be on-board or off-board. Referring now to FIG. 8, the present invention features a portable device for therapeutic photobiomodulation and blood flow measurement. The device may comprise a body. The device may further comprise a plurality of legs comprising a first leg having a first optical source fiber, a second leg having a second optical source fiber, and a third leg having a detection fiber. Additional legs can be added as needed. Each leg may be pivotably connected to the body by a hinge or related type of attachment. The device may further comprise a photobiomodulation light source connected to the first optical source fiber, a non-photobiomodulation light source connected to the second optical source fiber, and a photodetector connected to the detection fiber. The photobiomodulation light source may produce light capable of therapeutic photobiomodulation of cells, the non-photobiomodulation light source may produce light for blood flow, oximetry, and metabolism measurement, and the detection fiber may receive backscattered light produced by the first and second optical source fibers. The photobiomodulation light source may produce visible light, near-infrared light, or short-wave infrared light to promote increased cellular metabolism of oxygen, generation of ATP, vasodilation, and/or enhanced perfusion of tissue or other biological change desired to, for example, promote healing or rapid medical intervention. Changes produced by the photobiomodulation light sources may be monitored in real time or delayed fashion by the photodetector. FIG. 8 shows an embodiment of the invention where one of the optical light sources (e.g., an LED, laser diode, or other light source) is appropriately optimized ("tuned") via modifying a number of parameters including but not limited to wavelength, frequency, and power to deliver visual light, near-infrared (e.g., 850 nm) light, or short-wave infrared light to the tissue for therapeutic photobiomodulation. The light may also have additional features, such as being pulsed or dynamically changing in space and time in the said parameters to achieve the desired goal. A portion of this light that is not absorbed by the tissue is scattered back to the surface (as is the case with the non-photobiomodulating light source), so the backscattered light from both sources is still detected by the detection fibers and sent to the photodetector to perform real-time measurements of absolute and/or relative values of tissue perfusion, oxygenation, and metabolism.

Figure 9:
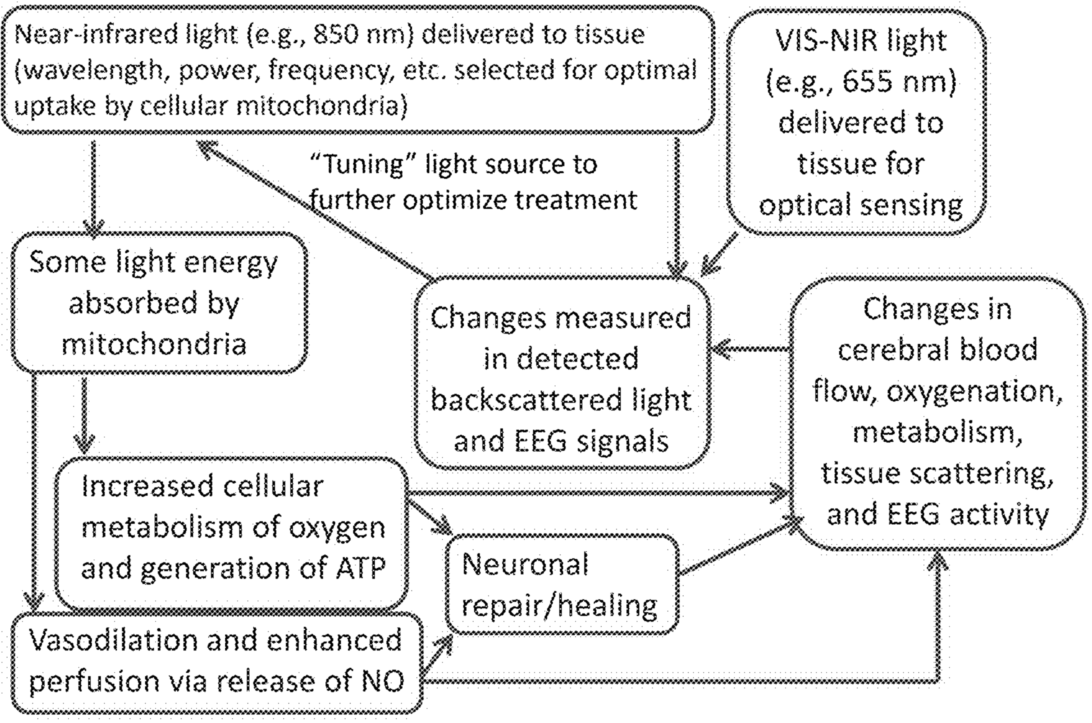
FIG. 9 shows a flow chart of a therapeutic photobiomodulation method of the present invention.

FIG. 9 shows a flow chart of an embodiment of the invention where visual light, near-infrared light (e.g., 850 nm), or short-wave infrared light is sent to the tissue for photobiomodulation. The input characteristics of this light (e.g., wavelength, power, frequency, etc.) are "tuned" for optimal uptake by cellular mitochondria or other biological components. A portion of the light energy is absorbed by the mitochondria, promoting increased cellular metabolism of oxygen and generation of ATP, or other biological components in addition to vasodilation and enhanced perfusion of the tissue via release of nitric oxide (NO). On the other hand, if vasoconstriction or reduced perfusion is desired as in the case of pathological hyperperfusion (e.g. reperfusion injury), such modulation can be implemented. These and potentially other factors can contribute to neuronal repair/healing. These healing processes enhanced by the photobiomodulation are manifested in changes in the blood flow, oxygenation, metabolism, tissue scattering, and electrical activity of the end organ (e.g. EEG in the brain, ECG in the heart, or EMG in the muscle). Changes in these parameters can be monitored in real time by the optical and electrical measurement capabilities of the instrument (via simultaneous real-time detection of backscattered coherent light, detection of backscattered incoherent light, and detection of EEG activity). These measurements can be used to quantify the effect of the photobiomodulation treatment on cerebral hemodynamic, metabolic, and electrical activity, and they can be used to provide feedback to modify the characteristics of the photobiomodulation source (e.g., wavelength, power, frequency) in real time to facilitate improved treatment.

Figure 10:
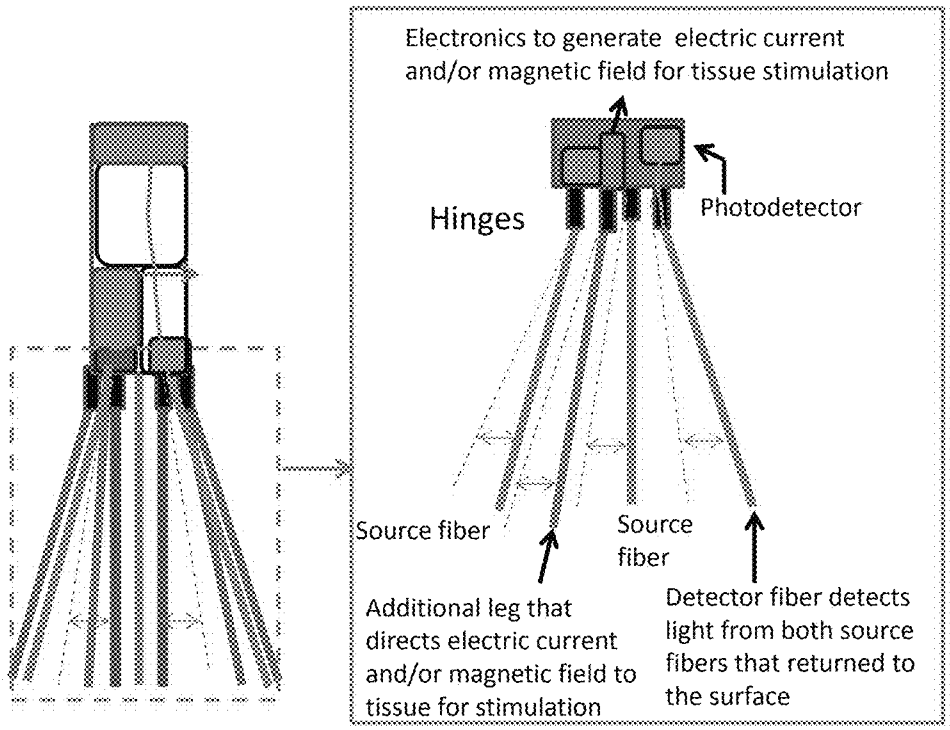
FIG. 10 shows a diagram of a portable blood flow measurement, oximetry measurement, and therapeutic biomodulation device comprising a leg for transmitting therapeutic electromagnetic stimulation.

Referring now to FIG. 10, the device may further comprise a fourth leg for delivering an electrical current and/or a magnetic field produced by a plurality of microelectronics, including but not limited to MEMS, disposed within the body for therapeutic electromagnetic biomodulation. The electrical current and/or magnetic field may promote perfusion, metabolism, and electrical activity and changes produced by the electrical current and/or magnetic field may be monitored in real time by the photodetector. FIG. 10 shows an embodiment of the invention where one or more additional legs are added to deliver an electric current and/or magnetic field to the tissue to stimulate repair/healing. This electromagnetic (EM) stimulation may be performed using miniaturized electronics in the pen body to generate electric currents and/or magnetic fields whose characteristics (e.g., power, frequency) are optimized to promote uptake by the tissue for therapeutic purposes, and transmitting the currents and/or fields through the additional legs of the device for delivery to the brain tissue. The additional legs may also have a hinge or related component like the other legs for adjustable positioning.

Figure 11:
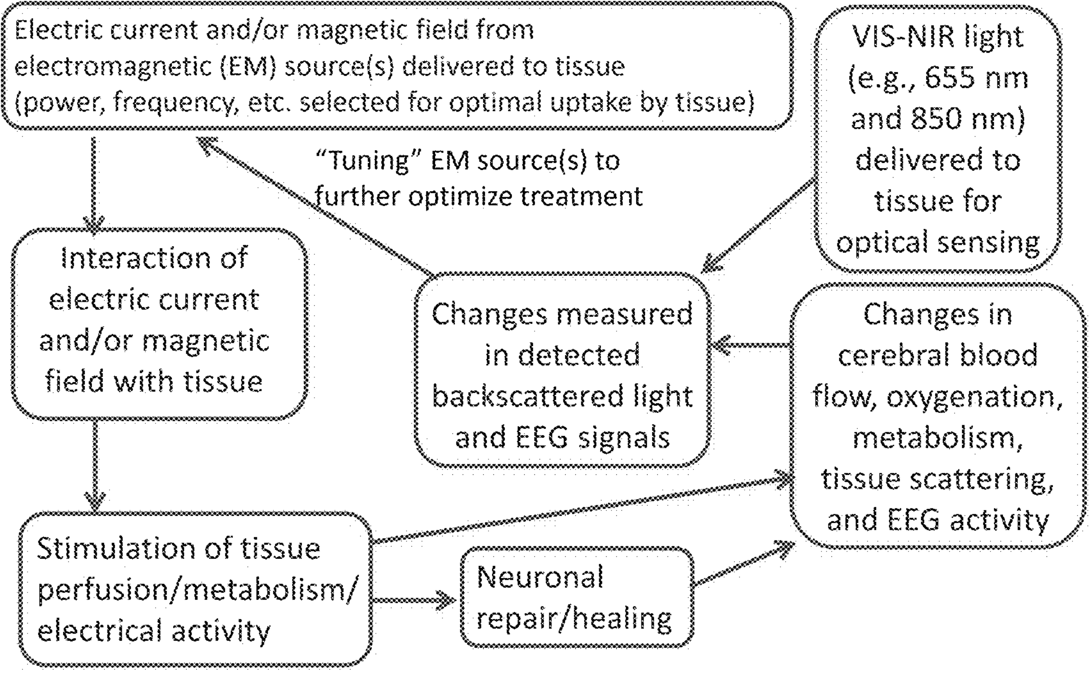
FIG. 11 shows a flow chart of a therapeutic electromagnetic stimulation method of the present invention.
Figure 12:
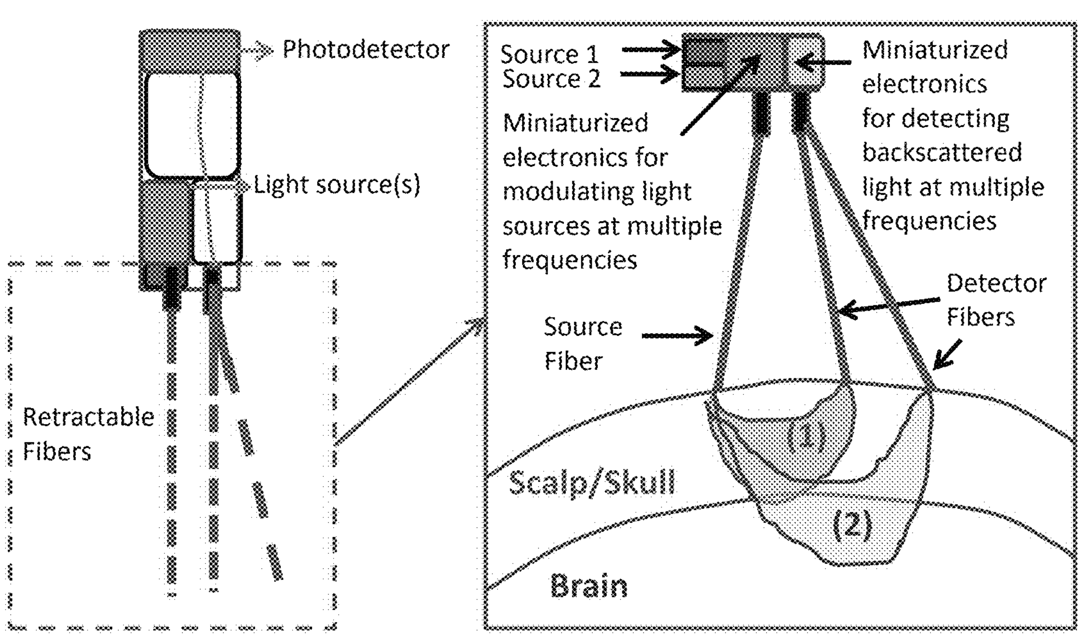
FIG. 12 shows an illustration of the concomitant measurement of electrical and optical signals, where retractable fibers, multiple source-detector separations, and separation of tissue absorption and scattering at each time point enable correction of the optical data for the effects of the scalp and skull to obtain quantitatively accurate brain blood flow, hemoglobin concentration, oxygenation, metabolism, and edema index, using a small form factor "pen" instrument.
Figure 13:
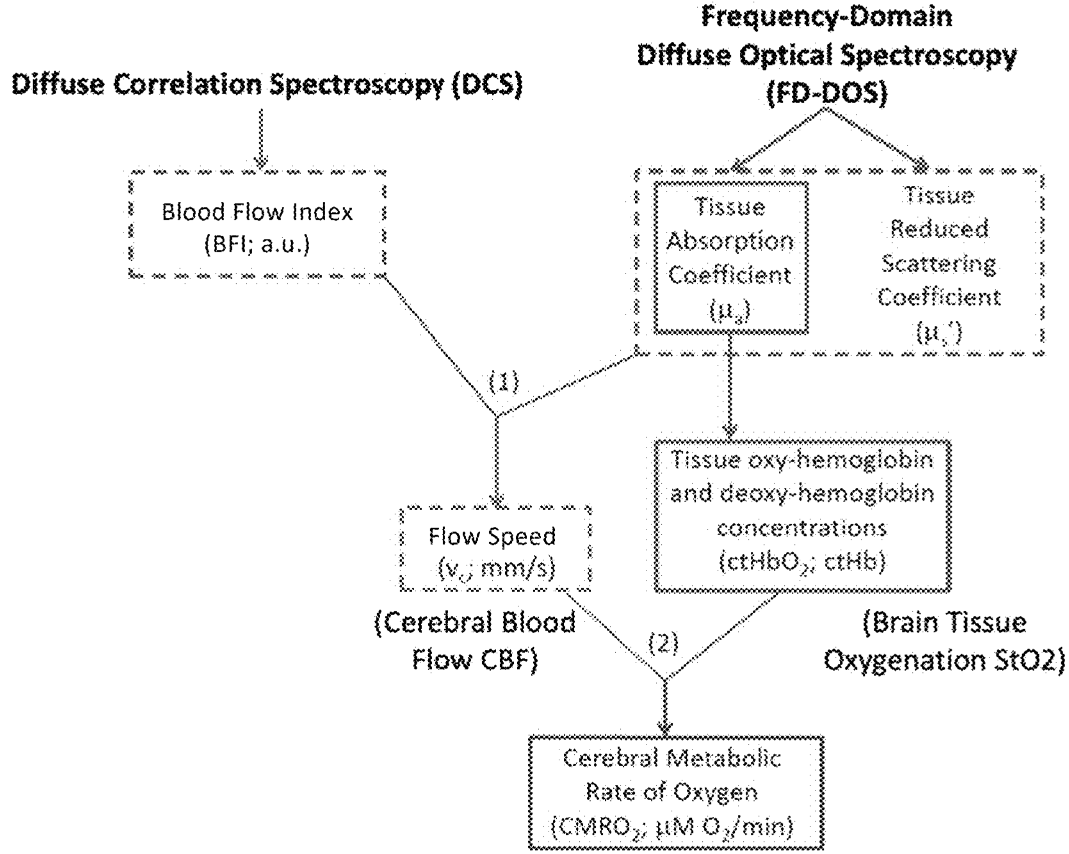
FIG. 13 shows an illustration of the measurement of absolute values of hemodynamic/metabolic parameters concomitant with EEG parameters. Note: In contrast to the present invention, previous products do not feature the combined flow+oxygenation+EEG with correction for varying tissue scattering to enable calculation of absolute values of CBF, $ctHbO_2$ ctHb, $StO_2$, and $CMRO_2$. Additionally, this enables the measurement of flow-metabolism autoregulation metrics.
Figure 14:
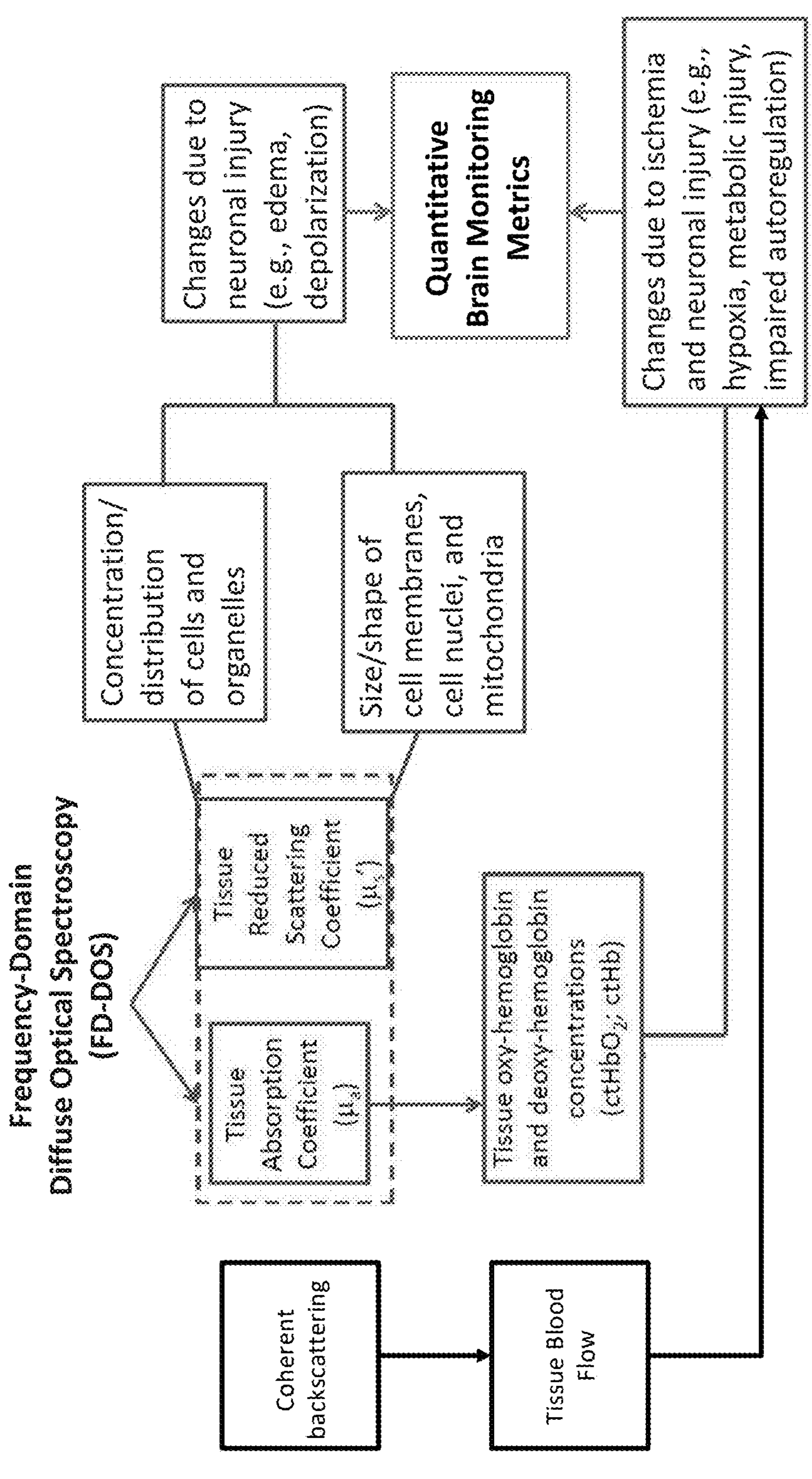
FIG. 14 shows an illustration of the measurement of tissue scattering changes (edema, cortical spreading depolarization, etc.) concomitant with hemodynamic and EEG changes.

FIG. 11 shows a flow chart of an embodiment of the invention where an electric current and/or magnetic field is sent to the tissue for electromagnetic (EM) stimulation (e.g., direct current stimulation, transcranial magnetic stimulation). The input characteristics of this current and/or field (e.g., power, frequency, etc.) are "tuned" for optimal uptake by the brain tissue. A portion of this EM energy is absorbed by the brain or other biological tissue, promoting increased perfusion, metabolism, and electrical activity. These and potentially other factors contribute to neuronal repair/healing. These healing processes enhanced by the EM stimulation are manifested in changes in the blood flow, oxygenation, metabolism, tissue scattering, and electrical activity in the brain or other tissue. Changes in these parameters can be monitored in real time by the optical and electrical measurement capabilities of the instrument (via simultaneous real-time detection of backscattered coherent light, detection of backscattered incoherent light, and detection of electrical activity). These measurements can be used to quantify the effect of the EM stimulation treatment on hemodynamic, metabolic, and electrical activity, and they can be used to provide feedback to modify the characteristics of the EM source (e.g., power, frequency) in real time to facilitate improved treatment.

The various systems and devices described herein may be used in the implementation of novel methods for quantitative intracranial monitoring. In preferred embodiments, the methods are non-invasive and may be quickly implemented to determine various biometrics of interest. The various methods described herein may be implemented via the execution of instructions held or stored in the memory component of one of the devices of the present invention.

In some embodiments, the present invention features a non-invasive method of determining an absolute value of cerebral metabolic rate of oxygen ($CMRO_2$) using a calibration method based on the mean penetration depth of the light source into the tissue. This technique provides for the determination of an absolute (rather than relative) value of $CMRO_2$ while also allowing for the evaluation of $CMRO_2$ at specified depths, as determined by the wavelength and modulation frequency of the light source and the geometry of the measurement system. Depth-resolved determination of $CMRO_2$ (e.g. at multiple depths) enables measurement of $CMRO_2$ in different regions of the brain. Combining this measurement with CBF or EEG data allows for measurement of flow-metabolism coupling and neurovascular coupling in different regions of the brain.

In some embodiments, the method may use optical measurement of tissue perfusion, absorption, and scattering to determine the penetration-depth-calibrated absolute value of $CMRO_2$. As a non-limiting example, the method may include: positioning one or more light sources and two or more detectors in proximity to a cerebral tissue of a subject (e.g. in proximity to the subject's head); emitting a coherent light signal from one or more of the light sources into the head such that that one or more backscattered light signals are generated; detecting one or more of the backscattered light signals via the two or more detectors; determining a dynamic perfusion metric, a tissue absorption coefficient, and a tissue scattering coefficient from the detected signals; determining a mean penetration depth of the detected signals, using the tissue absorption coefficient and tissue scattering coefficient; and determining an absolute value of $CMRO_2$ using the mean penetration depth, the dynamic perfusion metric, the tissue absorption coefficient, and the tissue scattering coefficient. In this way, the absolute value of $CMRO_2$ may be depth-calibrated using the mean penetration depth. In preferred embodiments, the dynamic perfusion metric, the tissue absorption coefficient, and the tissue scattering coefficient provide all the information necessary to calculate the depth-calibrated absolute value of $CMRO_2$. For example, the depth-calibrated absolute value of $CMRO_2$ may be determined using a single device with a single set of optical sources and detectors, without any peripheral measurement or non-optical measurements required for calibration. As another non-limiting example, the depth-calibrated absolute value of $CMRO_2$ may be determined by multiplying a concentration of deoxygenated hemoglobin, a calibrated perfusion metric, and the mean perfusion depth, all of which are determined from the dynamic perfusion metric, the tissue absorption coefficient, and the tissue scattering coefficient.

In some embodiments, the method may additionally include modifying the light emission or detection to change the mean penetration depth. The method may also include calculating a depth-calibrated absolute value of $CMRO_2$ at each mean penetration depth. As non-limiting examples, the mean penetration depth may be changed by adjusting one or more source-detector separation distances, modulation frequencies, or wavelengths of the coherent or incoherent light signals, or a combination thereof. In some embodiments, the device may be configured to calculate absolute value of $CMRO_2$ at a selected depth, and may be programmed with instructions for iteratively determining the mean penetration depth and adjusting one or more parameters effecting mean penetration depth until the selected depth is reached, and then determining the absolute value of $CMRO_2$ at that selected depth. Similarly, other measurements of interest, such as tissue perfusion, hemoglobin concentration, oxygenation, other fluid concentrations, or tissue scattering, may be made at a selected mean penetration depth.

In some embodiments, the method may additionally include determining one or more fluid metrics from the detected signals. In selected embodiments, the fluid metrics may be indicative of a degree of swelling or edema of the tissue. Non-limiting example fluid metrics include parameters of cellular components of the tissue. Non-limiting examples of parameters of cellular components of the tissue include: a shape, a size, or a refractive index of the cellular components. Determination of these fluid metrics may be advantageous because they provide information about additional structural and functional changes in tissue, including edema and changes in concentration of intracellular versus extracellular tissue components. These parameters may be combined with the measured $CMRO_2$ to calculate a multi-dimensional metric that merges a hemodynamic measure of metabolism ($CMRO_2$ calculated from the blood flow, hemoglobin concentration, and oxygenation metrics) with a structural measure of metabolism (changes in sizes, shapes, and concentrations of organelles (e.g., mitochondria) in the tissue, as measured by tissue scattering and water fraction).

In some embodiments, a calibrated perfusion metric may be determined using the dynamic perfusion metric. As a non-limiting example, the dynamic perfusion metric may be calibrated via the tissue absorption coefficient and the tissue scattering coefficient in order to yield the calibrated perfusion metric. The calibrated perfusion metric may be used in the determination of the absolute value of $CMRO_2$. This calibrated perfusion metric may be a diffuse flow calibrated perfusion metric, a directed flow calibrated perfusion metric, or a calibrated perfusion metric which accounts for both diffuse and directed flow. In some embodiments separate values of $CMRO_2$ may be calculated using a diffuse flow calibrated perfusion metric and a directed flow calibrated perfusion metric. Measuring these two separate $CMRO_2$ values can potentially provide information about $CMRO_2$ in two different regions of tissue: a region closer to large blood vessels (where directed blood flow dominates the perfusion metric) and a region further away from large blood vessels (where diffuse flow dominates the perfusion metric). The Brownian diffusion coefficient (Db) is a non-limiting example of a diffuse flow calibrated perfusion metric. Directed flow speed ($v_c$) is a non-limiting example of a directed flow calibrated perfusion metric. Cerebral blood flow measures can include either of these or a combination of the two. Without wishing to limit the present invention to any particular theory or mechanism, the calibrated perfusion metric may represent an optically measured area of tissue being oxygenated (via diffuse blood flow) per unit time or a speed of tissue oxygenation (via directed blood flow).

In some embodiments, the absolute value of $CMRO_2$ may be corrected to account for an effect of a geometry or arrangement of the light sources and detectors. As a non-limiting example, the spatial arrangement of the sources and detectors may be taken into consideration so that they may be corrected for.

In some embodiments, the method may include determination of additional metrics and/or relationships between metrics. As a non-limiting example, the method may additionally include dividing the absolute value of $CMRO_2$ by the calibrated perfusion metric to determine a depth-calibrated value of cerebral autoregulation. This will enable the measurement of cerebral autoregulation in different regions of the brain.

As another non-limiting example, the method of determining an absolute value of cerebral metabolic rate of oxygen ($CMRO_2$) using a volumetric calibration may include: positioning one or more light sources and two or more detectors in proximity to a head of a subject; emitting a coherent light signal from one or more of the light sources into the head (e.g. through the scull into a cerebral tissue), such that one or more backscattered light signals are generated; detecting one or more of the backscattered light signals via the two or more detectors, where the detected signals correspond to an optically measured volume of tissue; calculating a tissue absorption coefficient and a tissue scattering coefficient from the detected signals; calculating a calibrated perfusion metric from the detected signals; calculating a deoxygenated hemoglobin concentration (ctHb) in the volume of tissue from the tissue absorption coefficient; calculating a mean penetration depth of the detected signals, using the tissue absorption coefficient and tissue scattering coefficient; and calculating an absolute value of $CMRO_2$ from the deoxygenated hemoglobin concentration, the calibrated perfusion metric, and the mean penetration depth. Without wishing to limit the present invention to any particular theory or mechanism, it is believed that the calibrated perfusion metric represents perfusion over an area of the volume of tissue.

In some embodiments, the tissue absorption coefficient and tissue scattering coefficient may be determined via Spatial Frequency Domain Imaging (SFDI), Diffuse Optical Spectroscopy (DOS), or Near Infrared Spectroscopy (NIRS). The calibrated perfusion metric may be determined via Laser Speckle Imaging (LSI), Diffuse Correlation Spectroscopy (DCS), or Laser Doppler Flowmetry (LDF). The calibrated perfusion metric may be determined via calibration of a dynamic perfusion metric using the tissue absorption coefficient and the tissue scattering coefficient. As a non-limiting example, the dynamic perfusion metric may be a speckle flow index (SFI) or a blood flow index (BFI), and the calibrated perfusion metric may be a Brownian diffusion coefficient (Db), a directed flow speed ($v_c$), a cerebral blood flow (CBF) or a combination thereof.

In an alternative embodiment, the present invention features a method of determining an absolute value of cerebral metabolic rate of oxygen ($CMRO_2$) using a zero-flow calibration. In some embodiments the method may include calculating a calibration coefficient (a) based on a rate of change of deoxyhemoglobin concentration during entry into a zero-flow state (or a rate of change of oxyhemoglobin during exit from a zero-flow state), and determining an absolute value of $CMRO_2$ using the calibration coefficient. The zero-flow state may be intentionally induced, or a subject may be monitored during a zero-flow inducing situation such as cardiac arrest or a stroke.

As a non-limiting example, a zero-flow calibration method may include: positioning one or more light sources and two or more detectors in proximity to a body surface of a subject such as an arm or a leg; emitting a coherent light signal from one or more of the light sources into the body surface, such that one or more baseline backscattered light signals are generated; detecting one or more of the baseline backscattered light signals via the two or more detectors in proximity to the body surface; calculating baseline values of cerebral blood flow (CBF), tissue oxy-hemoglobin concentration ($ctHbO_2$), tissue deoxy-hemoglobin concentration (ctHb), and tissue scattering from the detected baseline signals; temporarily inducing a zero-flow blood perfusion state in the body surface; emitting a coherent light signal from one or more of the light sources into the body surface, such that one or more zero-flow backscattered light signals are generated; detecting one or more of the zero-flow backscattered light signals via the two or more detectors in proximity to the body surface; calculating the rate of change of deoxyhemoglobin concentration in the tissue during the zero-flow state from the detected zero-flow signals; calculating a calibration coefficient (a) based on the calculated baseline values and the rate of change of deoxyhemoglobin concentration in the tissue during the zero-flow state; restoring blood perfusion to the body surface; positioning one or more light sources and two or more detectors in proximity to a head of the subject; emitting a coherent light signal from one or more of the light sources into the head, such that one or more cerebral backscattered light signals are generated; detecting one or more of the cerebral backscattered light signals via the two or more detectors in proximity to the head; calculating cerebral blood flow (CBF) (or another metric of perfusion using a technique such as LDF), tissue oxy-hemoglobin concentration ($ctHbO_2$), tissue deoxy-hemoglobin concentration (ctHb), and tissue scattering from the detected cerebral signals; and determining the absolute value of $CMRO_2$ using the calibration coefficient (a) and the calculated cerebral blood flow (CBF), tissue oxy-hemoglobin concentration ($ctHbO_2$), tissue deoxy-hemoglobin concentration (ctHb), and tissue scattering.

In some embodiments, the method uses a single set of light sources and detectors which are repositioned from proximity to the body surface to proximity to the head. In other embodiments, multiple sets of light sources and detectors may be used such that one set is positioned in proximity to the body surface such as an arm or a leg while a second set is positioned in proximity to the head. In one embodiment, the sources and detectors may extend from a single pen-shaped device. In another embodiment, the sources and detectors may extend from a head cap. The head cap may be worn in anticipation of entry into a zero-flow state, or in anticipation of exit from a zero flow state.

The zero-flow blood perfusion state in the body surface may be temporarily induced via application of pressure to block blood flow. As a non-limiting example, pressure may be applied to a limb via a cuff similar to a blood pressure monitoring cuff. In one embodiment, pressure may be applied to the cuff for a zero-flow period of about 10 seconds to 5 minutes. In other embodiments, the zero-flow state may be induced by cardiac arrest or a stroke. In some embodiments, the rate of change of deoxyhemoglobin concentration may be determined while the tissue is entering or leaving a zero-flow state. In one embodiment the zero-flow state may be induced by temporary occlusion of a brain blood vessel.

EXAMPLES

The following are non-limiting examples of the present invention. It is to be understood that said examples are not intended to limit the present invention in any way. Equivalents or substitutes are within the scope of the present invention.

Example 1: Use of a Device of the Present Invention to Measure an Absolute Value of $CMRO_2$ Step 1: Extend a light source leg and a detector leg from the portable device.

Step 2: Illuminate the tissue with the coherent and incoherent light source(s), and detect the backscattered light with the photodetector(s). One or more of these light sources may be modulated at different frequencies, and there may be multiple sources, detectors, and wavelengths of light.

Step 3: Perform calibration and data processing procedures to obtain a blood flow index from the coherent light measurement and obtain a tissue absorption and scattering coefficient from the incoherent light measurement. The tissue absorption coefficient can then be fit to a linear combination of the different endogenous chromophores in the tissue (e.g., oxygenated hemoglobin, deoxygenated hemoglobin, water, etc.) to obtain the concentration or fractional contribution of each chromophore.

Step 4: Use the measured tissue absorption and scattering coefficient along with the blood flow index to obtain a corrected value of blood flow in physiological units.

Step 5: Combine the corrected blood flow data with the hemodynamic data to obtain an absolute value of tissue metabolic rate of oxygen in physiological units.

Example 2: Use of a Device of the Present Invention to Quantify Cerebral Autoregulation Step 1: Perform the process described in Example 1 to obtain a quantitative value of blood flow and a quantitative value of tissue metabolic rate of oxygen.

Step 2: Calculate an autoregulation metric by dividing the quantitative value of the absolute perfusion metric by the quantitative value of the absolute metabolic metric. Alternatively, the quantitative value of cerebral autoregulation may be calculated by dividing the rate of change of an absolute or relative perfusion metric by the rate of change of an absolute or relative metabolic metric, or by other methods described above (in claim).

Example 3: Use of a Device of the Present Invention to Monitor a COVID-19 Patient Step 1: Measure blood flow, metabolism, and/or an autoregulation metric for the brain with the device, using the method described in Example 2.

Step 2: Measure blood flow, metabolism, and/or an autoregulation metric for a different part of the body (e.g., lung or limb) with the device, using the method described in Example 2.

Step 3: Calculate a ratio of, or a difference between, the measured blood flow, metabolism, and/or autoregulation metrics for the two different parts of the body.

Step 4: Compare this metric with a previously measured range for healthy subjects and/or a previously-obtained "baseline" value of the metric for the same patient (e.g., a value measured upon admission to the hospital) to assess whether the patient exhibits a deficit in blood flow, metabolism, and/or autoregulation between two different parts of the body.

Step 5: Monitor this metric periodically over time, including in response to clinical treatment, to assess the recovery of the patient and the effectiveness of the clinical intervention. As a simple example, if the COVID-19 patient has thromboses in certain body parts or end organs demonstrated by a reduction in blood flow, a treatment such as anticoagulation can be initiated to treat the potential ischemia or risk of embolization that can lead to a pulmonary embolism or stroke. As a more advanced example, if the blood flow, metabolism, or autoregulation metric between the brain and lung are disparate, including for example a hypoxic lung but normoxic brain, then the ventilator settings can be adjusted so as to avoid excessive oxygen and air pressure that could damage the lung while avoiding a potential stroke or long term hypoxic brain damage. At the best case scenario, such a patient might avoid needing endotracheal intubation and mechanical ventilation altogether and instead may tolerate non-invasive ventilation such as a high-flow nasal cannula, CPAP or BiPAP device because the brain, the organ that is most sensitive to hypoxia and ischemia, might not benefit from additional oxygen delivered by invasive mechanical ventilation. Avoidance of mechanical ventilation can help to save the life of another patient due to a potential shortage of ventilators during a pandemic such as COVID-19.

Example 4: Use of a Device of the Present Invention to Diagnose, Treat, and Monitor an Acute Brain Injury Step 1: When encountering a patient with altered mental status with the differential diagnosis of seizure, stroke, or drug overdose, the device would be deployed to the brain to assess cerebral electrical activity (i.e. EEG), blood flow, metabolism, and/or an absolute $CMRO_2$ as stated in Example 1.

Step 2: The information provided by the device would help with the diagnosis of the patient. For example, epileptiform discharges seen on the EEG data would suggest possible ongoing seizure activity, diminished cerebral blood flow in a particular part of the brain that corroborates with contralateral motor weakness in a limb might suggest an ongoing ischemic stroke, or a particular EEG signal (e.g. triphasic waves) or a diminished EEG signal or metabolic activity throughout the whole brain might support a drug overdose (e.g. benzodiazepine or opioid overdose).

Step 3: In each of these cases, a treatment can be administered. The treatment might be pharmacologic in nature or the device itself can be utilized to induce a rapid optical wave (e.g. photobiomodulation) or electromagnetic wave to treat the condition. As a hypothetical example, the said treatment might result in treatment of the seizure (e.g. by rapid induction of cortical spreading depolarization), stroke (e.g. optical or electromagnetic thrombolysis), or drug overdose (e.g. optical or electromagnetic stimulation of breathing centers to avoid respiratory depression due to drug overdose).

Example 5: Use of a Device of the Present Invention to Diagnose, Treat, and Monitor an Acute Cardiac Event Step 1: When encountering a patient who is suspected of a potential heart attack and CPR is being initiated by other bystanders (e.g. basic life support) or health care providers (e.g. advanced cardiac life support), the device is deployed to the chest area to assess the cardiac electrical activity (i.e. ECG). This will help determine the cardiac rhythm (e.g. non-shockable rhythm versus a shockable rhythm) to help with diagnosis of the condition.

Step 2: Treatment may be guided by the device and potentially provided by the device. For example, if the device's ECG data indicates a shockable rhythm such as ventricular fibrillation or ventricular tachycardia, a shock needs to be administered. The device itself can have the potential to deliver a shock sufficient enough to convert the cardiac rhythm to normal sinus rhythm similar to an Automated External Defibrillator (AED) except that the said device would be handheld and more rapidly deployed than an AED.

Step 3: The device can additionally be used to monitor the brain during ongoing CPR to ensure that chest compressions and administered breaths are providing sufficient blood flow and oxygen to the brain to avoid hypoxic-ischemic brain damage. Additionally, after successful resuscitation of the patient, the brain can be monitored using the device to monitor brain electrical activity (e.g. spreading depolarizations and repolarizations), blood flow, and metabolism to help guide ongoing medical therapy to optimize a favorable outcome for the patient.

Example 6: High-Speed Quantitative Optical Imaging of Absolute Metabolism in the Rat Cortex Quantitative measures of blood flow and metabolism are essential for improved assessment of brain health and response to ischemic injury. This example demonstrates a multimodal technique for measuring the cerebral metabolic rate of oxygen ($CMRO_2$) in the rodent brain on an absolute scale (μM $O_2$/min). This example uses laser speckle imaging (LSI) at 809 nm and spatial frequency domain imaging (SFDI) at 655 nm, 730 nm, and 850 nm to obtain spatiotemporal maps of cerebral blood flow (CBF), tissue absorption ($\mu_a$), and tissue scattering ($\mu_s'$). Knowledge of these three values enables calculation of a characteristic blood flow speed, which in turn is input to a mathematical model with a "zero-flow" boundary condition to calculate absolute $CMRO_2$. This method is applied to a rat model of cardiac arrest (CA) and cardiopulmonary resuscitation. With this model, the zero-flow condition occurs during entry into CA. The $CMRO_2$ values calculated with this method are in good agreement with those measured with magnetic resonance (MR) and positron emission tomography (PET). Baseline absolute $CMRO_2$ values were statistically significant for distinguishing rats that exhibited good vs. poor short-term neurological recovery, as measured by electrocorticography. This technique provides a quantitative metric of cerebral metabolism that can potentially be used for comparison between animals and longitudinal monitoring of a single animal over multiple days, to assess differences in baseline metabolism and track recovery of metabolism in survival studies following ischemia and reperfusion.

Introduction:

Measurements of cerebral metabolic rate of oxygen ($CMRO_2$) may provide insight into the viability of brain tissue following ischemia. In particular, knowledge of $CMRO_2$ in absolute units would obviate the need for baseline measurements and facilitate longitudinal measurements to track longer-term cerebral recovery following ischemia and reperfusion. Also, absolute $CMRO_2$ measurements would enable quantitative comparisons between the values of different subjects at baseline and at subsequent time points in preclinical or clinical studies.

Unfortunately, conventional clinical monitoring techniques (e.g., arterial blood pressure, jugular bulb oximetry, pulse oximetry, laser Doppler flowmetry) typically cannot separate alterations in cerebral metabolism from changes in blood flow. Established techniques to measure $CMRO_2$ include medical imaging modalities such as Positron Emission Tomography (PET) and functional Magnetic Resonance Imaging (fMRI). PET can measure absolute $CMRO_2$, but it is expensive and non-portable, and requires use of exogenous contrast agents containing radioactive tracers. fMRI measures $CMRO_2$ changes via the blood oxygen level dependent (BOLD) signal, but it provides absolute $CMRO_2$ only with extensive calibration, as the BOLD signal only serves as a surrogate for cerebral blood flow and hemoglobin content and not as a direct measurement of these quantities. Additionally, both PET and BOLD fMRI typically have limited temporal resolution and cannot be performed repeatedly on a patient over a short period to monitor hyperdynamic changes caused by acute insults.

Diffuse optical spectroscopy (DOS) and diffuse optical imaging (DOI) techniques are an attractive alternative, as they are noncontact and use measurements of low-irradiance visible and near-infrared light to extract endogenous tissue absorption and scattering coefficients. Further analysis of the absorption coefficient yields measurements of relative changes in hemoglobin content and oxygen saturation. Frequency-modulated and time-resolved techniques enable absolute measurements of these two parameters. Coherent light techniques, such as diffuse correlation spectroscopy, enable measurements of blood flow. Combined use of these techniques can yield measurements of $CMRO_2$. However, the majority of these techniques have limited spatial resolution, oftentimes serving as point measurements.

It has been demonstrated that the combination of Spatial Frequency Domain Imaging (SFDI) and Laser Speckle Imaging (LSI)) can quantify tissue metabolic changes with both high spatial and temporal resolution. High-speed LSI and SFDI has been used to measure perfusion, oxygenation, and tissue scattering in the brain in a cardiac arrest (CA) model of global cerebral ischemia. The capability of this rapid multimodal SFDI+LSI system to image blood flow and hemoglobin concentration simultaneously enables high-speed measurement of $CMRO_2$. Furthermore, it is possible to account for the effects of time-varying tissue scattering at multiple wavelengths and the contribution of venous regions versus parenchyma when calculating $CMRO_2$. The present example features an approach to analyze multimodal optical imaging data with a mathematical model of $CMRO_2$ that incorporates a "zero-flow" boundary condition during the onset of ischemia in a CA model, to obtain the parameters necessary for absolute $CMRO_2$ measurements.

Methods

Animal Preparation: Ten male Wistar rats (weight~300-400 g) were imaged. Before the experiment, all subjects were endotracheally intubated under isoflurane anesthesia. Each subject had epidural screw electrodes implanted for electrocorticography (ECoG) and a hemicraniectomy (4 mm right-to-left×6 mm anterior-to-posterior) was performed to enable imaging of a portion of the right sensory and visual cortices. Cannulation of the femoral artery allowed the delivery of drugs, sampling of blood, and monitoring of blood pressure.

Figures 15, 16A, 16B, 16C:
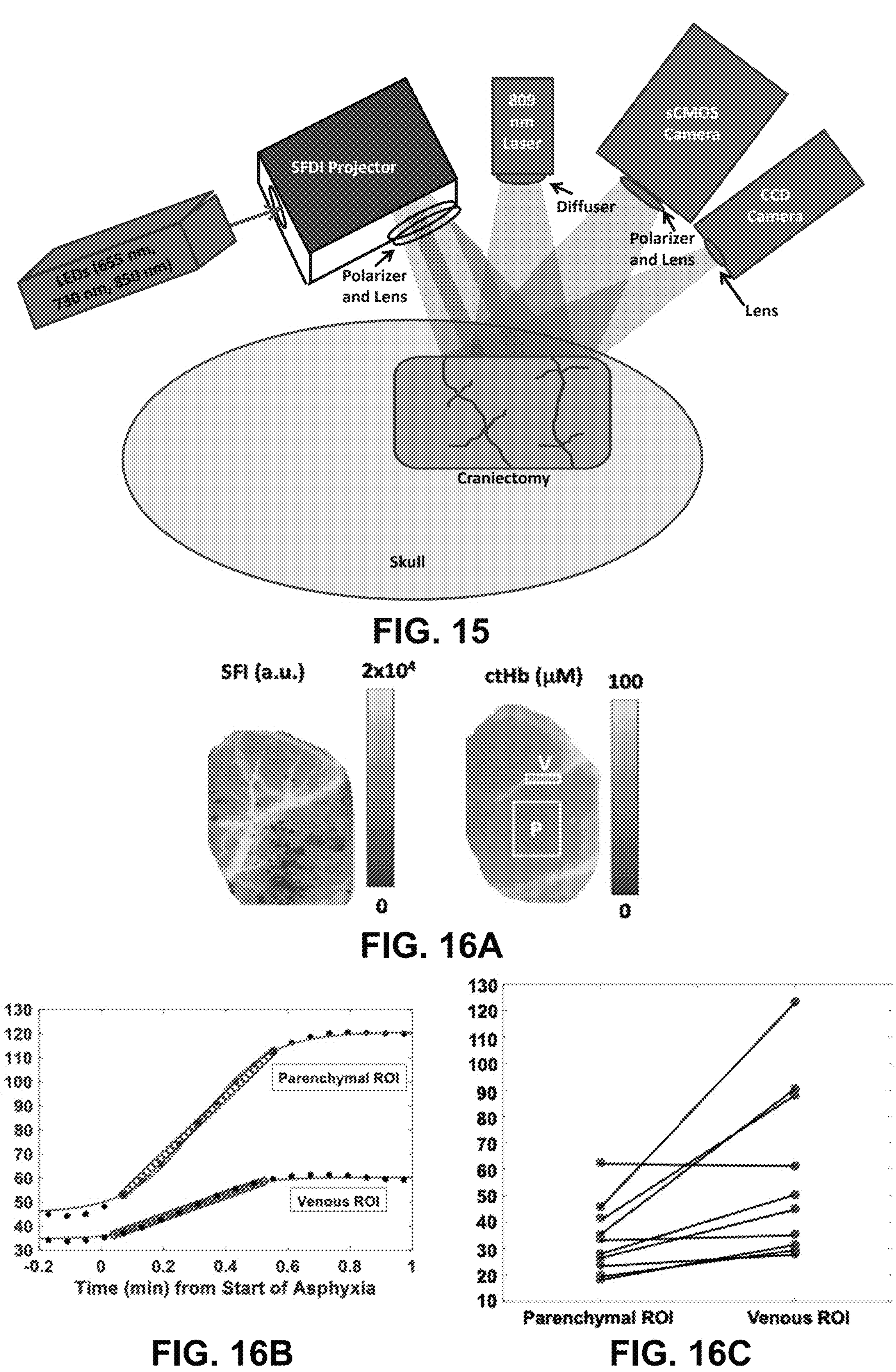
FIG. 15 shows one embodiment that is a multimodal platform (not to scale) for Laser Speckle Imaging (LSI) and multispectral Spatial Frequency Domain Imaging (SFDI) of the rat brain. A craniectomy (~6 mm×4 mm area) is performed to provide direct access to the brain for optical imaging. For SFDI, light-emitting diodes (LEDs) of 655 nm, 730 nm, and 850 nm are sequentially sent into a spatial light modulator that acts as a projector to send spatially-modulated patterns of light onto the brain. A scientific CMOS camera detects the backscattered light. For LSI, an 809 nm laser illuminates the brain with coherent light, and the remitted speckle pattern is captured at 60 fps with a CCD camera.
FIGS. 16A-C show an embodiment that illustrates how venous and parenchymal regions of interest (ROIs) demonstrate different hemodynamics in response to cardiac arrest. 16A shows images of blood flow (speckle flow index; SFI) and deoxyhemoglobin concentration (ctHb), measured from the rat brain using LSI and SFDI, respectively. ROIs over the parenchyma (P) and a large vein (V) are labeled in the ctHb image. 16B shows that ctHb (black dots) increases in these ROIs during the initial minute of asphyxia. The sigmoidal fit (red line) and linear fit (blue circles) to the measured data are used to calculate the parameter $\alpha$ in Eq. 6. 16C shows that the rate of change of tissue ctHb (dctHb/dt) during the initial minute of asphyxia is higher in the venous ROI than parenchyma ROI.

Cardiac Arrest (CA) and Cardiopulmonary Resuscitation (CPR): FIG. 15 shows the multimodal setup employed in the experiments. At the onset of each experiment, the level of isoflurane was decreased from 2% to 0.5-1.0%. Concurrently, the mixture of inhaled gases was altered from 50% $O_2$+50% $N_2$ to 100% $O_2$. Two minutes later, to reduce confounding effects of isoflurane on cerebral perfusion and metabolism, the anesthesia was turned off, at which time the subject breathed room air (21% $O_2$). During this same period, 1 mL of 2 mg/kg Vecuronium (a neuromuscular blocker) and 1 mL of heparinized saline were administered intravenously, which led to respiration controlled solely by the ventilator. This stage of the experiment lasted for 3 min, after which the ventilator was turned off to induce asphyxia, leading to progressive hypoxic hypercarbic hypotension. CA was defined as the period over which the pulse pressure was below 10 mmHg and systolic pressure below 30 mmHg. The conditions of these experiments induced pulseless electrical activity, which is common in CA patients in a hospital setting.

Forty-five seconds before the end of the CA period, the ventilator was turned on (respiratory rate=85 breaths/min, PIP=17.5-18.5 $cmH_2O$, PEEP=3 $cmH_2O$ at 2.5 LPM), and 100% oxygen was delivered. Immediately before the onset of CPR, 0.01 mg/kg epinephrine, 1 mmol/kg sodium bicarbonate, and 2 mL of heparinized saline were administered intravenously. Then, CPR was performed via external cardiac massage and terminated upon return of spontaneous circulation (ROSC), as identified from arterial blood pressure measurements. Subsequently, the animal was monitored continuously with arterial blood pressure, optical imaging, and ECoG for an additional ~2 hr, after which the animal was euthanized with pentobarbital. Recovery of ECoG signal following ROSC was quantified by (1) time to initial resumption (burst) of ECoG activity, and (2) ECoG Information Quantity (IQ) 90 min post-ROSC.

Laser Speckle Imaging (LSI): For LSI, an 809 nm laser with long coherence length served as the light source. To increase uniformity of illumination over the imaged region of interest (ROI), a ground-glass diffuser was placed between the laser and the brain. A CCD camera detected the backscattered light with a 10 ms exposure time, resulting in image acquisition at a frame rate of 60 Hz. Using a 5×5 sliding spatial window filter, the equation $K=\sigma/\langle I\rangle$ was employed to calculate the local speckle contrast K at each pixel, where $\langle I\rangle$ was the mean intensity within the filter and σ the standard deviation within the filter. Then, the speckle flow index (SFI) was determined from the values of K and the exposure time T via a simplified speckle imaging equation $SFI=1/(2TK^2)$. Time-resolved SFI curves were generated by taking the mean of the SFI over a selected ROI at each time point.

Spatial Frequency Domain Imaging (SFDI): For SFDI, light-emitting diodes (LEDs) of three different wavelengths (655 nm, 730 nm, 850 nm) were used as light sources. The light was directed to a spatial light modulator that projected square-wave patterns onto the brain. Backscattered light was captured using a scientific complementary metal-oxide semiconductor (sCMOS) camera. An Arduino Due microcontroller board was used to synchronize the camera acquisition, spatial light modulator, and LEDs. For each wavelength, four patterns were projected onto the tissue in sequence. The first pattern was non-modulated (i.e., DC illumination), and the three subsequent patterns were modulated at spatial frequency ~0.3 $mm^{-1}$ with three distinct spatial phases to enable demodulation. Thus, there were a total of (3 wavelengths×4 frames)=12 frames of SFDI data for each measurement time point. The detected square wave pattern could be approximated as a sinusoid, thus allowing demodulation. With this acquisition scheme, it was possible to reconstruct tissue hemodynamics and $CMRO_2$, at an effective imaging rate of ~14 Hz.

After demodulating the spatially-modulated data, the diffuse reflectance at each time point and wavelength was calculated from the raw data via calibration against a tissue-simulating phantom with known optical properties. The diffuse reflectance maps were then fit with a Monte Carlo model to extract the tissue absorption coefficient Ha and reduced scattering coefficient $\mu_s'$ at each wavelength. Next, the average $\mu_s'$ was determined for a selected ROI and a new $\mu_a$ determined using diffuse reflectance with the non-modulated pattern and this average $\mu_s'$. To calculate the concentrations of oxygenated and deoxygenated hemoglobin ($ctHbO_2$ and ctHb, respectively) within the tissue, this new $\mu_a(\lambda)$ spectrum was fit with the model spectrum $\mu_a(\lambda)=2.303(ctHbO_2\varepsilon_{HbO2}+ctHb\varepsilon_{Hb})$, where $\varepsilon_{HbO2}$ and $\varepsilon_{Hb}$ were the molar extinction coefficients of oxy- and deoxy-hemoglobin, respectively. The total tissue hemoglobin concentration ($ctHb_{tot}$) was calculated by summing ctHb and $ctHbO_2$. The tissue oxygen saturation was determined using the equation $StO_2=ctHbO_2/(ctHbO_2+ctHb)$.

Correction of speckle flow index for tissue absorption and scattering: K, and hence SFI, depends on local optical properties. To correct the measured SFI for dynamic optical properties, the measured K values were converted to a characteristic flow speed ($v_c$) by using the following equation:

$$K^2=\frac{\left(\frac{2}{T}\right)\int_0^T \beta G_1^2(\tau)\left(1-\frac{\tau}{T}\right)d\tau}{G_1^2(\tau=0)} \tag{1}$$

$\beta$ is a constant (typically set to 1) related to polarization and coherence properties of the LSI instrumentation. From the Siegert relationship, the intensity autocorrelation function $G_2(\tau)$ is related to $G_1(\tau)$, which, in turn, is described by the correlation diffusion equation:

$$\nabla^2 G_1(\tau)-\mu_{eff}G_1(\tau)=q \tag{2}$$

In Eq. (2), q is the source term; and $\mu_{eff}=(3\mu_{a,dyn}\mu_{tr})^{1/2}$, where $\mu_{tr}=(\mu_a+\mu_s')$ is the tissue transport coefficient and $\mu_{a,dyn}=(\mu_a+\mu_s'k_o^2\langle\Delta r^2(\tau)\rangle/3)$ the dynamic tissue absorption coefficient. In the equation for $\mu_{a,dyn}$, $\langle\Delta r^2(\tau)\rangle$ is the mean square displacement of the moving scatterers (i.e., the red blood cells) and $k_o$ is the photon wavenumber. Solving Eq. (2), $G_1(\tau)$ can be written as:

$$G_1(\tau)=\frac{3P_oA\frac{\mu_s'}{\mu_{tr}}}{\left(\frac{\mu_{eff}}{\mu_{tr}}+1\right)\left(\frac{\mu_{eff}}{\mu_{tr}}+3A\right)} \tag{3}$$

In Eq. (3), $P_o$ is the incident optical power, and A is a function of the tissue refractive index. All other terms in Eq. (3) are exclusively functions of the static and dynamic tissue absorption and scattering coefficients ($\mu_a$, $\mu_s'$, $\mu_{a,dyn}$). $\mu_{a,dyn}$ is a function of $\langle r^2(\tau)\rangle$, and $\langle r^2(\tau)\rangle$ is related to the characteristic flow speed $v_c$ via the equation $\langle r^2(\tau)\rangle=v_c\tau^2$ (for directional flow). Using this framework and inputting the measured value of K from LSI and the measured $\mu_a$ and μs' from SFDI at each time point, Eq. (1) was solved for $v_c$ at each time point and each pixel by iterating over a pre-defined grid of potential $v_c$ values and minimizing a least-squares cost function. The resulting spatiotemporal values of $v_c$ were used in place of SFI in the subsequent steps to achieve an optical property-corrected calculation of $CMRO_2$.

Absolute cerebral metabolic rate of oxygen ($CMRO_2$) calculation: To calculate absolute $CMRO_2$, the following equation is used as a starting point:

$$CMRO_2=(CBF)(OEF)([O_2]_a) \tag{4}$$

In Eq. (4), CBF is the cerebral blood flow, $[O_2]_a$ is the arterial concentration of oxygen, and OEF is the oxygen extraction fraction, equal to $([O_2]_a-[O_2]_v)/[O_2]_a$, where $[O_2]_v$ is the venous concentration of oxygen. For a single arteriole, (OEF) ($[O_2]_a$) represents the molar concentration of oxygen that was extracted from that arteriole and used by the brain for metabolic processes related to the synthesis of ATP. This quantity is equivalent to the molar concentration of deoxygenated hemoglobin that arrives in a nearby venule following oxygen extraction by the brain. Therefore, within our measurement paradigm, Eq. (4) is re-written as:

$$CMRO_2=4\alpha(v_c)(ctHb_v)(Hb_{bl}/<ctHb_{tot>p}) \tag{5}$$

In Eq. (5), $ctHb_v$ is the tissue concentration of deoxygenated hemoglobin in a region of interest atop a large vein in the ctHb maps obtained from SFDI. The factor of 4 accounts for the fact that the hemoglobin molecule has four binding sites for oxygen. Since $v_c$ is a characteristic flow parameter and not an absolute value of blood flow, it is necessary to include the proportionality constant $\alpha$ in the equation to convert $v_c$ into a quantity with units of absolute flow speed.

The factor ($Hb_{bl}/<ctHb_{tot>p}$) accounts for partial-volume effects caused by the diffuse nature of light propagation in the brain. Eq. (4) requires an intra-vascular oxygen concentration, but SFDI measures a bulk tissue deoxyhemoglobin concentration. Hence, a blood-volume fraction term is required to convert between these two quantities. The numerator, $Hb_{bl}$, is the concentration of hemoglobin in the blood sampled from the femoral artery of the animal during the arterial blood gas measurement (ABG). The denominator, $<ctHb_{tot>p}$, is the mean total tissue hemoglobin concentration in the parenchyma during the period that the ABG was acquired. The factor ($Hb_{bl}$/<$ctHb_{tot>p}$) enables the required conversion of optical ctHb measurements from the scale of a tissue hemoglobin concentration to the scale of a vascular hemoglobin concentration, mitigating the partial volume effect and allowing us to measure $CMRO_2$ on an absolute scale.

The parameter $\alpha$ is typically unknown; thus, the quantity reported in optical brain imaging studies is usually the relative $CMRO_2$ ($rCMRO_2$). However, in this example, absolute $CMRO_2$ was measured using a "zero-flow" boundary condition, which is provided by the onset of global cerebral ischemia in the animal model:

$$4\alpha(v_c)|_{t\to tasph-}(ctHb_v)|_{t\to tasph-} = 4(dctHb_v/dt)|_{t\to tasph+} \quad (6)$$

This procedure was performed for each of the 10 subjects in this study, using the values of SFI and $ctHb_v$ during the period immediately before asphyxia ($t\to t_{asph}^-$) and the mean rate of change $dctHb_v/dt$ immediately after the onset of asphyxia ($t\to t_{asph}^+$). The value of $dctHb_v/dt$ was measured by fitting a sigmoid function to the ctHb curve during the beginning of the "zero-flow" period, finding the $t_{50}$ value of the sigmoid, linearizing the sigmoid within a 30 sec window centered on the $t_{50}$ point, and calculating the slope of the resulting line segment. The values of $\alpha$ and absolute $CMRO_2$ then were calculated over the entire craniectomy region at each measurement time point.

Results: Immediately following cardiac arrest, cerebral hemodynamics are spatially heterogeneous (FIGS. 16A-C). For example, the rate of change in cerebral ctHb following the start of asphyxia was 58.3±32.3 μM/min in a ROI selected over a large vein (FIG. 16B), but only 33.6±13.6 μM/min in a ROI selected over the parenchyma.

Figure 17:
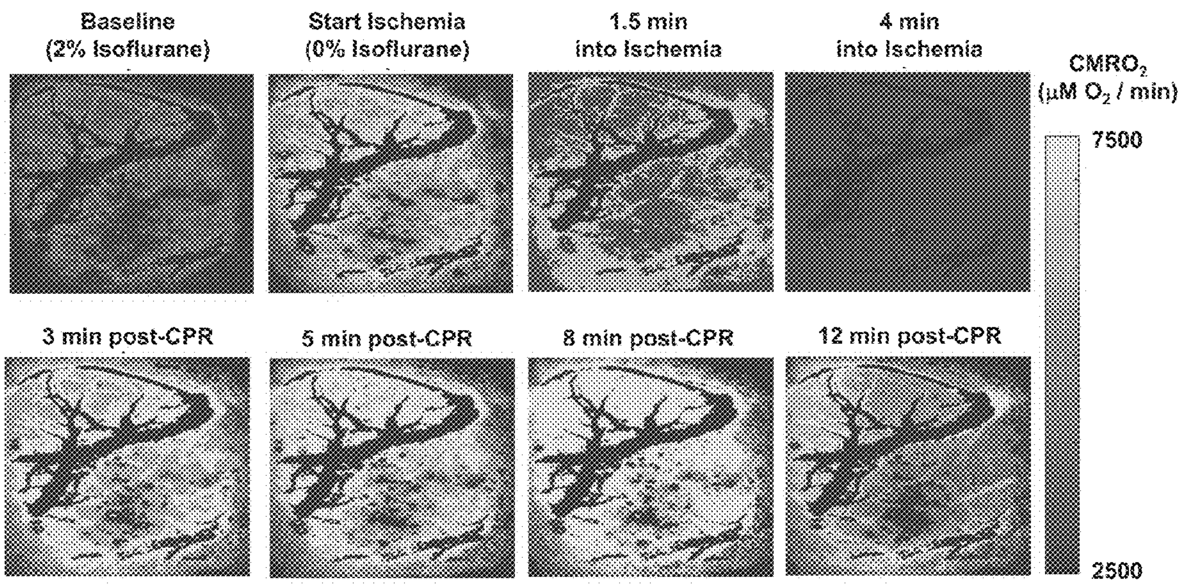
FIG. 17 shows an embodiment showing absolute $CMRO_2$ ($\mu M\ O_2$/min) maps of a ~6 mm×4 mm region of the rat brain at different time points during a CA/CPR experiment. Metabolic activity increases as anesthesia is being washed out (between "Baseline" and "Start Ischemia"), followed by a sharp decrease during ischemia. Following CPR, $CMRO_2$ recovers to anesthesia-free baseline level ("3 min post-CPR"), subsequently increases to values higher than baseline ("5-8 min post-CPR"), and then declines to values approaching anesthetized baseline level once cerebral electrical activity resumes ("12 min post-CPR"). Large vessels (dark blue) have been removed from the $CMRO_2$ images to signify that the oxygen metabolism measured is occurring in the parenchyma.

Maps of absolute $CMRO_2$ throughout a representative CA/CPR experiment are shown in FIG. 17. At baseline, the animal is under anesthesia (2% isoflurane). After 2 min of anesthesia washout, the $CMRO_2$ increased by a factor of ~2 as the subject woke up. Following the onset of ischemia, the $CMRO_2$ rapidly decreased as the subject entered CA. After resuscitation, the $CMRO_2$ rapidly increased until reaching a maximum value at ~8 min post CPR (during hyperemia). Subsequently, the $CMRO_2$ decreased towards baseline as cerebral electrical activity resumed (~12 min post-CPR).

Figure 18:
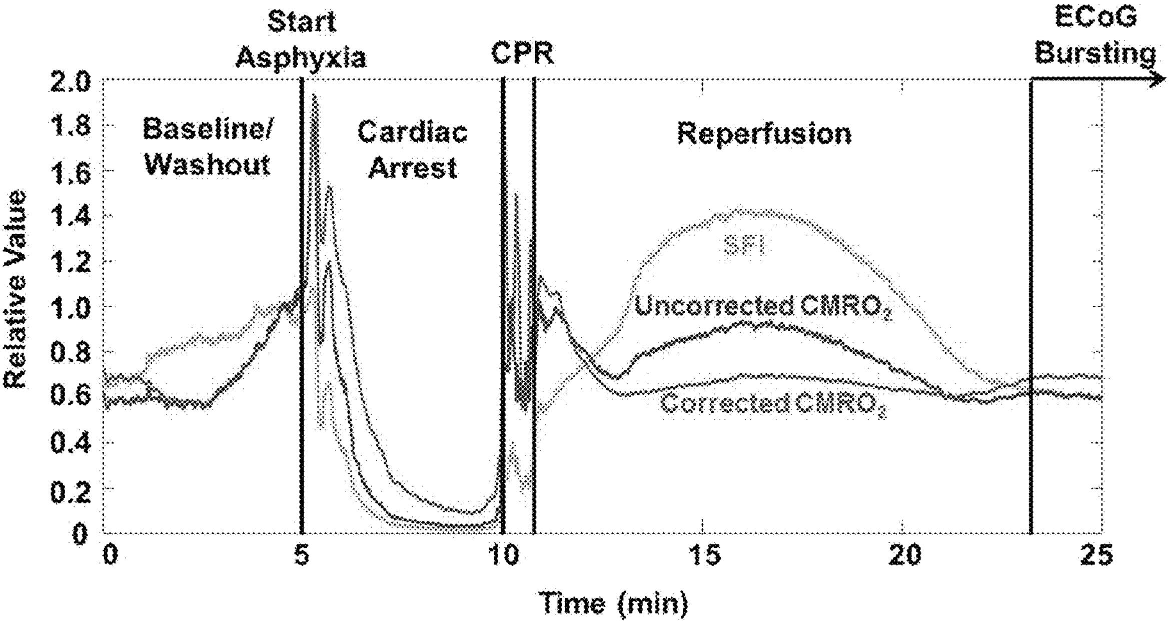
FIG. 18 shows an embodiment showing how optical properties affect calculation of $CMRO_2$. Comparison of SFI (light blue), $CMRO_2$ calculated using SFI (dark blue), and $CMRO_2$ calculated using $v_c$ (red), which corrects for the effects of tissue optical properties on SFI. For ease of comparison, the three curves are normalized to their value at a point near the end of the washout period (t~4 min). This correction reveals differences in the observed rates of change in $CMRO_2$ during reperfusion and resumption of ECoG bursting, suggesting the need to take optical properties into account even for $rCMRO_2$ measurements.

Calculation of changes in $CMRO_2$ are affected by optical properties (FIG. 18). Optical properties measured with SFDI, along with Eq. (1), enable calculation of a characteristic flow speed ($v_c$) that can be used in place of SFI for the calculation of relative $CMRO_2$ ($rCMRO_2$). During each of the experimental phases, a comparison of $rCMRO_2$ trends suggests that the metabolic activity is at times greater (i.e., during the hyperemic phase) and lower (i.e., during cardiac arrest) with use of SFI instead of $v_c$ in the calculation of $CMRO_2$. This result demonstrates the effects that hyperdynamic changes in cerebral optical properties can have on calculations of $CMRO_2$ dynamics using SFI alone to measure flow.

Figure 19A:
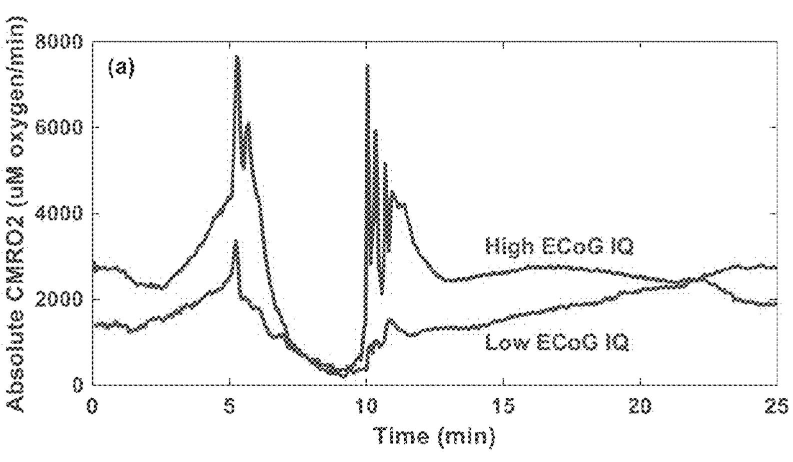
FIGS. 19A-C show an embodiment demonstrating how cerebral electric activity after resuscitation from cardiac arrest is associated with baseline (pre-cardiac arrest) $CMRO_2$. 19A shows time courses of absolute $CMRO_2$ for two representative subjects. The subject with the higher baseline absolute $CMRO_2$ (blue) had higher ECoG Information Quantity (IQ) 90 min post-CPR than the one with the lower baseline absolute $CMRO_2$ (red). 19B shows a scatter plot illustrating correlation (Spearman; r=0.63; p=0.076) between baseline absolute $CMRO_2$ and cerebral electrical activity (ECoG IQ) 90 min post-CPR. Blue dots are subjects with mild (5 min) ischemia duration, and red dots are subjects with prolonged (7 min) ischemia duration. These results suggest that the pre-injury, baseline value of $CMRO_2$ may be predictive of cerebral electrical recovery following CA and CPR. 19C shows that subjects in the "High IQ" group (ECoG IQ>0.75) had significantly higher baseline absolute $CMRO_2$ than subjects in the "Low IQ" group (ECoG IQ<0.75) 90 min post-CPR (p=0.016).
Figure 19B:
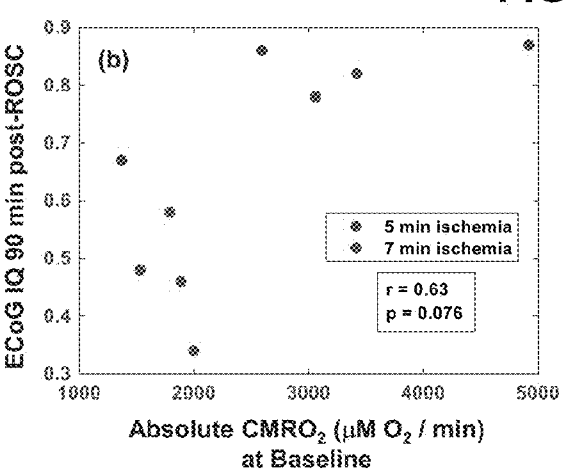
Figure 19C:
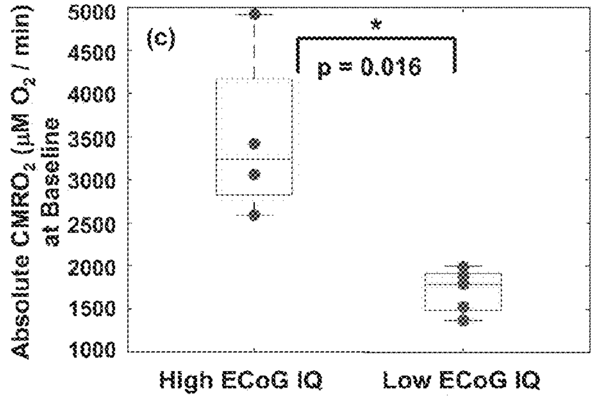

Measurements of baseline $CMRO_2$ alone are associated with ECoG IQ (FIGS. 19A-C). For the 10 subjects included in this study, it was observed that higher absolute $CMRO_2$ values at baseline (with 5 min and 7 min CA durations pooled) were associated with increased cerebral electrical activity (ECoG IQ) 90 min post-CPR (Spearman; r=0.63; p=0.076) (FIG. 19B). Further analysis was performed by dividing the subjects into "High IQ" and "Low IQ" groups with ECoG values greater than or less than 0.75, respectively. The baseline absolute $CMRO_2$ was significantly different between the "High IQ" and "Low IQ" groups (FIG. 19C; p=0.016). These data collectively suggest that the absolute $CMRO_2$ measurement at baseline may help to predict cerebral electrical recovery following CA and CPR.

Figure 20:
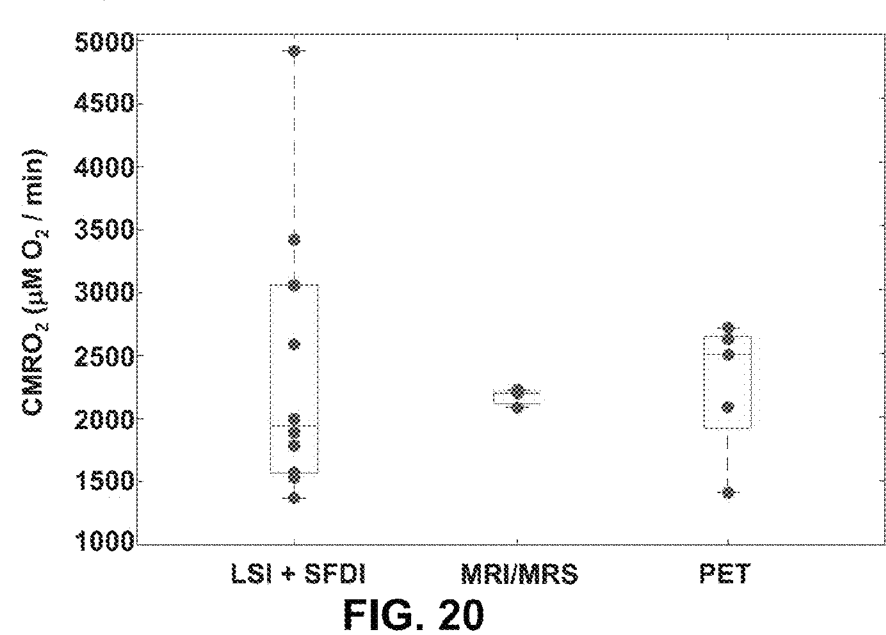
FIG. 20 shows an embodiment in which absolute $CMRO_2$ values (μM $O_2$/min) measured with the combined SFDI+LSI optical system are in with the range of absolute $CMRO_2$ values reported in previous preclinical studies using different imaging modalities (MRI/MRS, PET). Each LSI+SFDI data point represents an individual subject (n=10) imaged in this report. Each data point for MRI/MRS and PET represents the reported average $CMRO_2$ of the subjects measured in individual studies.
Figure 22A:
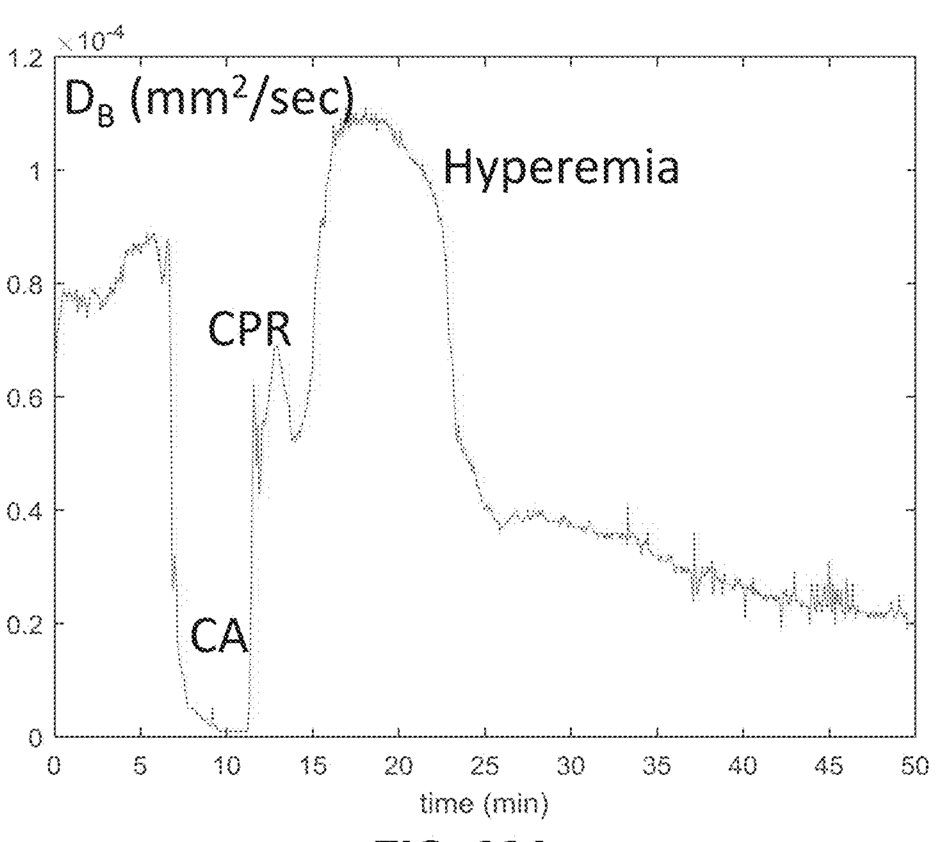
FIG. 22A shows an embodiment where the Brownian diffusion coefficient Db is calculated to quantify cerebral blood flow in physiological units ($mm^2$/sec) at multiple time points throughout a cardiac arrest and resuscitation experiment in a rat. The calculation of Db is performed using a method similar to that in FIG. 13, where the measured blood flow index is corrected for tissue absorption and scattering coefficients.
Figure 22B:
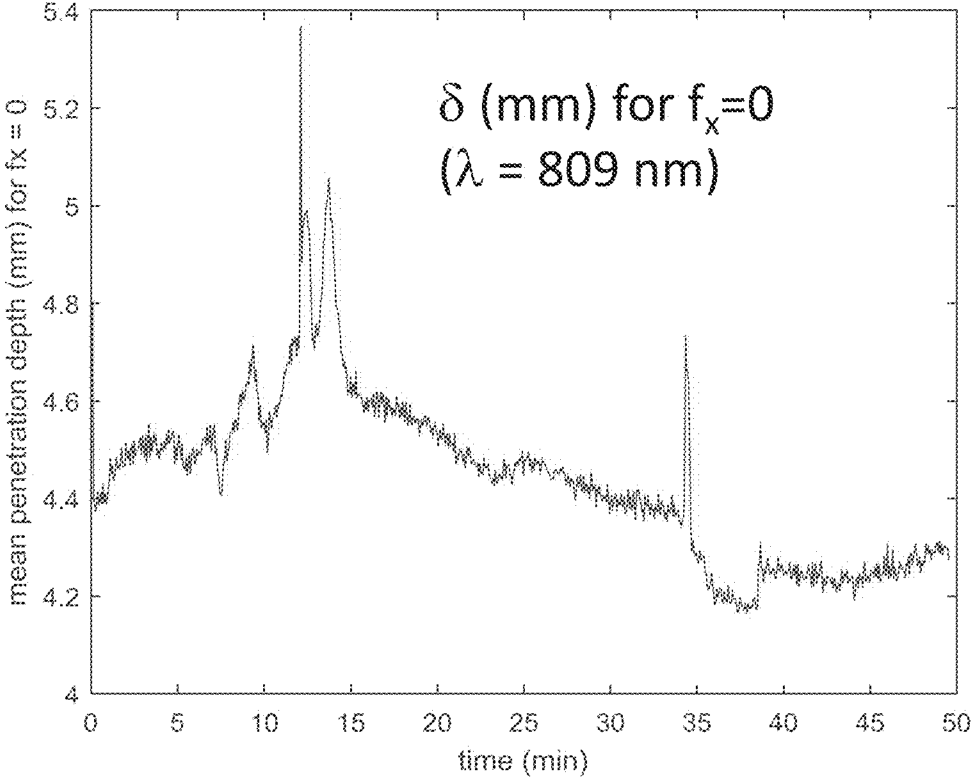
FIG. 22B shows an embodiment where the mean penetration depth of unmodulated ($f_x$=0) near-infrared light in tissue is estimated using a diffusion model with the measured tissue absorption and scattering coefficients, for use in the metabolic rate of oxygen calculation described in FIG. 21.
Figure 22C:
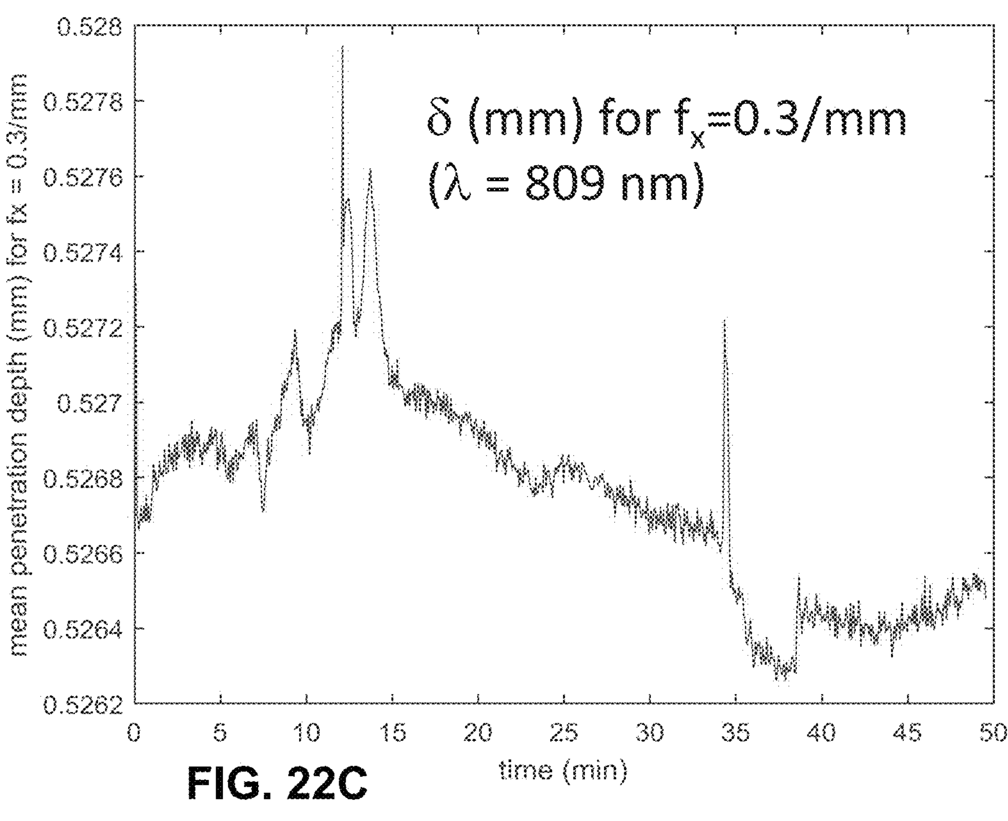
FIG. 22C shows an embodiment where the mean penetration depth of modulated ($f_x$~0.3/mm) near-infrared light in tissue is estimated using a diffusion model with the measured tissue absorption and scattering coefficients, for use in the metabolic rate of oxygen calculation described in FIG. 21.
Figure 23:
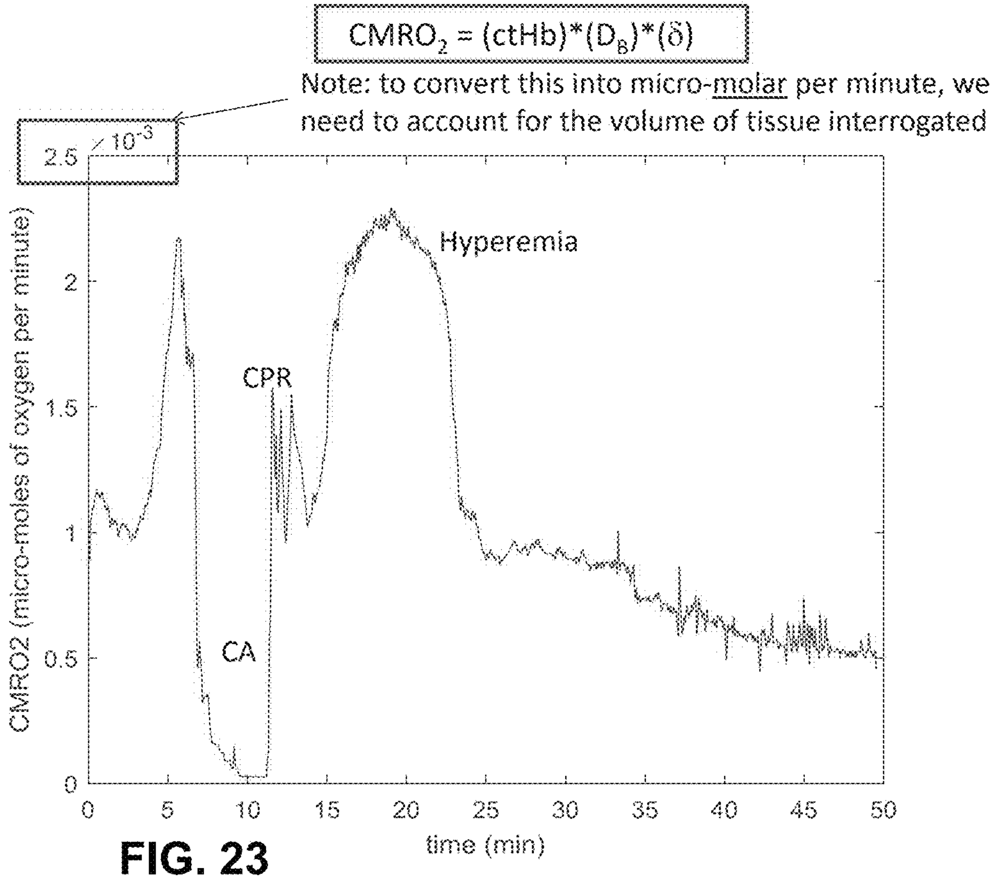
FIG. 23 shows an embodiment where the cerebral metabolic rate of oxygen (CMRO2) in physiological units (micro-moles of oxygen per minute) is calculated (using the method described in FIG. 21) at multiple time points throughout a cardiac arrest and resuscitation experiment in a rat.
Figure 24:
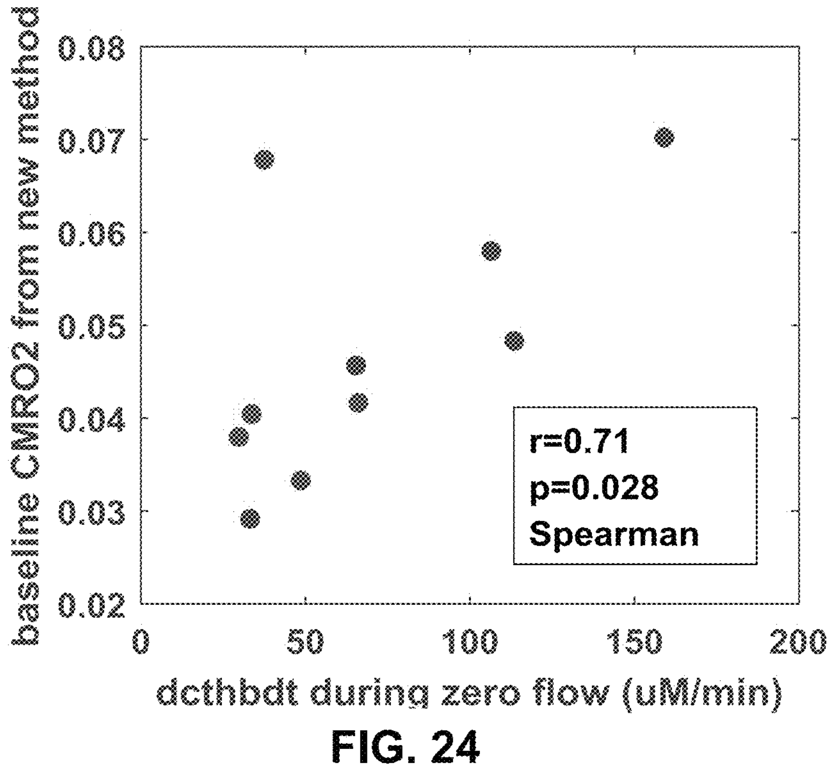
FIG. 24 shows an embodiment illustrating a significant correlation between the slope of the deoxy-hemoglobin concentration during entry into cardiac arrest in a rat model and the baseline CMRO2 calculated with the method described in FIG. 21.
Figure 25:
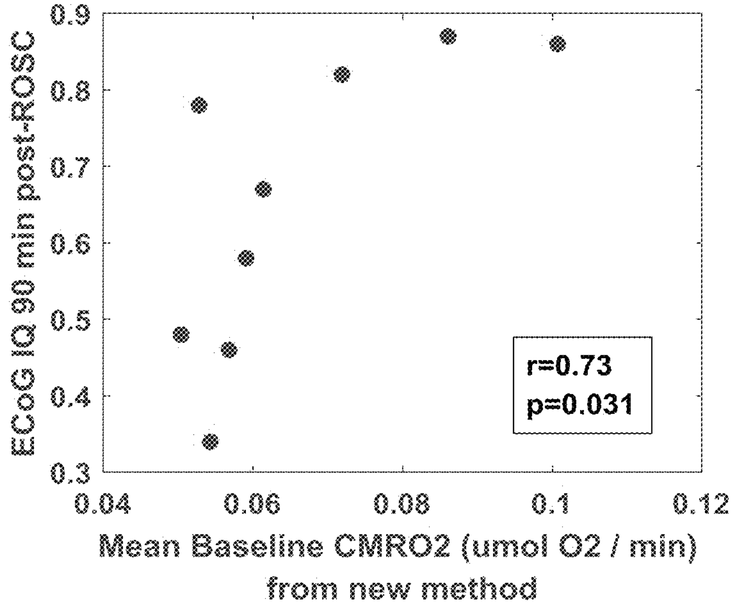
FIG. 25 shows an embodiment illustrating that the mean baseline CMRO2 (over the last minute prior to start of asphyxia in our rat model of cardiac arrest), calculated with the method described in FIG. 21, correlates with recovery of cerebral electrical activity (ECoG Information Quantity; IQ) 90 minutes after resuscitation from cardiac arrest.
Figure 26:
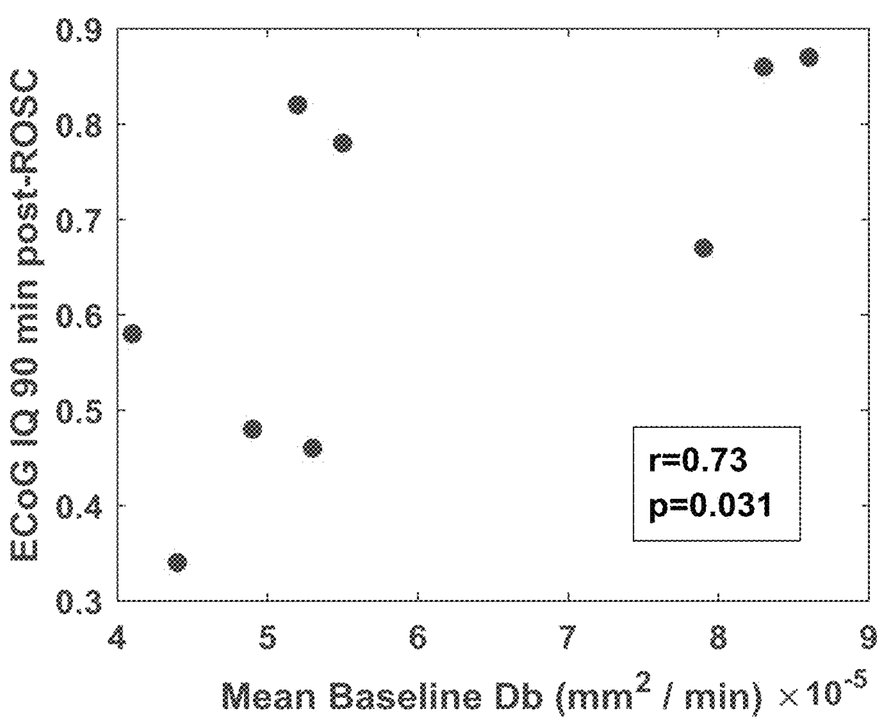
FIG. 26 shows an embodiment illustrating that the mean baseline Brownian diffusion coefficient Db of cerebral blood flow (over the last minute prior to start of asphyxia in our rat model of cardiac arrest), calculated with the method described in FIG. 22A, correlates with recovery of cerebral electrical activity (ECoG Information Quantity; IQ) 90 minutes after resuscitation from cardiac arrest.
Figure 28:
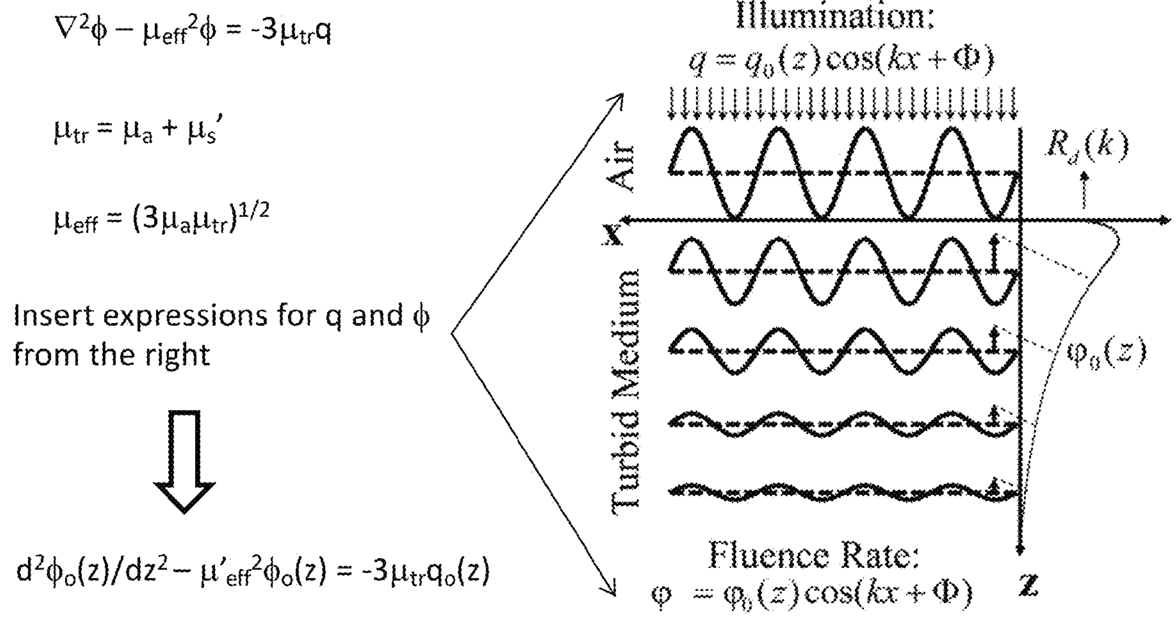
FIG. 28 shows an illustration of a penetration depth model for determining mean penetration depth, using the example of spatially modulated light. For additional explanation of this non-limiting example model, the publication *Quantitation and Mapping of Tissue Optical Properties Using Modulated Imaging* (D. J. Cuccia, et al. J. Biomed. Opt. 14, 024012 (2009)) is incorporated herein in its entirety by reference.

FIG. 20 shows distributions of $CMRO_2$ values measured with the imaging setup of the present example, as compared to values reported in the literature using various medical imaging approaches, including magnetic resonance methods (MRI/MRS) and positron emission tomography (PET). The LSI+SFDI method reported here measures absolute $CMRO_2$ values that are within the range measured with these approaches, suggesting the accuracy of this optical imaging approach to determine $CMRO_2$.

Discussion: The present example is believed to be the first demonstration of dynamic imaging of absolute cerebral metabolic rate of oxygen ($CMRO_2$) in the living brain using a combination of LSI and SFDI techniques. Tissue optical properties were measured with SFDI to account for their effects on interpretation of the LSI information. The "zero-flow" condition inherent in the CA experimental paradigm were then used to solve for the coefficient $\alpha$ in the $CMRO_2$ equation by using a continuity condition at the boundary between normal flow and zero-flow states. Using this technique, quantitative spatial mapping of absolute $CMRO_2$ was performed continuously throughout the different stages of the CA+CPR experiment. The $CMRO_2$ obtained from this optical system agreed well with established brain imaging techniques (PET, MRI/MRS). As an application, from ongoing research on optical and electrocerebral measurements during CA and CPR, there is a significant difference between baseline absolute $CMRO_2$ values of rats with high ECoG IQ (>0.75) 90 min post-ROSC and rats with low ECoG IQ (<0.75) 90 min post-CPR, pooled across both 5 and 7 min CA durations.

This paradigm for measuring absolute $CMRO_2$, in units of μM $O_2$/min, enables direct comparison of metabolic activity among subjects, across separate imaging sessions, and on different days for a single subject. This approach potentially enables longitudinal monitoring of cerebral recovery for days or weeks following ischemia and reperfusion. The methods of the present example may be applied to quantitative measurement of metabolic recovery and flow-metabolic coupling and uncoupling in preclinical models of ischemic conditions such as CA and stroke.

Optical Imaging Segments Venous Regions to Better Quantify Cerebral Oxygen Extraction: The imaging capability of the device of the present example allows the segmentation of a ROI atop a prominent vein, which enables more accurate measurements of the quantity of deoxygenated venous blood and, hence, the quantity of oxygen consumed by the brain. With the use of a larger ROI, the local $CMRO_2$ would be systematically underestimated due to inclusion of the parenchyma in the ROI, as oxygen extraction in the parenchyma is lower than in individual vessels. $CMRO_2$ models of diffuse light transport implicitly assume that the concentration of deoxygenated hemoglobin is that within the veins specifically, and not the bulk tissue. However, most diffuse optics-based $CMRO_2$ measurements are unable to satisfy this condition, as they typically use fiber-based spectroscopic techniques that sample the bulk tissue and thus cannot distinguish between venous and mixed arterial-venous parenchymal regions. In this example, the use of diffuse optical imaging allows the use of deoxyhemoglobin concentrations measured in a venous ROI to overcome this limitation and thus obtain more accurate quantitative values of $CMRO_2$.

Correction of $CMRO_2$ Data for Partial-Volume Effects: Simply selecting a ROI that is coincident with a venule is not enough. To further refine the measurement of deoxygenated hemoglobin into an intravascular hemoglobin concentration, a partial-volume correction to the $CMRO_2$ equation was employed. To accurately incorporate this scaling term, it is necessary to know the concentration of total hemoglobin ($Hb_{bl}$) within the blood of each animal. In this example, these values were acquired via arterial blood gas (ABG) measurement before CA. A coefficient of variation of 13% in $Hb_{bl}$ was determined from the measurements. If the variation in $Hb_{bl}$ among the different subjects were not considered, an additional error of ~12-25% in the measured $CMRO_2$ would be achieved due to this within-group variability in $Hb_{bl}$ values.

Contributions of Directed Flow versus Diffuse Flow: Here, it was assumed that the corrected flow speed could be attributed solely to a "directed-flow" term (Eq. 2). Previous studies have used a Brownian diffusion term as the free parameter when fitting for flow speed or constrained the fit in a model system such that one could choose to fit for either diffuse or directed flow, but not both simultaneously. Some have used high-speed LSI to map the autocorrelation function pixel-by-pixel in the rodent brain, identifying the dominant type of particle motion at each pixel. They observed that the directed flow term was dominant in large vessels, while the diffuse flow term was dominant in the parenchyma.

In the present example, it was not possible to rigorously solve for the autocorrelation function because the sampling frequency of the LSI data acquisition was too low. Instead, a two-step approach was used, which consisted of (1) using SFDI data to account for the effects of optical properties on interpreting the LSI data, and (2) fitting the resulting corrected data to a model of directed flow to extract a characteristic flow speed. This method provided characteristic flow speeds that were similar to previously-reported values.

Limitations of Zero-Flow Condition: One approach for measuring absolute $CMRO_2$ requires temporary induction of a "zero-flow" condition in the brain. In this example, this condition was met by using a CA model in rats. However, there is a clear need for alternative approaches for interrogating absolute $CMRO_2$ without creating harmful perturbations. Theses alternative approaches may incorporate techniques such as temporarily clamping the middle cerebral artery or administering sub-lethal doses of potassium chloride to temporarily induce a zero-flow condition that can be quickly reversed without long-term harm to the animal.

Conclusion:

This is believed to be the first example of absolute cerebral metabolic rate of oxygen ($CMRO_2$) mapping in the rat brain using diffuse optical imaging. $CMRO_2$ allows for quantitative assessment of cerebral metabolism without the need for baseline measurements, enabling longitudinal comparison between animals and among multiple days of measurement on an absolute scale. The $CMRO_2$ measurements provided by this multimodal system were in good agreement with those previously measured in the brain of anesthetized rats using PET and MRI. This method shows significant potential for assessing and monitoring cerebral metabolism and predicting cerebral response to ischemic injury.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

What is claimed is:

1. A method of determining an absolute value of cerebral metabolic rate of oxygen ($CMRO_2$) using a volumetric calibration, the method comprising:

a. positioning one or more light sources and two or more detectors in proximity to a head of a subject;

b. emitting a coherent light signal from one or more of the light sources into the head, such that one or more backscattered light signals are generated;

c. detecting one or more of the backscattered light signals via the two or more detectors, wherein the detected signals correspond to an optically measured volume of tissue;

d. calculating a tissue absorption coefficient and a tissue scattering coefficient from the detected signals;

e. calculating a calibrated perfusion metric representing perfusion over an area of the volume of tissue from the detected signals;

f. calculating a deoxygenated hemoglobin concentration (ctHb) in the volume of tissue from the tissue absorption coefficient;

g. calculating a mean penetration depth of the detected signals, using the tissue absorption coefficient and tissue scattering coefficient; and h. calculating an absolute value of $CMRO_2$ from the deoxygenated hemoglobin concentration, the calibrated perfusion metric, and the mean penetration depth.

2. The method of claim 1, wherein the tissue absorption coefficient and tissue scattering coefficient are determined via Spatial Frequency Domain Imaging (SFDI), Diffuse Optical Spectroscopy (DOS), or Near Infrared Spectroscopy (NIRS).

3. The method of claim 1, wherein the calibrated perfusion metric is determined via Laser Speckle Imaging (LSI), Diffuse Correlation Spectroscopy (DCS), or Laser Doppler Imaging (LDI).

4. The method of claim 1, wherein the calibrated perfusion metric is determined via calibration of a dynamic perfusion metric using the tissue absorption coefficient and the tissue scattering coefficient.

5. The method of claim 4, wherein the dynamic perfusion metric comprises a speckle flow index (SFI) or a blood flow index (BFI), and the calibrated perfusion metric comprises a Brownian diffusion coefficient (Db), a directed flow speed ($v_c$), a cerebral blood flow (CBF) or a combination thereof.

* * * * *